US011006821B2

(12) United States Patent
Daidoji et al.

(10) Patent No.: US 11,006,821 B2
(45) Date of Patent: May 18, 2021

(54) ENDOSCOPE APPARATUS FOR CHANGING LIGHT QUANTITY RATIO BETWEEN FIRST EMPHASIS NARROW BAND LIGHT AND FIRST NON-EMPHASIS NARROW BAND LIGHT AND LIGHT QUANTITY RATIO BETWEEN SECOND EMPHASIS NARROW BAND LIGHT AND SECOND NON-EMPHASIS NARROW BAND LIGHT

(71) Applicant: OLYMPUS CORPORATION, Tokyo (JP)

(72) Inventors: Bakusui Daidoji, Hachioji (JP); Takeshi Ito, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 519 days.

(21) Appl. No.: 15/947,110

(22) Filed: Apr. 6, 2018

(65) Prior Publication Data

US 2018/0228355 A1    Aug. 16, 2018

Related U.S. Application Data

(63) Continuation of application No. PCT/JP2015/078620, filed on Oct. 8, 2015.

(51) Int. Cl.
*A61B 1/06* (2006.01)
*A61B 1/07* (2006.01)
(Continued)

(52) U.S. Cl.
CPC ............ *A61B 1/07* (2013.01); *A61B 1/00009* (2013.01); *A61B 1/063* (2013.01); *A61B 1/0638* (2013.01);
(Continued)

(58) Field of Classification Search
CPC ...... A61B 1/00009; A61B 1/07; A61B 1/0653; A61B 1/0646; A61B 1/0638; A61B 1/063
See application file for complete search history.

(56) References Cited

U.S. PATENT DOCUMENTS

| 2003/0176768 A1* | 9/2003 | Gono | A61B 5/0084 |
| | | | 600/109 |
| 2007/0276185 A1* | 11/2007 | Gono | A61B 1/0008 |
| | | | 600/156 |

(Continued)

FOREIGN PATENT DOCUMENTS

| CN | 108024689 A | 5/2018 |
| EP | 3 354 188 A1 | 8/2018 |

(Continued)

OTHER PUBLICATIONS

International Search Report dated Jan. 12, 2016 issued in PCT/JP2015/078620.

(Continued)

*Primary Examiner* — John P Leubecker
*Assistant Examiner* — Shankar Raj Ghimire
(74) *Attorney, Agent, or Firm* — Scully, Scott, Murphy & Presser, P.C.

(57) ABSTRACT

An endoscope apparatus includes an illuminator including: an emphasis light source that emits emphasis narrow band light whose peak or central wavelength is included in an emphasis wavelength range that includes a maximum wavelength taking a maximum value of an optical absorption spectrum of a diagnosis target substance or a largest wavelength taking a largest value of the spectrum in any of three color ranges; and a non-emphasis light source that emits non-emphasis narrow band light whose peak or central wavelength is included in a non-emphasis wavelength range that is a wavelength range not including the emphasis wavelength range of the color ranges. The illuminator fur- (Continued)

ther includes a light quantity ratio changing section that changes a light quantity ratio between the emphasis and non-emphasis narrow band light.

27 Claims, 19 Drawing Sheets

(51) Int. Cl.
*A61B 1/00* (2006.01)
*A61B 1/04* (2006.01)
*G01N 21/64* (2006.01)
*G02B 6/42* (2006.01)

(52) U.S. Cl.
CPC .......... *A61B 1/0646* (2013.01); *A61B 1/0653* (2013.01); *A61B 1/043* (2013.01); *A61B 1/0684* (2013.01); *G01N 21/6456* (2013.01); *G01N 2021/6484* (2013.01); *G01N 2201/0612* (2013.01); *G02B 6/4296* (2013.01)

(56) References Cited

U.S. PATENT DOCUMENTS

| | | | | |
|---|---|---|---|---|
| 2009/0005693 A1* | 1/2009 | Brauner | ................ | G06T 7/62 600/481 |
| 2009/0023991 A1* | 1/2009 | Gono | ................ | A61B 1/00009 600/109 |
| 2009/0058999 A1* | 3/2009 | Gono | ................ | G01J 3/50 348/71 |
| 2009/0091614 A1* | 4/2009 | Gono | ................ | G01J 3/50 348/68 |
| 2011/0077462 A1* | 3/2011 | Saitou | ................ | A61B 1/063 600/109 |
| 2011/0230715 A1* | 9/2011 | Saito | ................ | G06T 7/0012 600/109 |
| 2011/0237883 A1* | 9/2011 | Chun | ................ | A61B 1/0638 600/109 |
| 2011/0237915 A1* | 9/2011 | Yamaguchi | ........ | A61B 5/14551 600/339 |
| 2011/0245642 A1* | 10/2011 | Minetoma | ............ | A61B 5/0084 600/324 |
| 2011/0319711 A1* | 12/2011 | Yamaguchi | ........ | A61B 5/14551 600/109 |
| 2012/0176486 A1* | 7/2012 | Maeda | ................ | G01J 3/10 348/68 |
| 2012/0265041 A1 | 10/2012 | Yamaguchi et al. | | |
| 2013/0018242 A1* | 1/2013 | Yamaguchi | ........ | A61B 5/0084 600/339 |
| 2014/0187881 A1* | 7/2014 | Saito | ................ | A61B 1/0638 600/323 |
| 2014/0316283 A1* | 10/2014 | Kaku | ................ | A61B 1/0638 600/479 |
| 2015/0094538 A1* | 4/2015 | Terakawa | ........... | A61B 1/00009 600/160 |
| 2015/0185421 A1* | 7/2015 | Leavesley | ............ | A61B 1/0669 356/445 |
| 2015/0363932 A1* | 12/2015 | Hirota | ................ | A61B 1/041 382/128 |
| 2018/0000335 A1* | 1/2018 | Igarashi | ............ | H04N 5/2354 |
| 2018/0279853 A1 | 10/2018 | Daidoji et al. | | |

FOREIGN PATENT DOCUMENTS

| | | |
|---|---|---|
| JP | 2002-095635 A | 4/2002 |
| JP | 2012-228503 A | 11/2012 |
| JP | 2013005981 A | 1/2013 |
| JP | 2014061152 A | 4/2014 |
| JP | 2014161627 A | 9/2014 |
| JP | 2015066050 A | 4/2015 |
| JP | 2015527718 A | 9/2015 |
| WO | 2014/132695 A1 | 9/2014 |

OTHER PUBLICATIONS

Extended Supplementary European Search Report dated Mar. 21, 2019 in European Patent Application No. 15 90 5822.1.
Chinese Office Action dated Jul. 2, 2019 in Chinese Patent Application No. 201580083634.0.
Chinese Office Action dated Mar. 11, 2020 in Chinese Patent Application No. 201580083634.0.
English translation of International Preliminary Report on Patentability dated Apr. 19, 2018 together with the Written Opinion received in related International Application No. PCT/JP2015/078620.
Japanese Office Action dated Jun. 4, 2019 in Japanese Patent Application No. 2017-544128.

* cited by examiner

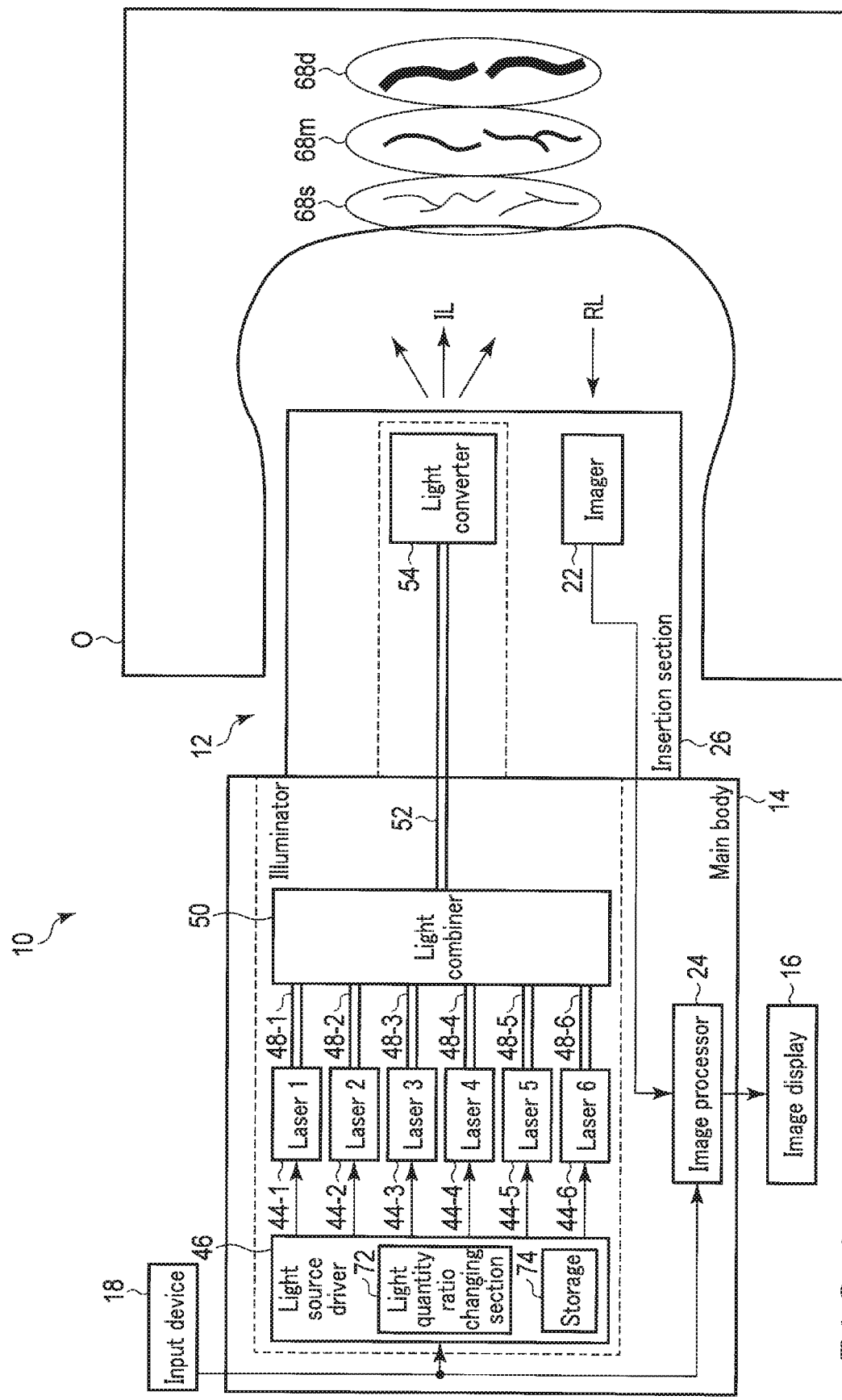
F I G. 1

|     | Laser 1 (emphasis light source for superficial blood vessels) | Laser 2 (non-emphasis light source for superficial blood vessels) | Laser 3 (emphasis light source for intermediate blood vessels) | Laser 4 (non-emphasis light source for intermediate blood vessels) | Laser 5 (emphasis light source for deep blood vessels) | Laser 6 (non-emphasis light source for deep blood vessels) |
|-----|-----|-----|-----|-----|-----|-----|
| M1  | ON  | –   | –   | ON  | –   | ON  |
| M2  | –   | ON  | ON  | –   | –   | ON  |
| M3  | –   | ON  | –   | ON  | ON  | –   |
| M4  | ON  | –   | ON  | –   | –   | ON  |
| M5  | ON  | –   | –   | ON  | ON  | –   |
| M6  | –   | ON  | ON  | –   | ON  | –   |
| M7  | ON  | –   | ON  | –   | ON  | –   |
| M8  | ON  | –   | ON  | ON  | –   | ON  |
| M9  | ON  | ON  | ON  | –   | –   | ON  |
| M10 | ON  | –   | –   | ON  | ON  | ON  |
| M11 | ON  | ON  | –   | ON  | ON  | –   |
| M12 | –   | ON  | ON  | –   | ON  | ON  |
| M13 | –   | ON  | ON  | ON  | ON  | –   |
| M14 | ON  | –   | ON  | ON  | ON  | ON  |
| M15 | ON  | ON  | ON  | –   | ON  | ON  |
| M16 | ON  | ON  | ON  | ON  | ON  | –   |
| M17 | ON  | ON  | ON  | ON  | ON  | ON  |

F I G. 7

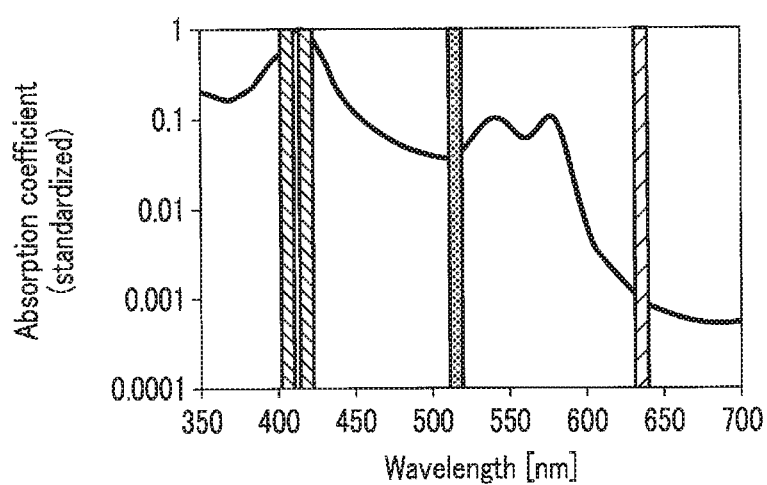
F I G. 27

| | Sub frame 1/4 | Sub frame 2/4 | Sub frame 3/4 | Sub frame 4/4 | Sub frame 1/4 | Sub frame 2/4 | Sub frame 3/4 | Sub frame 4/4 |
|---|---|---|---|---|---|---|---|---|
| Laser 1 (415nm) | ON | - | - | ON | ON | - | - | ON |
| Laser 2 (445nm) | - | - | ON | ON | - | ON | ON | ON |
| Laser 3 (540nm) | - | ON | - | ON | - | ON | - | ON |
| Laser 4 (515nm) | ON | - | ON | ON | - | - | ON | ON |
| Laser 5 (595nm) | - | - | ON | ON | - | - | ON | ON |
| Laser 6 (635nm) | ON | ON | - | ON | ON | - | - | ON |
| | Superficial blood vessel emphasis mode | Intermediate blood vessel emphasis mode | Deep blood vessel emphasis mode | Normal observation mode | Superficial blood vessel emphasis mode | Intermediate blood vessel emphasis mode | Deep blood vessel emphasis mode | Normal observation mode |

F I G. 28

|  | 1 Frame | | 1 Frame | |
|---|---|---|---|---|
|  | Sub frame 1/2 | Sub frame 2/2 | Sub frame 1/2 | Sub frame 2/2 |
| Laser 1 (415nm) | ON | - | ON | - |
| Laser 2 (445nm) | - | ON | - | ON |
| Laser 3 (540nm) | ON | - | ON | - |
| Laser 4 (515nm) | - | ON | - | ON |
| Laser 5 (595nm) | ON | - | ON | - |
| Laser 6 (635nm) | - | ON | - | ON |
F I G. 29
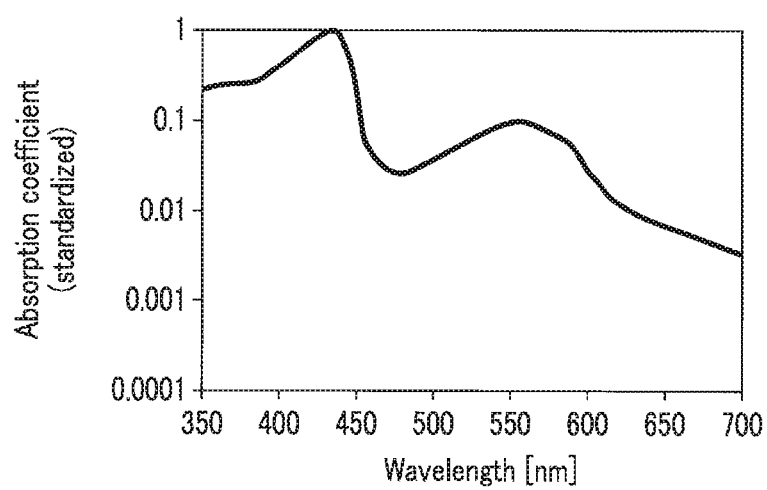
F I G. 30

ENDOSCOPE APPARATUS FOR CHANGING LIGHT QUANTITY RATIO BETWEEN FIRST EMPHASIS NARROW BAND LIGHT AND FIRST NON-EMPHASIS NARROW BAND LIGHT AND LIGHT QUANTITY RATIO BETWEEN SECOND EMPHASIS NARROW BAND LIGHT AND SECOND NON-EMPHASIS NARROW BAND LIGHT

CROSS-REFERENCE TO RELATED APPLICATIONS

This application is a Continuation Application of PCT Application No. PCT/JP2015/078620, filed Oct. 8, 2015, the entire contents of which are incorporated herein by reference.

BACKGROUND OF THE INVENTION

1. Field of the Invention

The present invention relates to an endoscope apparatus capable of highlighting a diagnosis target substance present in an observation object.

2. Description of the Related Art

For example, Jpn. Pat. Appln. KOKAI No. 2014-61152 discloses an endoscope apparatus capable of highlighting a blood vessel of an observation object. This endoscope apparatus includes blood vessel emphasis filters that allow transmission of light of wavelength ranges of 405 to 425 nm and 530 to 550 nm for broadband light, which have a high absorption coefficient for hemoglobin, the diagnosis target substance present in the observation target, and which are used as blood vessel emphasis illumination light. Of the blood vessel emphasis illumination light that is illumination light transmitted through the blood vessel emphasis filters, the blue narrow band light of 405 to 425 nm serves to obtain an image signal in which superficial blood vessels have a high contrast and the green narrow band light of 530 to 550 nm serves to obtain an image signal in which middle-deep blood vessels have a high contrast.

Therefore, the blue narrow band light of 405 to 425 nm and the green narrow band light of 530 to 550 nm enable the superficial blood vessels and the middle-deep blood vessels to be highlighted.

BRIEF SUMMARY OF THE INVENTION

An aspect of an endoscope apparatus according to the present invention comprises an illuminator that includes narrow band light sources and that emits illumination light including rays of narrow band light having different peak wavelengths and different central wavelengths. The narrow band light sources include at least: a first emphasis narrow band light source that emits first emphasis narrow band light whose peak wavelength or central wavelength is included in an emphasis wavelength range, the emphasis wavelength range including at least one of a maximum wavelength that takes at least one maximum value, for an optical absorption spectrum of a diagnosis target substance present in an observation object, and a color-range largest wavelength that takes a color-range largest value that is a largest value of the optical absorption spectrum, in any of three color ranges that are a blue range, a green range, and a red range; and a first non-emphasis narrow band light source that emits first non-emphasis narrow band light whose peak wavelength or central wavelength is included in a non-emphasis wavelength range, the non-emphasis wavelength range being a wavelength range that does not include the emphasis wavelength range of the blue range, green range, and red range. The illuminator further includes a light quantity ratio changing section that changes a first light quantity ratio that is a light quantity ratio between the first emphasis narrow band light and first non-emphasis narrow band light included in the rays of narrow band light.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a schematic structure of an endoscope apparatus according to an embodiment.

FIG. 7 is a table showing how laser light sources to be turned on are combined in each observation mode.

FIG. 27 is a diagram showing still another example of how the illumination light spectrum is in observation mode M1 (superficial blood vessel emphasis mode) according to modification 1.

FIG. 28 is a table showing an example of how laser light source lighting timing/image signal acquisition is according to modification 2.

FIG. 29 is a table showing another example of how laser light source lighting timing/image signal acquisition is according to modification 2.

FIG. 30 is a diagram showing how an optical absorption spectrum of reduced hemoglobin is according to modification 5.

DETAILED DESCRIPTION OF THE INVENTION

Hereinafter, a description will be given of embodiments of the present invention.

Figure 2:
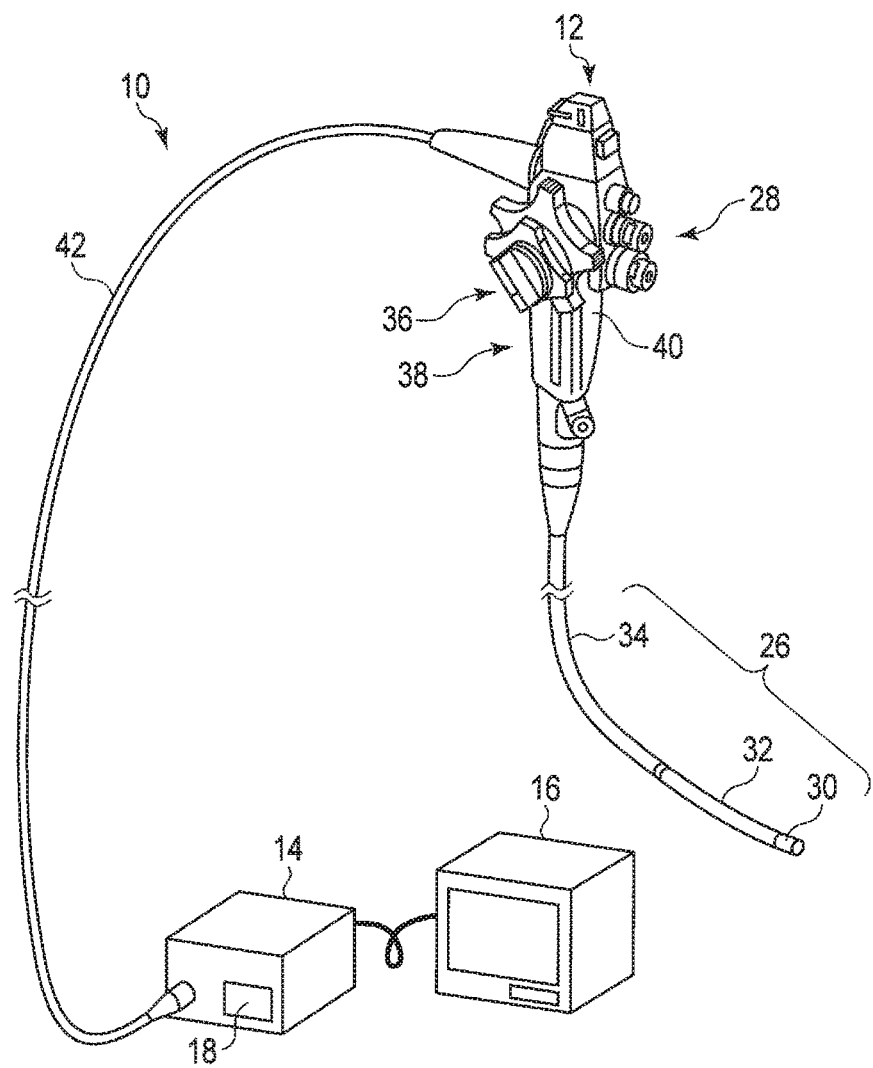
FIG. 2 is an outside diagram showing a schematic structure of the endoscope apparatus.

FIG. 1 and FIG. 2 are diagrams showing a schematic structure of an endoscope apparatus 10 according to an embodiment. In the present specification, the endoscope is not limited to a medical endoscope (an esophagogastroduodenoscope, a colonoscope, an ultrasonic endoscope, a cystoscope, a pyeloscope, a bronchoscope, or the like) or an industrial endoscope, but refers to a general type of apparatus having an insertion section to be inserted into an observation object O.

In the following, a medical endoscope will be described as an example of the endoscope.

The endoscope apparatus 10 according to the present embodiment includes an endoscope 12, a main body (video processor) 14, an image display (monitor) 16, and an input device 18. An illuminator 20 that emits illumination light IL to the observation object O is provided for the endoscope 12 and the main body 14. The observation object O is, for example, an affected portion or a disease portion in a subject (e.g., a body cavity (lumen)).

The endoscope 12 includes an imager 22 that detects reflected and scattered light RL of illumination light radiated to the observation object O and that outputs an imaging signal. The main body 14 includes an image processor 24 that generates an image signal from the imaging signal of the imager 22 of the endoscope 12. The image display 16 is connected to the main body 14 and displays an observation object image formed with the image signal generated by the image processor 24. The input device 18 is connected to the main body 14 or is arranged on the main body 14, and allows various user instructions, such as the designation of an observation mode to be detailed later, to the main body 14 to be entered.

The endoscope 12 has a thin and long insertion section 26, which is a bendable member, and a handling section 28 coupled to the proximal end of the insertion section 26. The endoscope 12 is a tubular insertion apparatus having its tubular insertion section 26 to be inserted into the body cavity.

The insertion section 26 includes, from its distal end to its proximal end, a distal end hard section 30, a bendable section 32, and a flexible tube section 34. The proximal end of the distal end hard section 30 is coupled to the distal end of the bendable section 32, and the proximal end of the bendable section 32 is coupled to the distal end of the flexible tube section 34.

The distal end hard section 30 is a distal end portion of the insertion section 26 and is also a distal end portion of the endoscope 12, and is a hard member. The imager 22 is provided at the distal hard end section 30.

The bendable section 32 can be bent in a desirable direction in accordance with an operation by the user (the operator such as a medical doctor) through a bending operation section 36 provided at the handling section 28.

The user causes the bendable section 32 to be bent by operating the bending operation section 36. The position and direction of the distal end hard section 30 can be changed by a bending operation of the bendable section 32, and the observation object O can be captured within the observation field of view. Illumination light IL is radiated from the illuminator 20 to the captured observation object O, and the observation object O is illuminated. The bendable section 32 is formed of coupling joint rings (not shown) together in the longitudinal direction of the insertion section 26.

The flexible tube section 34 has desirable flexibility and can be bent when an external force is applied thereto. The flexible tube section 34 is a tubular member extended from a main body 38 (described later) of the handling section 28.

The handling section 28 includes the main body (scope) 38, a grip section 40 and a universal cord 42. The flexible tube section 34 extends from the distal end of the main body 38. The grip section 40 is coupled to the proximal end of the main body 38 and is to be held by the user who operates the endoscope 12. The universal cord 42 connects the grip section 40 and the main body 14 to each other.

In the grip section 40, the bending operation section 36 is arranged so that operation wires (not shown) can be operated to bend the bendable section 32. The bending operation section 36 has a right/left bending operation knob that bends the bendable section 32 rightward or leftward, an up/down bending operation knob 37b that bends the bendable section 32 upward or downward, and a fixing knob 37c that fixes the position of the bent bendable section 32.

A rightward/leftward direction bending operation driving section (not shown), which is driven by an operation of the right/left bending operation knob, is connected to the right/left bending operation knob. An upward/downward direction bending operation driving section (not shown), which is driven by an operation of the up/down bending operation knob, is connected to the up/down bending operation knob. The upward/downward direction bending operation driving section and the rightward/leftward direction bending operation driving section are arranged within, for example, the grip section 40.

The rightward/leftward direction bending operation driving section is connected to a single rightward/leftward direction operation wire (not shown) that is inserted through the handling section 28, flexible tube section 34, and bendable section 32, and both ends of the rightward/leftward direction operation wire are connected to the distal end of the bendable section 32.

The upward/downward direction bending operation driving section is connected to a single upward/downward direction operation wire (not shown) that is inserted through the handling section 28, flexible tube section 34 and bendable section 32. The upward/downward direction operation wire and the rightward/leftward direction operation wire are different members and can be operated independently of each other. Both ends of the upward/downward direction operation wire are connected to the distal end of the bendable section 32.

The right/left bending operation knob bends the bendable section 32 in the rightward/leftward direction through the rightward/leftward direction bending operation driving section and the rightward/leftward operation wire. The up/down bending operation knob bends the bendable section 32 in the upward/downward direction through the upward/downward direction bending operation driving section and the upward/downward direction operation wire.

The bending operation section 36 (right/left bending operation knob and the up/down bending operation knob), the rightward/leftward bending operation driving section, the rightward/leftward direction operation wire, the upward/downward direction bending operation driving section, and the upward/downward direction operation wire jointly constitute a bending operation mechanism that operates the bendable section 32 to bend the bendable section 32.

Each of the structural elements will be described in more detail.

<Input Device 18>

The endoscope apparatus 10 according to the present embodiment has the following 17 observation modes in accordance with observation purposes, and the user enters which observation mode should be selected for observation by operating the input device 18. Observation mode information entered through the input device 18 is output to the illuminator 20 and the image processor 24.

The 17 observation modes (observation modes M1 to M17) of the endoscope apparatus 10 are as follows:

Observation mode M1 (superficial blood vessel emphasis mode) is an observation mode in which only blood vessels located in a superficial layer of the observation object O are highlighted.

Observation mode M2 (intermediate blood vessel emphasis mode) is an observation mode in which only blood vessels located in an intermediate layer of the observation object O are highlighted.

Observation mode M3 (deep blood vessel emphasis mode) is an observation mode in which only blood vessels located in a deep layer of the observation object O are highlighted.

Observation mode M4 (superficial and middle-dep blood vessel emphasis mode) is an observation mode in which the blood vessels located in the superficial layer of the observation object O and the blood vessels located in the intermediate layer thereof are highlighted.

Observation mode M5 (superficial and deep blood vessel emphasis mode) is an observation mode in which the blood vessels located in the superficial layer of the observation object O and the blood vessels located in the deep layer thereof are highlighted.

Observation mode M6 (intermediate and deep blood vessel emphasis mode) is an observation mode in which the blood vessels located in the intermediate layer of the observation object O and the blood vessels located in the deep layer thereof are highlighted.

Observation mode M7 (superficial, intermediate, and deep blood vessel emphasis mode) is an observation mode in which the blood vessels located in the superficial layer of the observation object O, the blood vessels located in the intermediate layer thereof, and the blood vessels located in the deep layer thereof are highlighted.

Observation mode M8 (superficial and intermediate blood vessel intermediate-emphasis mode 1) is a blood vessel highlight mode that is intermediate between observation mode M1 (superficial blood vessel emphasis mode) and observation mode M4 (superficial and intermediate blood vessel emphasis mode). In this observation mode M8, the blood vessels located in the superficial layer are emphasized, as in observation mode M1, and the blood vessels located in the intermediate layer are emphasized at an intermediate level between observation mode M1 and observation mode M4.

Observation mode M9 (superficial and intermediate blood vessel intermediate-emphasis mode 2) is a blood vessel highlight mode that is intermediate between observation mode M2 (intermediate blood vessel emphasis mode) and observation mode M4 (superficial and intermediate blood vessel emphasis mode). In this observation mode M9, the blood vessels located in the intermediate layer are emphasized, as in observation mode M2, and the blood vessels located in the superficial layer are emphasized at an intermediate level between observation mode M2 and observation mode M4.

Observation mode M10 (superficial and deep blood vessel intermediate-emphasis mode 1) is a blood vessel highlight mode that is intermediate between observation mode M1 (superficial blood vessel emphasis mode) and observation mode M5 (superficial and deep blood vessel emphasis mode). In this observation mode M10, the blood vessels located in the superficial layer are emphasized, as in observation mode M1, and the blood vessels located in the deep layer are emphasized at an intermediate level between observation mode M1 and observation mode M5.

Observation mode M11 (superficial and deep blood vessel intermediate-emphasis mode 2) is a blood vessel highlight mode that is intermediate between observation mode M3 (deep blood vessel emphasis mode) and observation M5 (superficial and deep blood vessel emphasis mode). In this observation mode M11, the blood vessels located in the deep layer are emphasized, as in observation mode M3, and the blood vessels located in the superficial layer are emphasized at an intermediate level between observation mode M3 and observation mode M5.

Observation mode M12 (intermediate and deep blood vessel intermediate-emphasis mode 1) is a blood vessel highlight mode that is intermediate between observation mode M2 (intermediate blood vessel emphasis mode) and observation mode M6 (intermediate and deep blood vessel emphasis mode). In this observation mode M12, the blood vessels located in the intermediate layer are emphasized, as in observation mode M2, and the blood vessels located in the deep layer are emphasized at an intermediate level between observation mode M2 and observation mode M6.

Observation mode M13 (intermediate and deep blood vessel intermediate-emphasis mode 2) is a blood vessel highlight mode that is intermediate between observation mode M3 (deep blood vessel emphasis mode) and observation mode M6 (intermediate and deep blood vessel emphasis mode). In this observation mode M13, the blood vessels located in the deep layer are emphasized, as in observation mode M3, and the blood vessels located in the intermediate layer are emphasized at an intermediate level between observation mode M3 and observation mode M6.

Observation mode M14 (superficial, intermediate, and deep blood vessel intermediate-emphasis mode 1) is a blood vessel highlight mode that is intermediate between observation mode M1 (superficial blood vessel emphasis mode) and observation mode M7 (superficial, intermediate, and deep blood vessel emphasis mode). In this observation mode M14, the blood vessels located in the superficial layer are emphasized, as in observation mode M1, the blood vessels located in the intermediate layer are emphasized at an intermediate level between observation mode M1 and observation mode M7, and the blood vessels located in the deep layer are emphasized at an intermediate level between observation mode M1 and observation mode M7.

Observation mode M15 (superficial, intermediate, and deep blood vessel intermediate-emphasis mode 2) is a blood vessel highlight mode that is intermediate between observation mode M2 (intermediate blood vessel emphasis mode) and observation mode M7 (superficial, intermediate, and deep blood vessel emphasis mode). In this observation mode M15, the blood vessels located in the intermediate layer are emphasized, as in observation mode M2, the blood vessels located in the superficial layer are emphasized at an intermediate level between observation mode M2 and observation mode M7, and the blood vessels located in the deep layer are emphasized at an intermediate level between observation mode M2 and observation mode M7.

Observation mode M16 (superficial, intermediate, and deep blood vessel intermediate-emphasis mode 3) is a blood vessel highlight mode that is intermediate between observation mode M3 (superficial blood vessel emphasis mode) and observation mode M7 (superficial, intermediate, and deep blood vessel emphasis mode). In this observation mode M16, the blood vessels located in the deep layer are emphasized, as in observation mode M3, the blood vessels located in the superficial layer are emphasized at an intermediate level between observation mode M3 and observation mode M7, and the blood vessels located in the intermediate layer are emphasized at an intermediate level between observation mode M3 and observation mode M7.

Observation mode M17 (normal observation mode) is an observation mode in which illumination light IL having high color rendering property or high color reproduction property is emitted. For example, the normal observation mode is an observation mode in which the color of broadband illumination light IL, such as xenon lamp or halogen lamp, is reproduced. Alternatively, the normal observation mode is an observation mode in which the color of observation object O irradiated with broadband illumination light IL, such as xenon lamp or halogen lamp, is reproduced.

<Illuminator 20>

The illuminator 20 includes laser light sources 44-1 to 44-6 (six laser light sources in the present embodiment), a light source driver 46, six optical fibers 48-1 to 48-6, a light combiner 50, an optical fiber 52, and a light converter 54. The laser light sources 44-1 to 44-6, the light source driver 46, the optical fibers 48-1 to 48-6, the light combiner 50, and part of the optical fiber 52 are arranged inside the main body 14, while the remaining part of the optical fiber 52 and the light converter 54 are arranged inside the endoscope 12.

Laser light source 44-1 (laser 1) is a laser light source (a first emphasis narrow band light source) that has a peak wavelength of 415 nm, and emits first laser light (first emphasis narrow band light).

Laser light source 44-2 (laser 2) is a laser light source (a first non-emphasis narrow band light source) that has a peak wavelength of 445 nm, and emits second laser light (first non-emphasis narrow band light).

Laser light source 44-3 (laser 3) is a laser light source (a second emphasis narrow band light source) that has a peak wavelength of 540 nm, and emits third laser light (second emphasis narrow band light).

Laser light source 44-4 (laser 4) is a laser light source (a second non-emphasis narrow band light source) that has a peak wavelength of 515 nm, and emits fourth laser light (second non-emphasis narrow band light).

Laser light source 44-5 (laser 5) is a laser light source (a third emphasis narrow band light source) that has a peak wavelength of 595 nm, and emits fifth laser light (third non-emphasis narrow band light).

Laser light source 44-6 (laser 6) is a laser light source (a third non-emphasis narrow band light source) that has a peak wavelength of 635 nm, and emits sixth laser light (third non-emphasis narrow band light).

The light source driver 46 controls the driving of these laser light sources 44-1 to 44-6.

The optical fiber 48-1 to 48-6 guide the laser light emitted from the laser light source 44-1 to 44-6 to the light combiner 50.

The light combiner 50 is, for example, an optical fiber combiner, which combines the laser light guided from the laser light sources 44-1 to 44-6 by the optical fibers 48-1 to 48-6.

The optical fiber 52 guides the laser light combined by the light combiner 50 to the light converter 54.

The light converter 54 is disposed in the distal end hard section 30 of the insertion section 26, in which the imager 22 is provided. The light converter 54 converts the optical characteristics of the laser light guided from the main body 14 by the optical fiber 52 inserted through the universal cord 42, handling section 28, and insertion section 26, and radiates the resultant light to the observation object O as illumination light IL.

A more specific description will be given of the structure of each portion of the illuminator 20.

<Laser Light Source 44-1 (Laser 1)>

Figure 3:
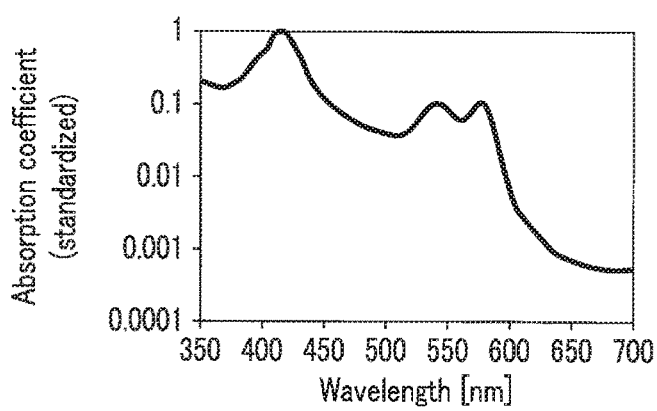
FIG. 3 is a diagram showing an optical absorption spectrum of oxyhemoglobin.

In the present embodiment, oxyhemoglobin contained in the blood in blood vessels is assumed to be the diagnosis target substance present in the observation object O. FIG. 3 shows an optical absorption spectrum of the oxyhemoglobin (hereinafter referred to simply as hemoglobin).

Laser light source 44-1 (laser 1) is a laser light source that has a peak wavelength of 415 nm. The first laser light whose peak wavelength is 415 nm has a reach length up to the superficial region of the observation object O (the definition of the reach length will be mentioned later). The peak wavelength 415 nm of the first laser light is a maximum wavelength that takes a maximum value in the blue range (the definition of a color range will be mentioned later) of the optical absorption spectrum of the hemoglobin, the diagnosis target substance, and much of the first laser light is absorbed in the hemoglobin contained in the blood in the blood vessels in the superficial layer (hereinafter referred to simply as superficial blood vessels). Therefore, where the first laser light is radiated to the observation object O, a large light intensity difference occurs between the light intensity that the reflected and scattered light RL has in the superficial blood vessels and the light intensity that the reflected and scattered light RL has near the superficial blood vessels. In other words, a high contrast is provided for the superficial blood vessels. That is, the superficial blood vessels are emphasized.

Accordingly, the first laser light will be referred to as emphasis narrow band light corresponding to the superficial blood vessels, and laser light source 44-1 (laser 1) will be referred to as an emphasis narrow band light source corresponding to the superficial blood vessels.

The peak wavelength of the first laser light is not limited to 415 nm. The peak wavelength of the first laser light may be another value as long as the peak wavelength or central wavelength is included in the emphasis wavelength range corresponding to the superficial blood vessels.

The emphasis wavelength range corresponding to the superficial blood vessels need not be a wavelength range including a maximum wavelength that takes a maximum value in the blue range of the optical absorption spectrum of the hemoglobin, but may be a wavelength range including a blue-range largest wavelength that takes a largest value in the blue range of the optical absorption spectrum of the hemoglobin.

The emphasis wavelength range corresponding to the superficial blood vessels should preferably be a wavelength range that is within ±20 nm for at least one of the maximum wavelength that takes a maximum value in the blue range of the optical absorption spectrum of the hemoglobin and the blue-range largest wavelength that takes a largest value in the blue range, because light absorption is large and the superficial blood vessels are emphasized. The emphasis wavelength range should more preferably be within ±10 nm, because light absorption is larger and the superficial blood vessels are emphasized more.

The emphasis wavelength range corresponding to the superficial blood vessels should preferably be a wavelength range that has values equal to or more than ½ of the maximum value in the blue range of the absorption spectrum of the hemoglobin or the largest value in the blue range, because the absorption is large.

In the blue range of the optical absorption spectrum of the hemoglobin, the maximum wavelength and the blue-range largest wavelength are equal to each other.

<Laser Light Source 44-2 (Laser 2)>

Laser light source 44-2 (laser 2) is a laser light source that has a peak wavelength of 445 nm. The second laser light whose peak wavelength is 445 nm has, like the first laser, a reach length up to the superficial region of the observation object O. However, the peak wavelength 445 nm of the second laser light is included in the non-emphasis wavelength range corresponding to the superficial blood vessels, which does not include the above-mentioned emphasis wavelength range corresponding to the superficial blood vessels. Where the second laser light is radiated to the observation object O, a small light intensity difference occurs between the light intensity that the reflected and scattered light RL has in the superficial blood vessels and the light intensity that the reflected and scattered light RL has near the superficial blood vessels. In other words, the second laser light provides a low contrast for the superficial blood vessels. That is, the superficial blood vessels are not emphasized.

Accordingly, the second laser light will be referred to as non-emphasis narrow band light corresponding to the superficial blood vessels, and laser light source 44-2 (laser 2) will be referred to as a non-emphasis narrow band light source corresponding to the superficial blood vessels.

The peak wavelength of the second laser light is not limited to 445 nm. The peak wavelength of the second laser light may be another value as long as it is included in the non-emphasis wavelength range in which the superficial blood vessels are not highlighted.

The non-emphasis wavelength range corresponding to the superficial blood vessels is a range that does not include the emphasis wavelength range corresponding to the superficial blood vessels.

The non-emphasis wavelength range corresponding to the superficial blood vessels is preferably a range that includes at least one of a minimum wavelength that takes a minimum value in the blue range of the optical absorption spectrum of the hemoglobin and a blue-range smallest wavelength that takes a smallest value in the blue range of the optical absorption spectrum of the hemoglobin.

The non-emphasis wavelength range corresponding to the superficial blood vessels should preferably be a wavelength range that is within ±20 nm of at least one of the above-mentioned minimum wavelength and smallest wavelength, because light absorption is small and the superficial blood vessels are not emphasized. The non-emphasis wavelength range should more preferably be within ±10 nm, because light absorption is smaller and the superficial blood vessels are suppressed.

The non-emphasis wavelength range corresponding to the superficial blood vessels should preferably be a wavelength range that has values equal to or less than 1.5 times of at least one of the above-mentioned minimum value and smallest value in the blue range, because the absorption is small.

The non-emphasis wavelength range corresponding to the superficial blood vessels should preferably be a wavelength range that has values equal to or less than ½ of at least one of the maximum value in the blue range and the largest value in the blue range, because the absorption is small.

<Laser Light Source 44-3 (Laser 3)>

Laser light source 44-3 (laser 3) is a laser light source that has a peak wavelength of 540 nm. The third laser light whose peak wavelength is 540 nm has a reach length up to the intermediate region of the observation object O, which is deeper than the superficial region. The peak wavelength 540 nm of the third laser light is a maximum wavelength that takes a maximum value in the green range of the optical absorption spectrum of the hemoglobin, and the third laser light is absorbed much in the blood vessels in the intermediate layer. Therefore, where the third laser light is radiated to the observation object O, a large light intensity difference occurs between the light intensity that the reflected and scattered light RL has in the intermediate blood vessels and the light intensity that the reflected and scattered light RL has near the intermediate blood vessels. In other words, a high contrast is provided for the intermediate blood vessels. That is, the intermediate blood vessels are emphasized.

Accordingly, the third laser light will be referred to as emphasis narrow band light corresponding to the intermediate blood vessels, and laser light source 44-3 (laser 3) will be referred to as an emphasis narrow band light source corresponding to the intermediate blood vessels.

The peak wavelength of the third laser light is not limited to 540 nm. The peak wavelength of the third laser light may be another value as long as the peak wavelength or central wavelength is included in the emphasis wavelength range corresponding to the intermediate blood vessels.

The emphasis wavelength range corresponding to the intermediate blood vessels need not be a wavelength range including a maximum wavelength that takes a maximum value in the green range of the optical absorption spectrum of the hemoglobin, but may be a wavelength range including a green-range largest wavelength that takes a largest value in the green range of the optical absorption spectrum of the hemoglobin.

The emphasis wavelength range corresponding to the intermediate blood vessels should preferably be a wavelength range that is within ±20 nm for at least one of the maximum wavelength that takes a maximum value in the green range of the optical absorption spectrum of the hemoglobin and the green-range largest wavelength that takes a largest value in the green range, because light absorption is large and the intermediate blood vessels are emphasized. The emphasis wavelength range should more preferably be within ±10 nm, because light absorption is larger and the intermediate blood vessels are emphasized more.

The emphasis wavelength range corresponding to the intermediate blood vessels should preferably be a wavelength range that has values equal to or more than ½ of the maximum value in the green range of the absorption spectrum of the hemoglobin or the largest value in the green range, because the absorption is large.

<Laser Light Source 44-4 (Laser 4)>

Laser light source 44-4 (laser 4) is a laser light source that has a peak wavelength of 515 nm. The fourth laser light whose peak wavelength is 515 nm has, like the third laser light, a reach length up to the intermediate region of the observation object O. However, the peak wavelength 515 nm of the fourth laser light is included in the non-emphasis wavelength range corresponding to the intermediate blood vessels, which does not include the above-mentioned emphasis wavelength range corresponding to the intermediate blood vessels. Where the fourth laser light is radiated to the observation object O, a small light intensity difference occurs between the light intensity that the reflected and scattered light RL has in the intermediate blood vessels and the light intensity that the reflected and scattered light RL has near the intermediate blood vessels. In other words, the fourth laser light provides a low contrast for the intermediate blood vessels. That is, the intermediate blood vessels are not emphasized.

Accordingly, the fourth laser light will be referred to as non-emphasis narrow band light corresponding to the intermediate blood vessels, and laser light source 44-4 (laser 4) will be referred to as a non-emphasis narrow band light source corresponding to the intermediate blood vessels.

The peak wavelength of the fourth laser light is not limited to 515 nm. The peak wavelength of the fourth laser light may be another value as long as it is included in the non-emphasis wavelength range in which the intermediate blood vessels are not highlighted.

The non-emphasis wavelength range corresponding to the intermediate blood vessels is a range that does not include the emphasis wavelength range corresponding to the intermediate blood vessels.

The non-emphasis wavelength range corresponding to the intermediate blood vessels is preferably a range that includes at least one of a minimum wavelength that takes a minimum value in the green range of the optical absorption spectrum of the hemoglobin and a green-range smallest wavelength that takes a smallest value in the green range of the optical absorption spectrum of the hemoglobin.

The non-emphasis wavelength range corresponding to the intermediate blood vessels should preferably be a wavelength range that is within ±20 nm of at least one of the above-mentioned minimum wavelength and smallest wavelength because light absorption is small and the intermediate blood vessels are not emphasized. The non-emphasis wavelength range should more preferably be within ±10 nm, because light absorption is smaller and the intermediate blood vessels are suppressed.

The non-emphasis wavelength range corresponding to the intermediate blood vessels should preferably be a wavelength range that has values equal to or less than 1.5 times of at least one of the above-mentioned minimum value and smallest value in the green range, because light absorption is small.

Alternatively, the non-emphasis wavelength range corresponding to the intermediate blood vessels should preferably be a wavelength range that has values equal to or less than ½ of at least one of the maximum value in the green range and the largest value in the green range, because the absorption is small.

<Laser Light Source 44-5 (Laser 5)>

Laser light source 44-5 (laser 5) is a laser light source that has a peak wavelength of 595 nm. The fifth laser light whose peak wavelength is 595 nm has a reach length up to a deep region of the observation object O, which is deeper than the intermediate region. The peak wavelength 595 nm of the fifth laser light is included in the emphasis wavelength range corresponding to the deep blood vessels, i.e., a wavelength range that is within ±20 nm of the red-range largest wavelength 590 nm that takes a largest value in the red range of the optical absorption spectrum of the hemoglobin, and that has values equal to or more than ½ of the red-range largest value, and the absorption in the deep blood vessels is large. Therefore, where the fifth laser light is radiated to the observation object O, a large light intensity difference occurs between the light intensity that the reflected and scattered light RL has in the deep blood vessels and the light intensity that the reflected and scattered light RL has near the deep blood vessels. In other words, a high contrast is provided for the deep blood vessels. That is, the deep blood vessels are emphasized.

Accordingly, the fifth laser light will be referred to as emphasis narrow band light corresponding to the deep blood vessels, and laser light source 44-5 (laser 5) will be referred to as an emphasis narrow band light source corresponding to the deep blood vessels.

The peak wavelength of the fifth laser light is not limited to 595 nm. The peak wavelength of the fifth laser light may be another value as long as the peak wavelength or central wavelength is included in the emphasis wavelength range corresponding to the deep blood vessels.

The emphasis wavelength range corresponding to the deep blood vessels need not be a wavelength range including a maximum wavelength that takes a maximum value in the red range of the optical absorption spectrum of the hemoglobin, but may be a wavelength range including a red-range largest wavelength that takes a largest value in the red range of the optical absorption spectrum of the hemoglobin.

The emphasis wavelength range corresponding to the deep blood vessels should preferably be a wavelength range that is within ±20 nm of at least one of the maximum wavelength that takes a maximum value in the red range of the optical absorption spectrum of the hemoglobin and the red-range largest wavelength that takes a largest value in the red range, because light absorption is large and the deep blood vessels are emphasized. The emphasis wavelength range should more preferably be within ±10 nm, because light absorption is larger and the deep blood vessels are emphasized more.

The emphasis wavelength range corresponding to the deep blood vessels should preferably be a wavelength range that has values equal to or more than ½ of the maximum value in the red range of the absorption spectrum of the hemoglobin or the largest value in the red range, because the absorption is large.

<Laser Light Source 44-6 (Laser 6)>

Laser light source 44-6 (laser 6) is a laser light source that has a peak wavelength of 635 nm. The sixth laser light whose peak wavelength is 635 nm has, like the fifth laser light, a reach length up to the deep region of the observation object O. However, the peak wavelength 635 nm of the sixth laser light is included in the non-emphasis wavelength range corresponding to the deep blood vessels, which does not include the above-mentioned emphasis wavelength range corresponding to the deep blood vessels. Where the sixth laser light is radiated to the observation object O, a small light intensity difference occurs between the light intensity that the reflected and scattered light RL has in the deep blood vessels and the light intensity that the reflected and scattered light RL has near the deep blood vessels. In other words, a low contrast is provided for the deep blood vessels. That is, the deep blood vessels are not emphasized.

Accordingly, the sixth laser light will be referred to as non-emphasis narrow band light corresponding to the deep blood vessels, and laser light source 44-6 (laser 6) will be referred to as a non-emphasis narrow band light source corresponding to the deep blood vessels.

The peak wavelength of the sixth laser light is not limited to 635 nm. The peak wavelength of the sixth laser light may be another value as long as it is included in the non-emphasis wavelength range in which the deep blood vessels are not highlighted.

The non-emphasis wavelength range corresponding to the deep blood vessels is a range that does not include the emphasis wavelength range corresponding to the deep blood vessels.

The non-emphasis wavelength range corresponding to the deep blood vessels is preferably a range that includes at least one of a minimum wavelength that takes a minimum value in the red range of the optical absorption spectrum of the hemoglobin and a red-range smallest wavelength that takes a smallest value in the red range of the optical absorption spectrum of the hemoglobin.

The non-emphasis wavelength range corresponding to the deep blood vessels should preferably be a wavelength range that is within ±20 nm of at least one of the above-mentioned minimum wavelength and smallest wavelength, because light absorption is small and the deep blood vessels are not emphasized. The non-emphasis wavelength range should more preferably be within ±10 nm, because light absorption is smaller and the deep blood vessels are suppressed.

The non-emphasis wavelength range corresponding to the deep blood vessels should preferably be a wavelength range that has values equal to or less than 1.5 times of at least one of the above-mentioned minimum value and smallest value in the red range, because light absorption is small.

Alternatively, the non-emphasis wavelength range corresponding to the deep blood vessels should preferably be a wavelength range that has values equal to or less than ½ of at least one of the maximum value in the red range and the largest value in the red range, because the absorption is small.

It should be noted the narrow band light mentioned above, i.e., the emphasis narrow band light and the non-emphasis narrow band light, may be light other than laser light. The narrow band light should preferably be light having a wavelength width of 50 nm or less, more preferably light having a wavelength width of 5 nm or less. The wavelength width is, for example, a wavelength width defined by the full width at half maximum (FWHM) or the root mean square (RMS). The wavelength width of half-value-width laser light is, for example, 1 nm. A light source may be, for example, an LED or a light source using fluorescent light exited by LED light or laser light; alternatively, the light source may generate narrow band light from broadband light using spectral filters. In a structure that uses the spectral filters to generate narrow band light, wavelengths of radiated narrow band light are switched from one to another by mechanically switching the spectral filters.

<Color Ranges>

The blue range, green range, and red range mentioned above are defined by the following wavelength ranges:

Blue Range: 400 to 510 nm
Green Range: 490 to 610 nm
Red Range: 590 to 700 nm

These wavelength ranges are wavelength ranges obtained by dividing a wavelength range from 400 to 700 nm of the visible light range equally into three ranges and providing an overlap of 20 nm between the adjacent ranges. Where wavelengths are set based on these well-balanced wavelength ranges and light have wavelengths that are within the respective color ranges of the blue range, green range, and red range, illumination light IL having good color reproduction property can be generated.

For example, a wavelength range that is less than 400 nm and a wavelength range that is 700 nm or more may be allocated to the blue range and the red range, respectively. In this case, the blue range, green range, and red range are defined by the following wavelength ranges:

Blue Range: 380 to 510 nm
Green Range: 490 to 610 nm
Red Range: 590 to 780 nm

Figure 4:
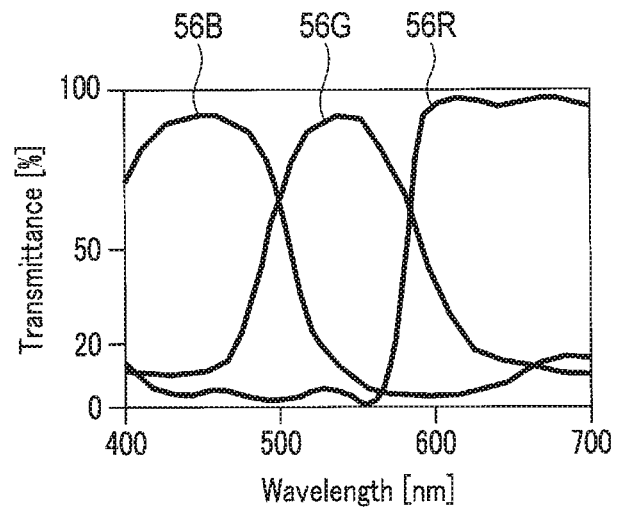
FIG. 4 is a diagram showing an example of spectroscopic characteristics of color filters of an imager.

For example, when the imager 22 acquires a spectral image, using the color filters, the blue range, green range, and red range may be defined using the spectroscopic characteristics of the color filters. FIG. 4 shows an example of the spectroscopic characteristics 56B of the blue (B) color filter, the spectroscopic characteristics 56G of the green (G) color filter, and the spectroscopic characteristics 56R of the red (B) color filter. Let us assume that a wavelength range having a transmittance of 20% or more is defined as the color range of each color filter. As shown in FIG. 4, the blue range is 400 to 525 nm, the green range is 470 to 625 nm, and the red range is 570 to 700 nm.

As shown in FIG. 4, there is hardly any wavelength range in which the transmittance of the color filters is zero, and the transmittance is several % to 10% or so in a broad range of the visible light. The transmittance of several % to 10% or so can be regarded as a negligible level in capturing a color image, so that color ranges should be preferably defined based on the range in which the transmittance is 20% or higher.

<Maximum Value and Color-Range Largest Value in Each Color Range>

Figure 5:
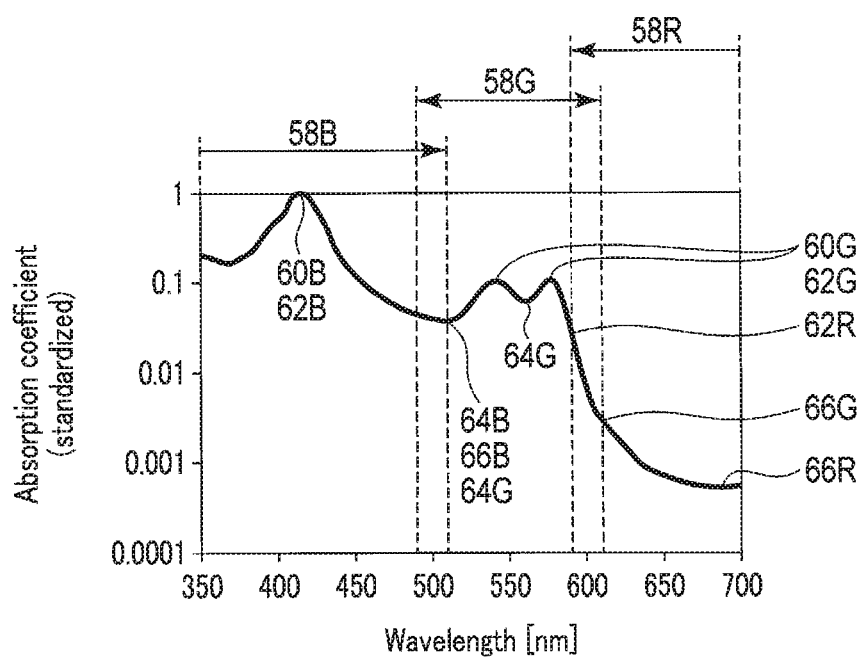
FIG. 5 is a diagram showing how a maximum value and a color-range largest value are in each color range.

How a maximum value and a color-range largest value for the absorption spectrum of oxyhemoglobin are in each color range is shown in FIG. 5.

In the blue range 58B, the maximum wavelength that takes the blue-range maximum value 60B and the color-range largest wavelength that takes the blue-range largest value 62B are the same wavelength 415 nm, and the minimum wavelength that takes the blue-range minimum value 64B and the color-range smallest wavelength that takes the blue-range smallest value 66B are the same wavelength 500 nm.

In contrast, in the green range 58G, the maximum wavelength that takes the green-range maximum value 60G and the color-range largest wavelength that takes the green-range largest value 62G are the same wavelength, but this wavelength appears at two points, i.e., at 540 nm and approximately 575 nm. The minimum wavelength that takes the green-range minimum value 64G also appears at two points, i.e., at 500 nm and 560 nm. The color-range minimum wavelength that takes the green-range smallest value 66G is wavelength 610 nm.

In the red range 58R, neither a maximum value nor a minimum value exists, the color-range largest wavelength that takes the red-range largest value 62R is wavelength 590 nm, and the color-range smallest wavelength that takes the red-range smallest value 66R is wavelength 685 nm.

<Reach Length>

Where light of a wavelength range from near ultraviolet to near infrared is radiated to a living body (observation object O), light having a longer wavelength travels deeper into the living body, due to the light scattering property and light absorption property in living tissues (an epithelial tissue, a mucous membrane, a body fluid, etc.).

Figure 6A:
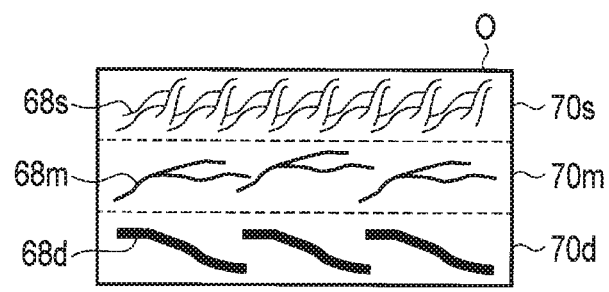
FIG. 6A is a diagram schematically showing a laminated structure of blood vessels.

For example, as shown in FIG. 6A, the blood vessels of a living body (observation object O) include superficial blood vessels (capillaries) 68s located near the surface of the living body, intermediate blood vessels (blood vessels thicker than the capillaries) 68m located in deeper portions, and deep blood vessels (blood vessels thicker than the intermediate blood vessels) 68d located in further deeper portions. The region where the superficial blood vessels 68s exist will be referred to as a superficial region 70s of the living body, the region where the intermediate blood vessels 68m exist will be referred to as a intermediate region 70m, and the region where the deep blood vessels 68d exist will be referred to as a deep region 70d.

Figure 6B:
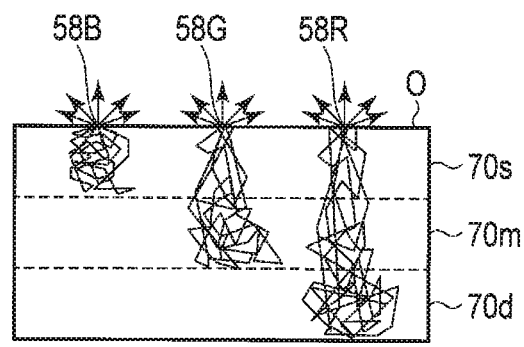
FIG. 6B is a diagram schematically showing how the reach length of light is in each color range.

As shown in FIG. 6B, where light of the blue range 58B on the short wavelength side is radiated to the living body (observation object O), the light of the blue range 58B has a reach length up to the superficial region 70s of the living body, is greatly influenced by the absorption by the superficial blood vessels 68s, and the results are reflected in an image of the living body (observation object O). Where light of the green range 58G is radiated, the light of the green range 58G has a reach length up to the intermediate region 70m of the living body, is greatly influenced by the absorption by the intermediate blood vessels 68m, and the results are reflected in an image of the living body (observation object O). Where light of the red range 58R is radiated, the light of the red range 58R has a reach length up to the deep region 70d of the living body, is greatly influenced by the absorption by the deep blood vessels 68d, and the results are reflected in an image of the living body (observation object O).

For example, the reach length is defined as follows:

Light intensity $I(x)$ at distance $x$ within a living body (observation object O) is expressed by
$I(x)=I_0\exp[-\alpha x]$, where $I_0$ is an incident light intensity and $\alpha$ is an attenuation coefficient.

The reach length is defined as the reciprocal of attenuation coefficient $\alpha$, i.e., a distance at which the light intensity becomes equal to 1/e. Provided that $\mu_a$ is an absorption coefficient, $\mu_s$ is a scattering coefficient, g is an anisotropy factor, and an equivalent scattering coefficient is given by $\mu_s'=(1-g)\mu_s$, attenuation coefficient $\alpha$ is defined by equation (1) set forth below.

$$\alpha=\sqrt{(3\mu_a(\mu_a+\mu_s'))} \quad (1)$$

For example, absorption coefficient μa, scattering coefficient μs, and equivalent scattering coefficient μs' may be merely used as attenuation coefficient $\alpha$.

Absorption coefficient $\mu_a$, scattering coefficient $\mu_s$, and anisotropy factor g differ, depending upon the living body (observation object O) and the wavelength.

<Optical Fibers 48-1 to 48-6 and 52>

The optical fibers 48-1 to 48-6 and the optical fiber 52 are single-wire fibers having a core diameter of, for example several tens of μm to several hundreds of μm. An optical coupling lens (not shown in the drawings) is disposed between each of the laser light sources 44-1 to 44-6 and the optical fibers 48-1 to 48-6 to converge the laser light emitted from the laser sources and couple it to the optical fibers.

In place of the optical fiber 52, a bundle fiber made of a bundle of optical fibers may be used.

<Light Source Driver 46>

The light source driver 46 is capable of controlling the ON/OFF, driving current, and driving method (continuous wave oscillation (CW), pulse driving, etc.) of each of the laser light sources independently.

The light source driver 46 controls a combination of the laser light sources 44-1 to 44-6 to be turned on, in accordance with observation mode information supplied from the input device 18.

The light source driver 46 comprises a light quantity ratio changing section 72 and a storage 74.

The light quantity ratio changing section 72 changes a first light quantity ratio, a second light quantity ratio, and a third light quantity ratio, in accordance with observation mode information entered through the input device 18.

The first light quantity ratio is a ratio between the light quantity of the first laser light (first emphasis narrow band light) emitted from laser light source 44-1 (laser 1) and the light quantity of the second laser light (first non-emphasis narrow band light) emitted from laser light source 44-2 (laser 2).

The second light quantity ratio is a ratio between the light quantity of the third laser light (second emphasis narrow band light) emitted from laser light source 44-3 (laser 3) and the light quantity of the fourth laser light (second non-emphasis narrow band light) emitted from laser light source 44-4 (laser 4).

The third light quantity ratio is a ratio between the light quantity of the fifth laser light (third emphasis narrow band light) emitted from laser light source 44-5 (laser 5) and the light quantity of the sixth laser light (third non-emphasis narrow band light) emitted from laser light source 44-6 (laser 6).

In other words, the light quantity ratio changing section 72 switches observation modes by changing the first light quantity ratio, the second light quantity ratio, and the third light quantity ratio.

For example, the second light quantity ratio of observation mode M8 (superficial and intermediate blood vessel intermediate-emphasis mode 1) is a light quantity ratio (e.g., 0.5:0.5) that is intermediate between the second light quantity ratio (0:1) of observation mode M1 (superficial blood vessel emphasis mode) and the second light quantity ratio (1:0) of observation mode M4 (superficial and intermediate blood vessel emphasis mode). The first light quantity ratio of observation mode M9 (superficial and intermediate blood vessel intermediate-emphasis mode 2) is a light quantity ratio (e.g., 0.5:0.5) that is intermediate between the first light quantity ratio (0:1) of observation mode M2 (intermediate blood vessel emphasis mode) and the first light quantity ratio (1:0) of observation mode M4 (superficial and intermediate blood vessel emphasis mode). The light quantity ratios of the other observation modes will be described later.

The storage 74 stores combinations of laser light sources to be turned on in each observation mode and a current value or a voltage value to be applied to each laser light source. That is, the storage 74 stores combinations of the laser light sources to be turned on in the observation modes shown in FIG. 7.

The light source driver 46 not only changes the first to third light quantity ratios in accordance with observation mode information entered through the input device 18 but also may continuously change and adjust the first to third light quantity ratios from a certain observation mode. In this case, the configuration of the endoscope apparatus 10 may be modified such that the input device 18 has a function of supplying user instructions for changing and adjusting the first to third light quantity ratios to the main body 14.

The light source driver 46 may be constituted by a processor. In this case, the storage 74 may be a built-in memory of the processor, or may be an external memory accessible by the processor. The external memory has stored a program code that causes the processor to function as the light source driver 46 when executed by the processor.

Details of the combinations of laser light sources to be turned on in each observation mode and the combinations of rays of laser light to be emitted in each observation mode will be mentioned later.

<Light Converter 54>

Figure 8:
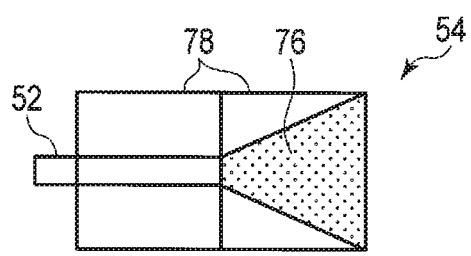
FIG. 8 is a schematic diagram showing a light converter.

As shown in FIG. 8, the light converter 54 includes a diffusing member 76 located at the distal end of the optical fiber 52 and formed of alumina particles or the like. The distal end of the optical fiber 52 and the diffusing member 76 are held by a holder 78, and the positional relation between them is defined.

The diffusing member 76 has a function of diffusing laser light guided by the optical fiber 52 and changing it to light having a desirable light distribution. The diffusing member 76 does not convert the wavelengths of the light.

In place of the diffusing member 76, the light converter 54 may employ a lens or a combination of the lens and the diffusing member 76.

Where a bundle fiber is employed in place of the optical fiber 52, the light converter 54 may employ a lens in place of the diffusing member 76.

<Imager 22>

The imager 22 detects reflected and scattered light RL from the observation object O to generate an imaging signal. The imaging signal is output to the image processor 24 of the main body 14.

Although not shown in the drawings, the imager 22 includes three type of light detection elements, which are an R light detection element to detect the red range 58R, a G light detection element to detect the green range 58G, and a B light detection element to detect the blue range 58B. Examples of the spectroscopic characteristics of the color filters of the R light detection element, G light detection element and B light detection element are shown in FIG. 4.

By means of the R light detection element, G light detection element, and B light detection element, the imager 22 generates an R imaging signal, a G imaging signal, and a B imaging signal for the red range 58R, the green range 58G, and the blue range 58B, separately and independently.

The imager 22 is specifically a CCD imager or a CMOS imager.

The imager 22 may be a monochromatic imager having no color filter. In this case, the imager sequentially receives reflected and scattered light RL of laser light sequentially emitted at different timings, so as to generate imaging signals therefrom, and the image processor 24 performs RGB assignment processing.

<Image Processor 24 and Image Display 16>

The image processor 24 performs image processing for the B imaging signal, G imaging signal, and R imaging signal output from the imager 22 in accordance with observation mode information, so as to generate image signals constituting an observation object image.

The image processor 24 may be constituted by a processor. In this case, an external memory accessible by the processor has stored a program code that causes the processor to function as the image processor 24 when executed by the processor.

Where the imager 22 is a monochromatic imager having no color filter, RGB assignment processing is first performed for imaging signals sequentially generated at different timings, and then image signals are generated.

The image display 16 displays an observation object image in accordance with image signals generated by the image processor 24. The image display 16 is, for example, a monitor such as a liquid crystal display.

An operation of the endoscope apparatus 10 having the above structure will be described.

Figure 9:
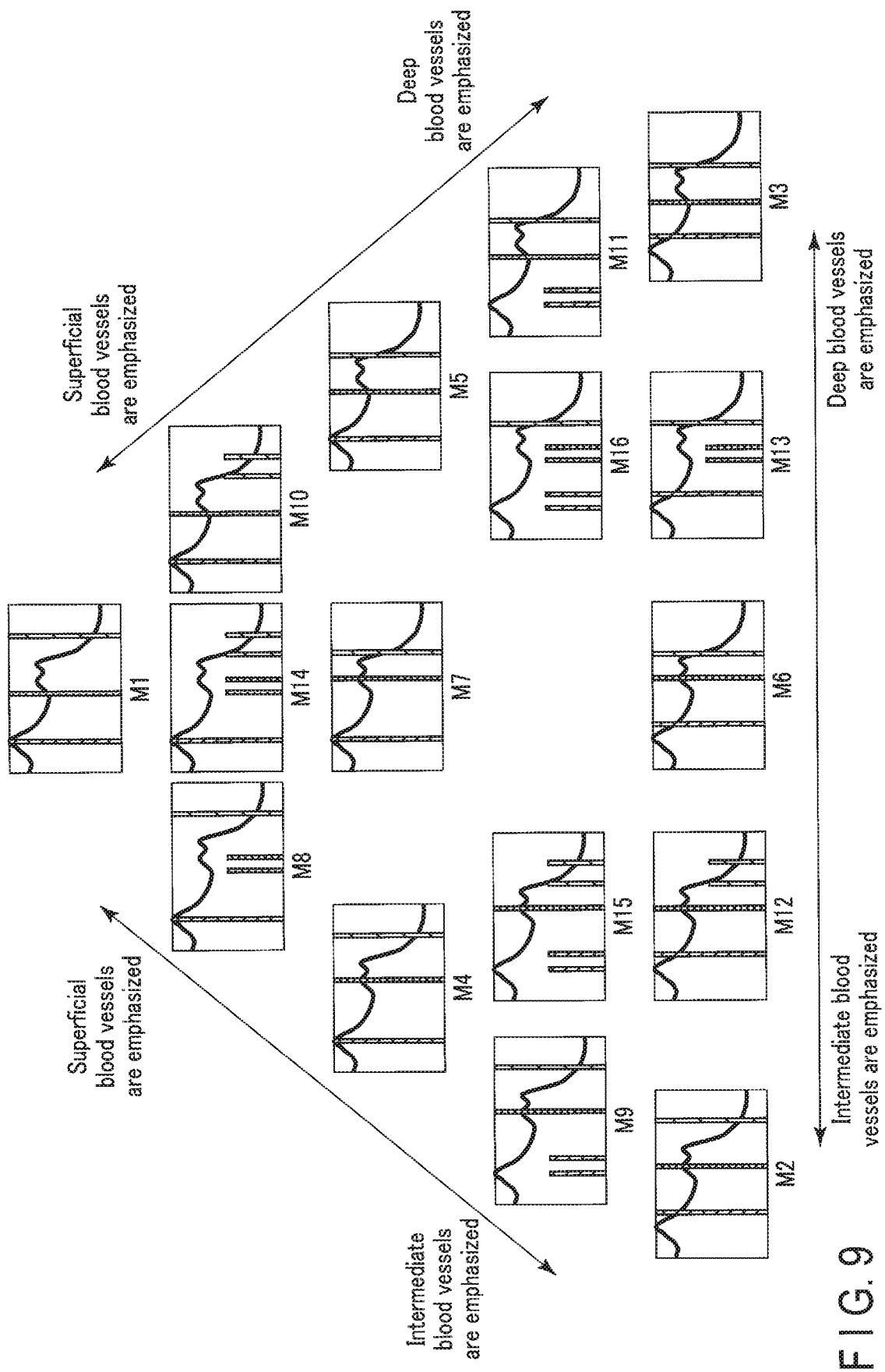
FIG. 9 is a diagram showing how illumination light spectra are in observation modes M1 to M16.
Figure 10:
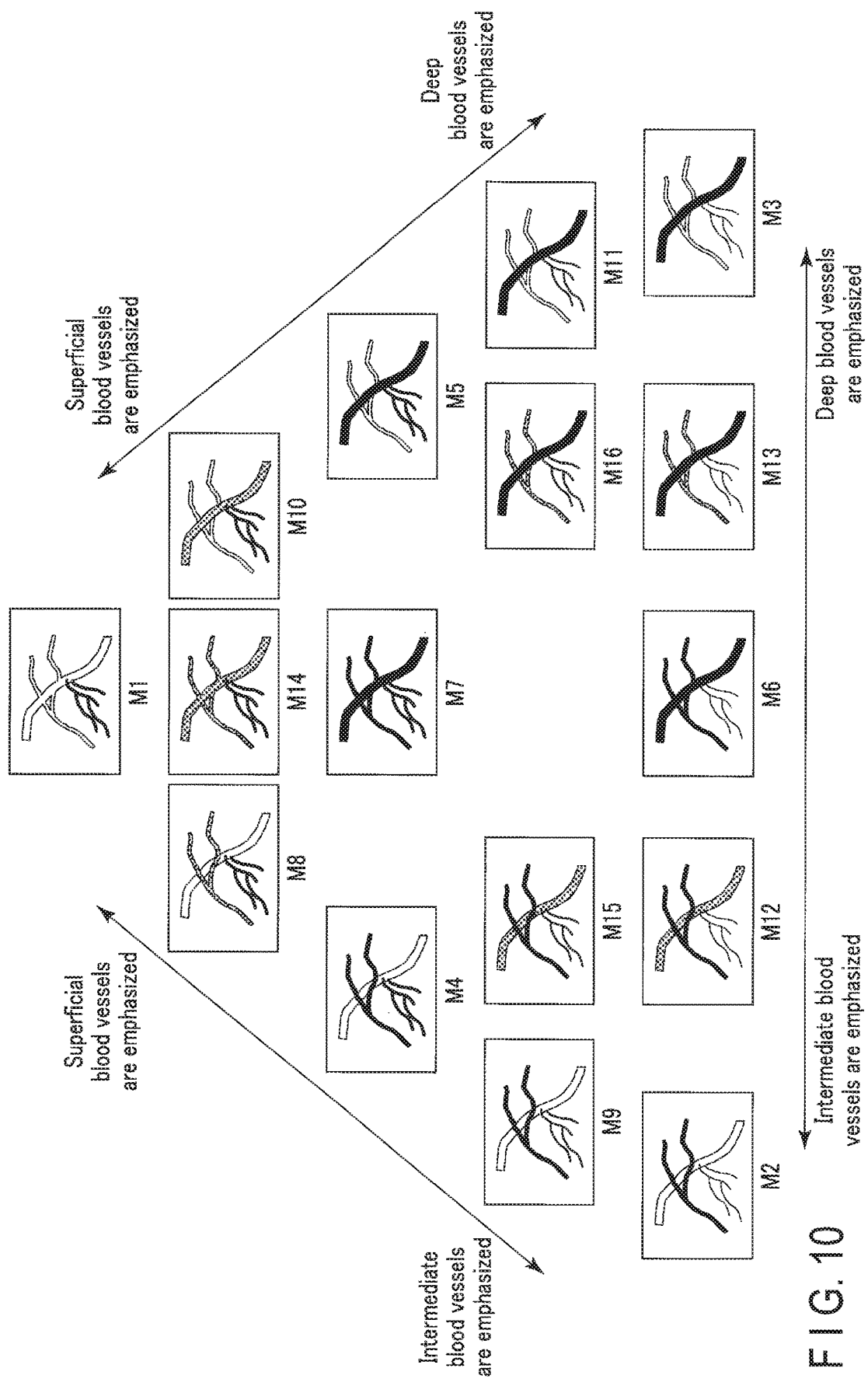
FIG. 10 is a diagram showing observation object images displayed in observation modes M1 to M16.

As described above, the light source driver 46 controls combinations of the laser light sources 44-1 to 44-6 to be turned on, as shown in FIG. 9, in accordance with observation mode information supplied from the input device 18 and indicating an observation mode entered by the user. Owing to this, the image display 16 displays an observation object image in each observation mode, as shown in FIG. 10.

In FIG. 9, the ordinate axis of each laser light spectrum is drawn in an arbitrary scale. In FIG. 9 and FIG. 10, the blood vessel emphasis modes of observation modes M1 to M16 are shown, and the normal observation mode of observation mode M17 is not shown.

Each of the observation modes will be described in detail.

<Observation Mode M1 (Superficial Blood Vessel Emphasis Mode)>

Where the user enters observation mode M1 (superficial blood vessel emphasis mode) from the input device 18 as an observation mode, the input device 18 outputs observation mode information on observation mode M1 (superficial blood vessel emphasis mode) to the light source driver 46 and the image processor 24.

Figure 11:
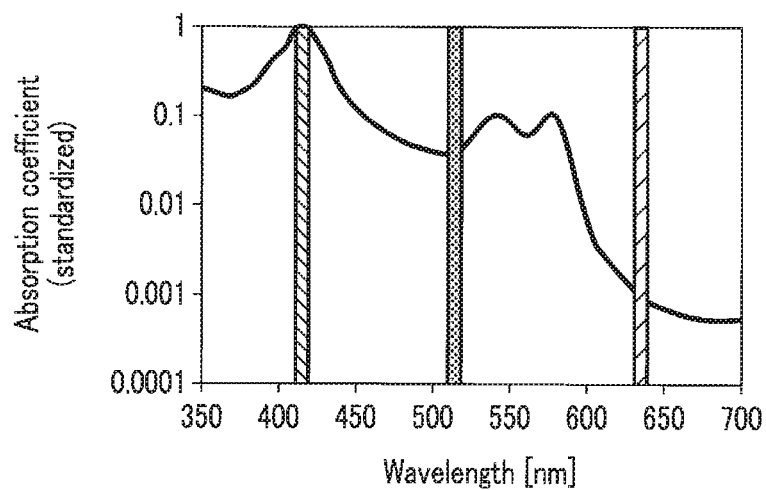
FIG. 11 is a diagram showing how an illumination light spectrum is in observation mode M1 (superficial blood vessel emphasis mode).

Upon receipt of the observation mode information on observation mode M1 (superficial blood vessel emphasis mode), the light source driver 46 turns on laser light source 44-1 (laser 1), laser light source 44-4 (laser 4), and laser light source 44-6 (laser 6), so as to cause the laser light sources 44-1, 44-4, and 44-6 to emit first laser light, fourth laser light, and sixth laser light, as shown in FIG. 7, FIG. 9, and FIG. 11.

That is, the light quantity ratio changing section 72 of the light source driver 46 changes the first to third light quantity ratios, as follows:

light quantity ratio (first light quantity ratio) between first laser light and second laser light=1:0 light quantity ratio (second light quantity ratio) between third laser light and fourth laser light=0:1 light quantity ratio (third light quantity ratio) between fifth laser light and sixth laser light=0:1

Laser light source 44-1 (laser 1) is an emphasis narrow band light source corresponding to the superficial blood vessels 68*s* (superficial region 70*s*), and the first laser light emitted from laser light source 44-1 (laser 1) is emphasis narrow band light corresponding to the superficial blood vessels 68*s* (superficial region 70*s*). The wavelength of the first laser light, the emphasis narrow band light corresponding to the superficial blood vessels 68*s*, is 415 nm and is included in the blue range 58B, as shown in FIG. 9 and FIG. 11. In FIG. 11, the ordinate axis of the laser light spectrum is drawn in an arbitrary scale.

Laser light source 44-4 (laser 4) is a non-emphasis narrow band light source corresponding to the intermediate blood vessels 68*m* (intermediate region 70*m*), and the fourth laser light emitted from laser light source 44-4 (laser 4) is non-emphasis narrow band light corresponding to the intermediate blood vessels 68*m* (intermediate region 70*m*). The wavelength of the fourth laser light, the non-emphasis narrow band light corresponding to the intermediate blood vessels 68*m*, is 515 nm and is included in the green range 58G, as shown in FIG. 9 and FIG. 11.

Laser light source 44-6 (laser 6) is a non-emphasis narrow band light source corresponding to the deep blood vessels 68*d* (deep region 70*d*), and the sixth laser light emitted from laser light source 44-6 (laser 6) is non-emphasis narrow band light corresponding to the deep blood vessels 68*d* (deep region 70*d*). The wavelength of the sixth laser light, the non-emphasis narrow band light corresponding to the deep blood vessels 68*d*, is 635 nm and is included in the red range 58R, as shown in FIG. 9 and FIG. 11.

After being guided by the optical fibers 48-1, 48-4, and 48-6, the first laser light, fourth laser light, and sixth laser light are combined together by the light combiner 50.

The combined first laser light, fourth laser light, and sixth laser light are converted into light having a desirable light distribution by the light converter 54 at the distal end of the insertion section 26, and the resultant light is radiated to the observation object O as illumination light IL.

The first laser light whose wavelength is included in the blue range 58B has a reach length up to the superficial region 70*s*. Where the first laser light is radiated to the observation object O, a large light intensity difference occurs between the light intensity that the reflected and scattered light RL has in the superficial blood vessels and the light intensity that the reflected and scattered light RL has near the superficial blood vessels. In other words, a high contrast is provided for the superficial blood vessels 68*s*. That is, the superficial blood vessels 68*s* are emphasized.

The reflected and scattered light RL of the illumination light IL in the observation object O is detected by the imager 22. In the imager 22, the B light detection element detects the reflected and scattered light RL of the first laser light whose wavelength is included in the blue range 58B, and generates a B imaging signal. The B imaging signal is output to the image processor 24. The image processor 24 performs image processing for the B imaging signal output from the imager 22 in accordance with observation mode information, and generates a B image signal.

The fourth laser light whose wavelength is included in the green range 58G has a reach length up to the intermediate region 70*m*. Where the fourth laser light is radiated to the observation object O, a small light intensity difference occurs between the light intensity that the reflected and scattered light RL has in the intermediate blood vessels 68*m* and the light intensity that the reflected and scattered light RL has near the intermediate blood vessels 68*m*. In other words, a low contrast is provided for the intermediate blood vessels 68*m*. That is, the intermediate blood vessels 68*m* are not emphasized.

In the imager 22, the G light detection element detects the reflected and scattered light RL of the fourth laser light whose wavelength is included in the green range 58G, and generates a G imaging signal. The G imaging signal is output to the image processor 24. The image processor 24 performs image processing for the G imaging signal output from the imager 22 in accordance with observation mode information, and generates a G image signal.

The sixth laser light whose wavelength is included in the red range 58R has a reach length up to the deep region 70*d*. Where the sixth laser light is radiated to the observation object O, a small light intensity difference occurs between the light intensity that the reflected and scattered light RL has in the deep blood vessels 68*d* and the light intensity that the reflected and scattered light RL has near the deep blood vessels 68*d*. In other words, a low contrast is provided for the deep blood vessels 68*d*. That is, the deep blood vessels 68*d* are not emphasized.

In the imager 22, the R light detection element detects the reflected and scattered light RL of the sixth laser light whose wavelength is included in the red range 58R, and generates an R imaging signal. The R imaging signal is output to the image processor 24. The image processor 24 performs image processing for the R imaging signal output from the imager 22 in accordance with observation mode information, and generates an R image signal.

That is, the light intensity that the reflected and scattered light RL of the illumination light IL has in the superficial blood vessels 68*s* is more different from the light intensity that the reflected and scattered light RL has near the blood vessels (in the mucous membrane or the like), than the light intensity that the reflected and scattered light RL has in the intermediate blood vessels 68*m* and the deep blood vessels 68*d*.

In the illumination light IL in observation mode M1 (superficial blood vessel emphasis mode), the superficial region 70*s* is an attention depth region, and the intermediate region 70*m* and the deep region 70*d* are non-attention depth regions.

This observation mode is effective in observing the superficial blood vessels 68*s* in detail.

In the illumination light IL, emphasis narrow band light is included in any one color range of the three color ranges. Owing to this, only the superficial layer, or as will be described below, either the intermediate layer or the deep layer can be emphasized. It should be noted that "any one color range" does not exclude a color overlap range that overlaps another color range. The color range is a single-color range including the color overlap range.

The illumination light IL includes single emphasis narrow band light. Non-emphasis narrow band light of the illumination light IL is not included in the color range that includes the emphasis narrow band light. Owing to this, the blood vessels located in an attention depth region can be emphasized. This is because, if different emphasis narrow band light exist in the attention depth region or if emphasis narrow band light mixes with non-emphasis narrow band light, the blood vessel contrast in the attention depth may decrease.

The first laser light (emphasis narrow band light), the fourth laser light (non-emphasis narrow band light) and the sixth laser light (non-emphasis narrow band light) may be simultaneously turned on to irradiate the observation object O; alternatively, they may be turned on sequentially at different timings to irradiate the observation object O sequentially. In particular, where the imager 22 is a monochromatic imager having no color filter, they have to be sequentially turned on at different timings to irradiate the observation object O sequentially.

Emphasis narrow band light and non-emphasis narrow band light (the fourth laser light in this case) that is included in the color range (the green range 58G in this case) adjacent to the color range including the emphasis narrow band light should preferably be emitted sequentially at different timings, and the imager 22 should preferably separate light into a B imaging signal and a G imaging signal. In many cases, the color filters of the imager 22 have sensitivity to adjacent color ranges. In this case, an imaging signal (the B imaging signal in this case) including the emphasis narrow band light may also include non-emphasis narrow band light (the fourth laser light in this case), lowering the blood vessel contrast in the attention depth.

The intensity ratio among the first laser light, fourth laser light, and sixth laser light is determined such that the mixed light of the first, fourth, and sixth laser light is white light. White light is light in which the color of broadband illumination light IL, such as xenon lamp or halogen lamp, is reproduced. Alternatively, white light is light in which the color of observation object O irradiated with broadband illumination light IL, such as xenon lamp or halogen lamp, is reproduced. More specifically, white light is defined using, for example, chromaticity coordinates, a correlated color temperature, or a color difference from a black body locus. For example, it is defined as, in the chromaticity coordinates, a color within the ranges (x=0.2-0.4, y=0.2-0.4), (x=0.4-0.5, y=0.35-0.45) is defined, in the correlated color temperature, a color of the range from 2000 to 100000K, or in the black body locus, a color of the range in which the color difference (duv) from the black body locus is ±0.1 or less. White light may be defined in consideration of the spectral sensitivity of an imaging element. For example, white light may be defined as above, using the chromaticity coordinates or correlated color temperature calculated for the spectrum obtained by multiplying the spectrum of illumination light IL with the spectral sensitivity of the imaging element.

It may be set to have a color other than the white color in accordance with the purpose of use. In this case as well, the color is defined using the chromaticity coordinates or the like.

The two rays of non-emphasis narrow band light of the illumination light IL are respectively included in the two color ranges (the green range 58G and red range 58R in this case) that do not include the emphasis narrow band light. The two rays of non-emphasis narrow band light are included in the narrow band ranges constituting the illumination light IL so as to enhance the color reproduction property of the illumination light IL. In order to enhance the color reproduction property of the illumination light IL, it is desirable that non-emphasis narrow band light is included in, of the three color ranges, all color ranges that do not include the emphasis narrow band light, but it is only required that at least one non-emphasis narrow band light is included in a color range that does not include the emphasis narrow band light (for example, only the first laser light and fourth laser light, or only the first laser and sixth laser light). Owing to this, the color reproduction property of the illumination light IL is enhanced. Further, either the emphasis narrow band light or the non-emphasis narrow band light should preferably be included in each of the three color ranges, in order to enhance the color reproduction property.

The image processor 24 performs at least one of the contrast emphasis image process, outline (edge) emphasis image process, and blood vessel structure emphasis image process for the imaging signal that is one of the B imaging signal, G imaging signal, and R imaging signal and that corresponds to the color range including the emphasis narrow band light.

The three image processes are known image processes per se.

That is, the contrast emphasis image process is an image process in which the image brightness difference (contrast) is increased.

The outline (edge) emphasis image process is an image process in which the brightness difference at an outline (edge) portion (a brightness changing portion) in an image is increased.

The blood vessel structure emphasis image process is an image process in which the frequency components corresponding to the blood vessel patterns are emphasized.

The image processor 24 performs at least one of the contrast suppression image process, outline (edge) suppression image process and blood vessel structure suppression image process for the imaging signal that is one of the B imaging signal, G imaging signal, and R imaging signal and that corresponds to a color range not including the emphasis narrow band light.

The three image processes are known image processes per se.

That is, the contrast suppression image process is a process in which the image brightness difference (contrast) is decreased.

The outline (edge) suppression image process is an image process in which the brightness difference at an outline (an edge or a brightness changing portion) in an image is decreased.

The blood vessel structure suppression image process is an image process in which the frequency components corresponding to the blood vessel patterns are suppressed.

Where the emphasis narrow band light and the non-emphasis narrow band light are included only in two color ranges (for example, the case where only the first laser light and fourth laser light are used), an observation object image may be generated by assigning two imaging signals to three image signals in a known color conversion process (for example, an R image is generated from a G imaging signal, and G and B images are generated from a B imaging signal).

Figure 12:
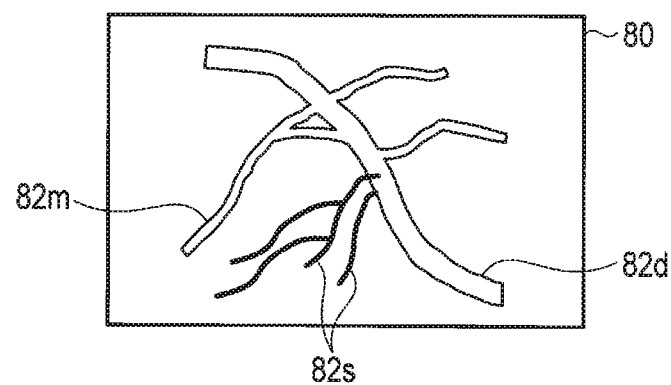
FIG. 12 is a diagram showing an example of an observation object image displayed in observation mode M1 (superficial blood vessel emphasis mode).

The B image signal, G image signal, and R image signal generated by the image processor 24 are transmitted to the image display 16 and are displayed as an observation object image 80, as shown in FIG. 10 and FIG. 12. That is, in this observation object image 80, the superficial blood vessel image 82s showing the superficial blood vessels 68s is highlighted, while the intermediate blood vessel image 82m and deep blood vessel image 82d showing the intermediate blood vessels 68m and deep blood vessels 68d are not highlighted.

<Observation Mode M2 (Intermediate Blood Vessel Emphasis Mode)>

Where the user enters observation mode M2 (intermediate blood vessel emphasis mode) from the input device 18 as an observation mode, the input device 18 outputs observation mode information on observation mode M2 (intermediate blood vessel emphasis mode) to the light source driver 46 and the image processor 24.

Figure 13:
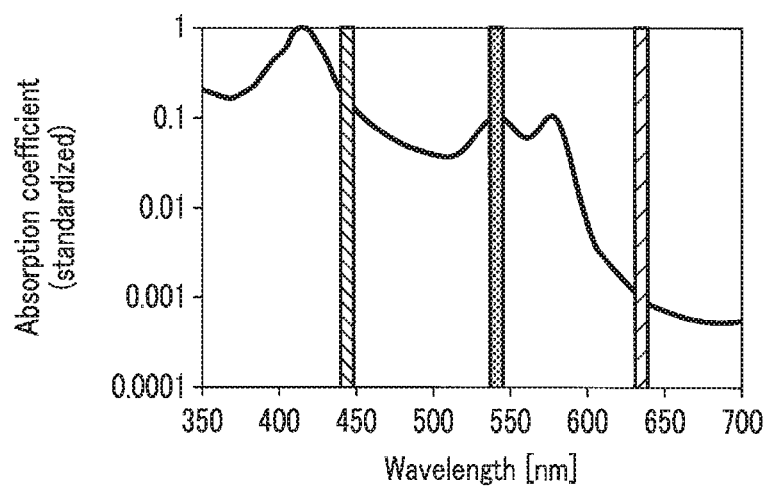
FIG. 13 is a diagram showing how an illumination light spectrum is in observation mode M2 (intermediate blood vessel emphasis mode).

Upon receipt of the observation mode information on observation mode M2 (intermediate blood vessel emphasis mode), the light source driver 46 turns on laser light source 44-2 (laser 2), laser light source 44-3 (laser 3), and laser light source 44-6 (laser 6), so as to cause the laser light sources 44-2, 44-3, and 44-6 to emit second laser light, third laser light, and sixth laser light, as shown in FIG. 7, FIG. 9, and FIG. 13.

That is, the light quantity ratio changing section 72 of the light source driver 46 changes the first to third light quantity ratios, as follows:

light quantity ratio (first light quantity ratio) between first laser light and second laser light=0:1 light quantity ratio (second light quantity ratio) between third laser light and fourth laser light=1:0 light quantity ratio (third light quantity ratio) between fifth laser light and sixth laser light=0:1

Laser light source 44-2 (laser 2) is a non-emphasis narrow band light source corresponding to the superficial blood vessels 68$s$ (superficial region 70$s$), and the second laser light emitted from laser light source 44-2 (laser 2) is non-emphasis narrow band light corresponding to the superficial blood vessels 68$s$ (the superficial region 70$s$). The wavelength of the second laser light, the non-emphasis narrow band light corresponding to the superficial blood vessels 68$s$, is 445 nm and is included in the blue range 58B, as shown in FIG. 9 and FIG. 13. In FIG. 13, the ordinate axis of the laser light spectrum is drawn in an arbitrary scale.

Laser light source 44-3 (laser 3) is an emphasis narrow band light source corresponding to the intermediate blood vessels 68$m$ (intermediate region 70$m$), and the third laser light emitted from laser light source 44-3 (laser 3) is emphasis narrow band light corresponding to the intermediate blood vessels 68$m$ (intermediate region 70$m$). The wavelength of the third laser light, the emphasis narrow band light corresponding to the intermediate blood vessels 68$m$, is 540 nm and is included in the green range 58G, as shown in FIG. 9 and FIG. 13.

Laser light source 44-6 (laser 6) is a non-emphasis narrow band light source corresponding to the deep blood vessels 68$d$ (deep region 70$d$), and the sixth laser light emitted from laser light source 44-6 (laser 6) is non-emphasis narrow band light corresponding to the deep blood vessels 68$d$ (deep region 70$d$). The wavelength of the sixth laser light, the non-emphasis narrow band light corresponding to the deep blood vessels 68$d$, is 635 nm and is included in the red range 58R, as shown in FIG. 9 and FIG. 13.

After being guided by the optical fibers 48-2, 48-3, and 48-6, the second laser light, third laser light and sixth laser light are combined together by the light combiner 50.

The combined second laser light, third laser light and sixth laser light are converted into light having a desirable light distribution by the light converter 54 at the distal end of the insertion section 26, and the resultant light is radiated to the observation object O as illumination light IL.

The second laser light whose wavelength is included in the blue range 58B has a reach length up to the superficial region 70$s$. Where the second laser light is radiated to the observation object O, a small light intensity difference occurs between the light intensity that the reflected and scattered light RL has in the superficial blood vessels 68$s$ and the light intensity that the reflected and scattered light RL has near the superficial blood vessels 68$s$. In other words, a low contrast is provided for the superficial blood vessels 68$s$. That is, the superficial blood vessels 68$s$ are not emphasized.

The reflected and scattered light RL of the illumination light IL in the observation object O is detected by the imager 22. In the imager 22, the B light detection element detects the reflected and scattered light RL of the second laser light whose wavelength is included in the blue range 58B, and generates a B imaging signal. The B imaging signal is output to the image processor 24. The image processor 24 performs image processing for the B imaging signal output from the imager 22 in accordance with observation mode information, and generates a B image signal.

The third laser light whose wavelength is included in the green range 58G has a reach length up to the intermediate region 70$m$. Where the third laser light is radiated to the observation object O, a large light intensity difference occurs between the light intensity that the reflected and scattered light RL has in the intermediate blood vessels 68$m$ and the light intensity that the reflected and scattered light RL has near the intermediate blood vessels 68$m$. In other words, a high contrast is provided for the intermediate blood vessels 68$m$. That is, the intermediate blood vessels 68$m$ are emphasized.

In the imager 22, the G light detection element detects the reflected and scattered light RL of the third laser light whose wavelength is included in the green range 58G, and generates a G imaging signal. The G imaging signal is output to the image processor 24. The image processor 24 performs image processing for the G imaging signal output from the imager 22 in accordance with observation mode information, and generates a G image signal.

The sixth laser light whose wavelength is included in the red range 58R has a reach length up to the deep region 70$d$. Where the sixth laser light is radiated to the observation object O, a small light intensity difference occurs between the light intensity that the reflected and scattered light RL has in the deep blood vessels 68$d$ and the light intensity that the reflected and scattered light RL has near the deep blood vessels 68$d$. In other words, a low contrast is provided for the deep blood vessels 68$d$. That is, the deep blood vessels 68$d$ are not emphasized.

In the imager 22, the R light detection element detects the reflected and scattered light RL of the sixth laser light whose wavelength is included in the red range 58R, and generates an R imaging signal. The R imaging signal is output to the image processor 24. The image processor 24 performs image processing for the R imaging signal output from the imager 22 in accordance with observation mode information, and generates an R image signal.

That is, the light intensity that the reflected and scattered light RL of the illumination light IL has in the intermediate blood vessels 68$m$ is more different from the light intensity that the reflected and scattered light RL has near the blood vessels (in the mucous membrane or the like), than the light intensity that the reflected and scattered light RL has in the superficial blood vessels 68$s$ and the deep blood vessels 68$d$.

In the illumination light IL in observation mode M2 (the intermediate blood vessel emphasis mode), the intermediate region 70$m$ is an attention depth region, and the superficial region 70$s$ and the deep region 70$d$ are non-attention depth regions.

This observation mode is effective in observing the intermediate blood vessels 68m in detail.

The image processor 24 performs at least one of the contrast emphasis image process, outline (edge) emphasis image process, and blood vessel structure emphasis image process for the imaging signal (the G imaging signal in this case) that is one of the B imaging signal, G imaging signal, and R imaging signal and that corresponds to the color range including the emphasis narrow band light. The image processor 24 performs at least one of the contrast suppression image process, outline (edge) suppression image process, and blood vessel structure suppression image process for the imaging signals (the B imaging signal and the R imaging signal in this case) that are part of the B imaging signal, G imaging signal, and R imaging signal and that correspond to the color ranges not including the emphasis narrow band light.

Figure 14:
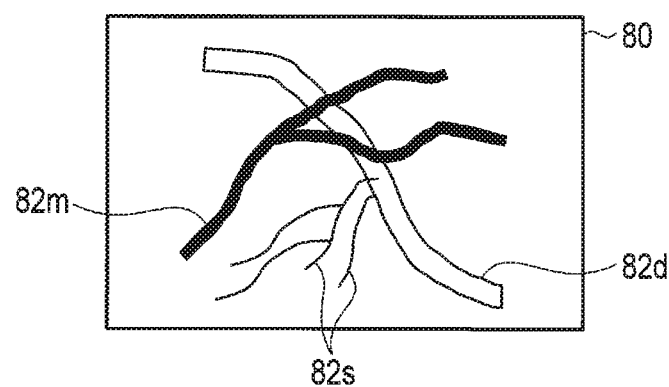
FIG. 14 is a diagram showing an example of an observation object image displayed in observation mode M2 (intermediate blood vessel emphasis mode).

The B image signal, G image signal, and R image signal generated by the image processor 24 are transmitted to the image display 16 and are displayed as an observation object image 80, as shown in FIG. 10 and FIG. 14. That is, in this observation object image 80, the intermediate blood vessel image 82m showing the intermediate blood vessels 68m is highlighted, while the superficial blood vessel image 82s and deep blood vessel image 82d showing the superficial blood vessels 68s and deep blood vessels 68d are not highlighted.

<Observation Mode M3 (Deep Blood Vessel Emphasis Mode)>

Where the user enters observation mode M3 (the deep blood vessel emphasis mode) from the input device 18 as an observation mode, the input device 18 outputs observation mode information on observation mode M3 (the deep blood vessel emphasis mode) to the light source driver 46 and the image processor 24.

Figure 15:
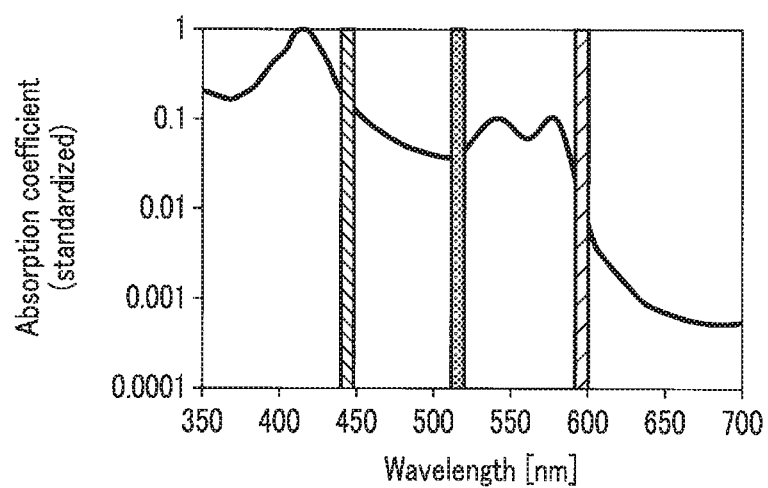
FIG. 15 is a diagram showing how an illumination light spectrum is in observation mode M3 (deep blood vessel emphasis mode).

Upon receipt of the observation mode information on observation mode M3 (the deep blood vessel emphasis mode), the light source driver 46 turns on laser light source 44-2 (laser 2), laser light source 44-4 (laser 4), and laser light source 44-5 (laser 5), so as to cause the laser light sources 44-2, 44-4, and 44-5 to emit second laser light, fourth laser light, and fifth laser light, as shown in FIG. 7, FIG. 9, and FIG. 15.

That is, the light quantity ratio changing section 72 of the light source driver 46 changes the first to third light quantity ratios, as follows:

light quantity ratio (first light quantity ratio) between first laser light and second laser light=0:1 light quantity ratio (second light quantity ratio) between third laser light and fourth laser light=0:1 light quantity ratio (third light quantity ratio) between fifth laser light and sixth laser light=1:0

Laser light source 44-2 (laser 2) is a non-emphasis narrow band light source corresponding to the superficial blood vessels 68s (superficial region 70s), and the second laser light emitted from laser light source 44-2 (laser 2) is non-emphasis narrow band light corresponding to the superficial blood vessels 68s (superficial region 70s). The wavelength of the second laser light, the non-emphasis narrow band light corresponding to the superficial blood vessels 68s, is 445 nm and is included in the blue range 58B, as shown in FIG. 9 and FIG. 15. In FIG. 15, the ordinate axis of the laser light spectrum is drawn in an arbitrary scale.

Laser light source 44-4 (laser 4) is a non-emphasis narrow band light source corresponding to the intermediate blood vessels 68m (intermediate region 70m), and the fourth laser light emitted from laser light source 44-4 (laser 4) is non-emphasis narrow band light corresponding to the intermediate blood vessels 68m (intermediate region 70m). The wavelength of the fourth laser light, the non-emphasis narrow band light corresponding to the intermediate blood vessels 68m, is 515 nm and is included in the green range 58G, as shown in FIG. 9 and FIG. 15.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light, the emphasis narrow band light corresponding to the deep blood vessels 68d, is 595 nm and is included in the red range 58R, as shown in FIG. 9 and FIG. 15.

After being guided by the optical fibers 48-2, 48-4, and 48-5, the second laser light, fourth laser light, and fifth laser light are combined together by the light combiner 50.

The combined second laser light, fourth laser light, and fifth laser light are converted into light having a desirable light distribution by the light converter 54 at the distal end of the insertion section 26, and the resultant light is radiated to the observation object O as illumination light IL.

The second laser light whose wavelength is included in the blue range 58B has a reach length up to the superficial region 70s. Where the second laser light is radiated to the observation object O, a small light intensity difference occurs between the light intensity that the reflected and scattered light RL has in the superficial blood vessels 68s and the light intensity that the reflected and scattered light RL has near the superficial blood vessels 68s. In other words, a low contrast is provided for the superficial blood vessels 68s. That is, the superficial blood vessels 68s are not emphasized.

The reflected and scattered light RL of the illumination light IL in the observation object O is detected by the imager 22. In the imager 22, the B light detection element detects the reflected and scattered light RL of the second laser light whose wavelength is included in the blue range 58B, and generates a B imaging signal. The B imaging signal is output to the image processor 24. The image processor 24 performs image processing for the B imaging signal output from the imager 22 in accordance with observation mode information, and generates a B image signal.

The fourth laser light whose wavelength is included in the green range 58G has a reach length up to the intermediate region 70m. Where the fourth laser light is radiated to the observation object O, a small light intensity difference occurs between the light intensity that the reflected and scattered light RL has in the intermediate blood vessels 68m and the light intensity that the reflected and scattered light RL has near the intermediate blood vessels 68m. In other words, a low contrast is provided for the intermediate blood vessels 68m. That is, the intermediate blood vessels 68m are not emphasized.

In the imager 22, the G light detection element detects the reflected and scattered light RL of the fourth laser light whose wavelength is included in the green range 58G, and generates a G imaging signal. The G imaging signal is output to the image processor 24. The image processor 24 performs image processing for the G imaging signal output from the imager 22 in accordance with observation mode information, and generates a G image signal.

The fifth laser light whose wavelength is included in the red range 58R has a reach length up to the deep region 70d. Where the fifth laser light is radiated to the observation object O, a large light intensity difference occurs between the light intensity that the reflected and scattered light RL has in the deep blood vessels 68d and the light intensity that the reflected and scattered light RL has near the deep blood vessels 68d. In other words, a high contrast is provided for the deep blood vessels 68d. That is, the deep blood vessels 68d are emphasized.

In the imager 22, the R light detection element detects the reflected and scattered light RL of the fifth laser light whose wavelength is included in the red range 58R, and generates an R imaging signal. The R imaging signal is output to the image processor 24. The image processor 24 performs image processing for the R imaging signal output from the imager 22 in accordance with observation mode information, and generates an R image signal.

That is, the light intensity that the reflected and scattered light RL of the illumination light IL has in the deep blood vessels 68d is more different from the light intensity that the reflected and scattered light RL has near the blood vessels (in the mucous membrane or the like), than the light intensity that the reflected and scattered light RL has in the superficial blood vessels 68s and the intermediate blood vessels 68m.

In the illumination light IL in observation mode M3 (the deep blood vessel emphasis mode), the deep region 70d is an attention depth region, and the superficial region 70s and the intermediate region 70m are non-attention depth regions.

This observation mode is effective in observing the deep blood vessels 68d in detail.

The image processor 24 performs at least one of the contrast emphasis image process, outline (edge) emphasis image process, and blood vessel structure emphasis image process for the imaging signal (the R imaging signal in this case) that is one of the B imaging signal, G imaging signal, and R imaging signal and that corresponds to the color range including the emphasis narrow band light. The image processor 24 performs at least one of the contrast suppression image process, outline (edge) suppression image process, and blood vessel structure suppression image process for the imaging signals (the B imaging signal and the G imaging signal in this case) that are part of the B imaging signal, G imaging signal, and R imaging signal and that correspond to the color ranges not including the emphasis narrow band light.

Figure 16:
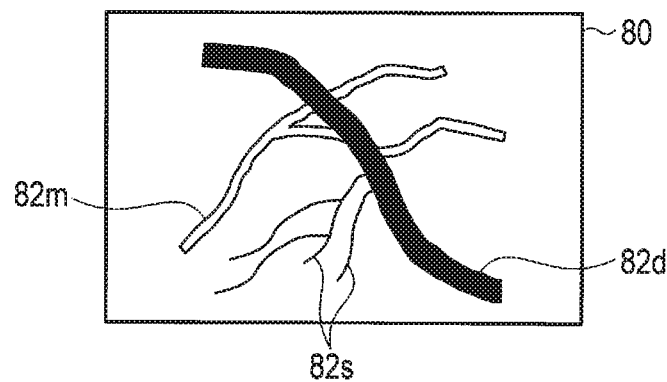
FIG. 16 is a diagram showing an example of an observation object image displayed in observation mode M3 (deep blood vessel emphasis mode).

The B image signal, G image signal, and R image signal generated by the image processor 24 are transmitted to the image display 16 and are displayed as an observation object image 80, as shown in FIG. 10 and FIG. 16. That is, in this observation object image 80, the deep blood vessel image 82d showing the deep blood vessels 68d is highlighted, while the superficial blood vessel image 82s and intermediate blood vessel image 82m showing the superficial blood vessels 68s and intermediate blood vessels 68m are not highlighted.

<Observation Mode M4 (Superficial and Intermediate Blood Vessel Emphasis Mode)>

Where the user enters observation mode M4 (the superficial and intermediate blood vessel emphasis mode) from the input device 18 as an observation mode, the input device 18 outputs observation mode information on observation mode M4 (the superficial and intermediate blood vessel emphasis mode) to the light source driver 46 and the image processor 24.

Figure 17:
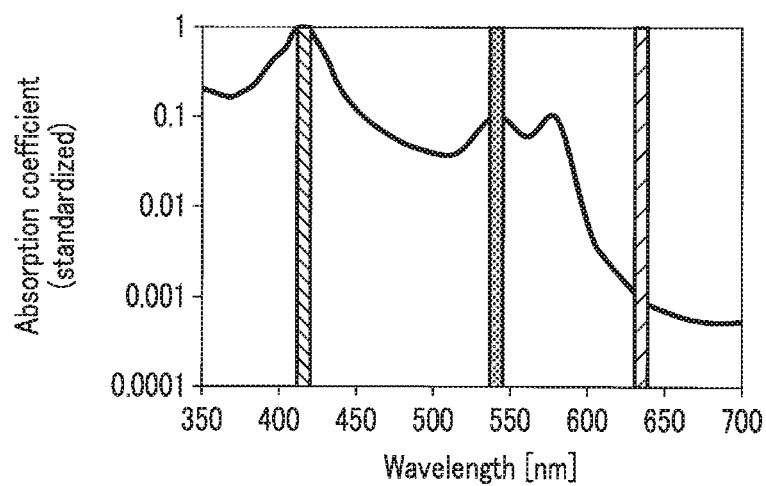
FIG. 17 is a diagram showing how an illumination light spectrum is in observation mode M4 (superficial and intermediate blood vessel emphasis mode).

Upon receipt of the observation mode information on observation mode M4 (the superficial and intermediate blood vessel emphasis mode), the light source driver 46 turns on laser light source 44-1 (laser 1), laser light source 44-3 (laser 3), and laser light source 44-6 (laser 6), so as to cause the laser light sources 44-1, 44-3, and 44-6 to emit first laser light, third laser light, and sixth laser light, as shown in FIG. 7, FIG. 9, and FIG. 17.

That is, the light quantity ratio changing section 72 of the light source driver 46 changes the first to third light quantity ratios, as follows:

light quantity ratio (first light quantity ratio) between first laser light and second laser light=1:0 light quantity ratio (second light quantity ratio) between third laser light and fourth laser light=1:0 light quantity ratio (third light quantity ratio) between fifth laser light and sixth laser light=0:1

Laser light source 44-1 (laser 1) is an emphasis narrow band light source corresponding to the superficial blood vessels 68s (superficial region 70s), and the first laser light emitted from laser light source 44-1 (laser 1) is emphasis narrow band light corresponding to the superficial blood vessels 68s (superficial region 70s). The wavelength of the first laser light, the emphasis narrow band light corresponding to the superficial blood vessels 68s, is 415 nm and is included in the blue range 58B, as shown in FIG. 9 and FIG. 17. In FIG. 17, the ordinate axis of the laser light spectrum is drawn in an arbitrary scale.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light, the emphasis narrow band light corresponding to the intermediate blood vessels 68m, is 540 nm and is included in the green range 58G, as shown in FIG. 9 and FIG. 17.

Laser light source 44-6 (laser 6) is a non-emphasis narrow band light source corresponding to the deep blood vessels 68d (deep region 70d), and the sixth laser light emitted from laser light source 44-6 (laser 6) is non-emphasis narrow band light corresponding to the deep blood vessels 68d (deep region 70d). The wavelength of the sixth laser light, the non-emphasis narrow band light corresponding to the deep blood vessels 68d, is 635 nm and is included in the red range 58R, as shown in FIG. 9 and FIG. 17.

The first laser light, third laser light, and sixth laser light are combined together, as described above, and the resultant light is emitted from the light converter 54 at the distal end of the insertion section 26 and radiated to the observation object O as illumination light IL.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the superficial blood vessels 68s and the intermediate blood vessels 68m is more different from the light intensity that the reflected and scattered light RL has near the blood vessels (in the mucous membrane or the like), than the light intensity that the reflected and scattered light RL has in the deep blood vessels 68d.

In the illumination light IL in observation mode M4 (the superficial and intermediate blood vessel emphasis mode), the superficial region 70s and the intermediate region 70m are attention depth regions, and the deep region 70d is a non-attention depth region.

This observation mode is effective in observing the superficial blood vessels 68s and intermediate blood vessels 68m in detail.

The image processor 24 performs at least one of the contrast emphasis image process, outline (edge) emphasis image process, and blood vessel structure emphasis image process for the imaging signals (the B imaging signal and the G imaging signal in this case) that are part of the B imaging signal, G imaging signal, and R imaging signal and that correspond to the color ranges including the emphasis narrow band light. The image processor 24 performs at least one of the contrast suppression image process, outline (edge) suppression image process, and blood vessel structure suppression image process for the imaging signal (the R imaging signal in this case) that is one of the B imaging signal, G imaging signal, and R imaging signal and that corresponds to the color range not including the emphasis narrow band light.

Figure 18:
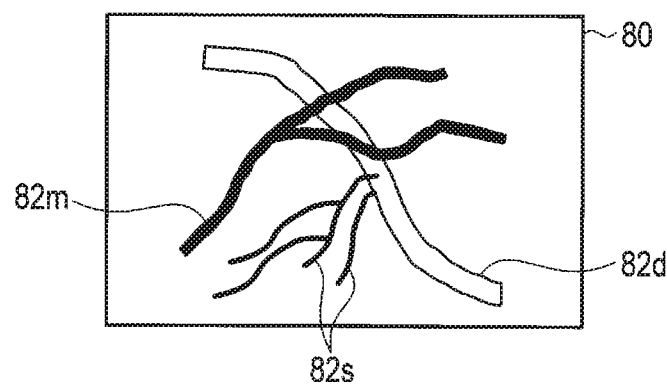
FIG. 18 is a diagram showing an example of an observation object image displayed in observation mode M4 (superficial and intermediate blood vessel emphasis mode).

The B image signal, G image signal, and R image signal generated by the image processor 24 are transmitted to the image display 16 and are displayed as an observation object image 80, as shown in FIG. 10 and FIG. 18. That is, in this observation object image 80, the superficial blood vessel image 82s and intermediate blood vessel image 82m showing the superficial blood vessels 68s and intermediate blood vessels 68m are highlighted, while the deep blood vessel image 82d showing the deep blood vessels 68d is not highlighted.

<Observation Mode M5 (Superficial and Deep Blood Vessel Emphasis Mode)>

Where the user enters observation mode M5 (the superficial and deep blood vessel emphasis mode) from the input device 18 as an observation mode, the input device 18 outputs observation mode information on observation mode M5 (the superficial and deep blood vessel emphasis mode) to the light source driver 46 and the image processor 24.

Upon receipt of the observation mode information on observation mode M5 (the superficial and deep blood vessel emphasis mode), the light source driver 46 turns on laser light source 44-1 (laser 1), laser light source 44-4 (laser 4), and laser light source 44-5 (laser 5), so as to cause the laser light sources 44-1, 44-4, and 44-5 to emit first laser light, fourth laser light, and fifth laser light, as shown in FIG. 7 and FIG. 9.

That is, the light quantity ratio changing section 72 of the light source driver 46 changes the first to third light quantity ratios, as follows:

light quantity ratio (first light quantity ratio) between first laser light and second laser light=1:0 light quantity ratio (second light quantity ratio) between third laser light and fourth laser light=0:1 light quantity ratio (third light quantity ratio) between fifth laser light and sixth laser light=1:0

Laser light source 44-1 (laser 1) is an emphasis narrow band light source corresponding to the superficial blood vessels 68s (superficial region 70s), and the first laser light emitted from laser light source 44-1 (laser 1) is emphasis narrow band light corresponding to the superficial blood vessels 68s (superficial region 70s). The wavelength of the first laser light is 415 nm and is included in the blue range 58B, as shown in FIG. 9.

Laser light source 44-4 (laser 4) is a non-emphasis narrow band light source corresponding to the intermediate blood vessels 68m (intermediate region 70m), and the fourth laser light emitted from laser light source 44-4 (laser 4) is non-emphasis narrow band light corresponding to the intermediate blood vessels 68m (intermediate region 70m). The wavelength of the fourth laser light is 515 nm and is included in the green range 58G, as shown in FIG. 9.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9.

The first laser light, fourth laser light, and fifth laser light are combined together, as described above, and the resultant light is emitted from the light converter 54 at the distal end of the insertion section 26 and radiated to the observation object O as illumination light IL.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the superficial blood vessels 68s and the deep blood vessels 68d is more different from the light intensity that the reflected and scattered light RL has near the blood vessels (in the mucous membrane or the like), than the light intensity that the reflected and scattered light RL has in the intermediate blood vessels 68m.

In the illumination light IL in observation mode M5 (the superficial and deep blood vessel emphasis mode), the superficial region 70s and the deep region 70d are attention depth regions, and the intermediate region 70m is a non-attention depth region.

This observation mode is effective in observing the superficial blood vessels 68s and deep blood vessels 68d in detail.

The image processor 24 performs at least one of the contrast emphasis image process, outline (edge) emphasis image process, and blood vessel structure emphasis image process for the imaging signals (the B imaging signal and the R imaging signal in this case) that are part of the B imaging signal, G imaging signal, and R imaging signal and that correspond to the color ranges including the emphasis narrow band light. The image processor 24 performs at least one of the contrast suppression image process, outline (edge) suppression image process, and blood vessel structure suppression image process for the imaging signal (the G imaging signal in this case) that is one of the B imaging signal, G imaging signal, and R imaging signal and that corresponds to the color range not including the emphasis narrow band light.

The B image signal, G image signal, and R image signal generated by the image processor 24 are transmitted to the image display 16 and are displayed as an observation object image 80, as shown in FIG. 10. That is, in this observation object image 80, the superficial blood vessel image 82s and deep blood vessel image 82d showing the superficial blood vessels 68s and deep blood vessels 68d are highlighted, while the intermediate blood vessel image 82m showing the intermediate blood vessels 68m is not highlighted.

<Observation Mode M6 (Intermediate and Deep Blood Vessel Emphasis Mode)>

Where the user enters observation mode M6 (the intermediate and deep blood vessel emphasis mode) from the input device 18 as an observation mode, the input device 18 outputs observation mode information on observation mode M6 (the intermediate and deep blood vessel emphasis mode) to the light source driver 46 and the image processor 24.

Upon receipt of the observation mode information on observation mode M6 (the intermediate and deep blood vessel emphasis mode), the light source driver 46 turns on laser light source 44-2 (laser 2), laser light source 44-3 (laser 3), and laser light source 44-5 (laser 5), so as to cause the laser light sources 44-2, 44-3, and 44-5 to emit second laser light, third laser light, and fifth laser light, as shown in FIG. 7 and FIG. 9.

That is, the light quantity ratio changing section 72 of the light source driver 46 changes the first to third light quantity ratios, as follows:

light quantity ratio (first light quantity ratio) between first laser light and second laser light=0:1 light quantity ratio (second light quantity ratio) between third laser light and fourth laser light=1:0 light quantity ratio (third light quantity ratio) between fifth laser light and sixth laser light=1:0

Laser light source 44-2 (laser 2) is a non-emphasis narrow band light source corresponding to the superficial blood vessels 68s (superficial region 70s), and the second laser light emitted from laser light source 44-2 (laser 2) is non-emphasis narrow band light corresponding to the superficial blood vessels 68s (superficial region 70s). The wavelength of the second laser light is 445 nm and is included in the blue range 58B, as shown in FIG. 9.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light is 540 nm and is included in the green range 58G, as shown in FIG. 9.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9.

The second laser light, third laser light, and fifth laser light are combined together, as described above, and the resultant light is emitted from the light converter 54 at the distal end of the insertion section 26 and radiated to the observation object O as illumination light IL.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the intermediate blood vessels 68m and deep blood vessels 68d is more different from the light intensity that the reflected and scattered light RL has near the blood vessels (in the mucous membrane or the like), than the light intensity that the reflected and scattered light RL has in the superficial blood vessels 68s.

In the illumination light IL in observation mode M6 (the intermediate and deep blood vessel emphasis mode), the intermediate region 70m and the deep region 70d are attention depth regions, and the superficial region 70s is a non-attention depth region.

This observation mode is effective in observing the intermediate blood vessels 68m and deep blood vessels 68d in detail.

The image processor 24 performs at least one of the contrast emphasis image process, outline (edge) emphasis image process, and blood vessel structure emphasis image process for the imaging signals (the G imaging signal and the R imaging signal in this case) that are part of the B imaging signal, G imaging signal, and R imaging signal and that correspond to the color ranges including the emphasis narrow band light. The image processor 24 performs at least one of the contrast suppression image process, outline (edge) suppression image process, and blood vessel structure suppression image process for the imaging signal (the B imaging signal in this case) that is one of the B imaging signal, G imaging signal, and R imaging signal and that corresponds to the color range not including the emphasis narrow band light.

The B image signal, G image signal, and R image signal generated by the image processor 24 are transmitted to the image display 16 and are displayed as an observation object image 80, as shown in FIG. 10. That is, in this observation object image 80, the intermediate blood vessel image 82m and deep blood vessel image 82d showing the intermediate blood vessels 68m and deep blood vessels 68d are highlighted, while the superficial blood vessel image 82s showing the superficial blood vessels 68s is not highlighted.

<Observation Mode M7 (Superficial, Intermediate, and Deep Blood Vessel Emphasis Mode)>

Where the user enters observation mode M7 (the superficial, intermediate, and deep blood vessel emphasis mode) from the input device 18 as an observation mode, the input device 18 outputs observation mode information on observation mode M7 (the superficial, intermediate, and deep blood vessel emphasis mode) to the light source driver 46 and the image processor 24.

Upon receipt of the observation mode information on observation mode M7 (the superficial, intermediate, and deep blood vessel emphasis mode), the light source driver 46 turns on laser light source 44-1 (laser 1), laser light source 44-3 (laser 3), and laser light source 44-5 (laser 5), so as to cause the laser light sources 44-1, 44-3, and 44-5 to emit first laser light, third laser light, and fifth laser light, as shown in FIG. 7 and FIG. 9.

That is, the light quantity ratio changing section 72 of the light source driver 46 changes the first to third light quantity ratios, as follows:

light quantity ratio (first light quantity ratio) between first laser light and second laser light=1:0 light quantity ratio (second light quantity ratio) between third laser light and fourth laser light=1:0 light quantity ratio (third light quantity ratio) between fifth laser light and sixth laser light=1:0

Laser light source 44-1 (laser 1) is an emphasis narrow band light source corresponding to the superficial blood vessels 68s (superficial region 70s), and the first laser light emitted from laser light source 44-1 (laser 1) is emphasis narrow band light corresponding to the superficial blood vessels 68s (superficial region 70s). The wavelength of the first laser light is 415 nm and is included in the blue range 58B, as shown in FIG. 9.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light is 540 nm and is included in the green range 58G, as shown in FIG. 9.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9.

The first laser light, third laser light, and fifth laser light are combined together, as described above, and the resultant light is emitted from the light converter 54 at the distal end of the insertion section 26 and radiated to the observation object O as illumination light IL.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

In the illumination light IL in observation mode M7 (the superficial, intermediate, and deep blood vessel emphasis mode), the superficial region 70s, the intermediate region 70m, and the deep region 70d are attention depth regions. Since non-emphasis narrow band light is not used, a non-attention depth region is not present.

This observation mode is effective in observing all of the superficial blood vessels 68s, intermediate blood vessels 68m, and deep blood vessels 68d in detail.

The image processor 24 performs at least one of the contrast emphasis image process, outline (edge) emphasis image process, and blood vessel structure emphasis image process for the B imaging signal, G imaging signal, and R imaging signal.

The B image signal, G image signal, and R image signal generated by the image processor 24 are transmitted to the image display 16 and are displayed as an observation object image 80, as shown in FIG. 10. That is, in this observation object image 80, the superficial blood vessel image 82s, the intermediate blood vessel image 82m, and the deep blood vessel image 82d respectively showing the superficial blood vessels 68s, the intermediate blood vessels 68m, and deep blood vessels 68d are all highlighted.

<Observation Mode M8 (Superficial and Intermediate Blood Vessel Intermediate-Emphasis Mode 1)>

Where the user enters observation mode M8 (superficial and intermediate blood vessel intermediate-emphasis mode 1) from the input device 18 as an observation mode, the input device 18 outputs observation mode information on observation mode M8 (superficial and intermediate blood vessel intermediate-emphasis mode 1) to the light source driver 46 and the image processor 24.

Figure 19:
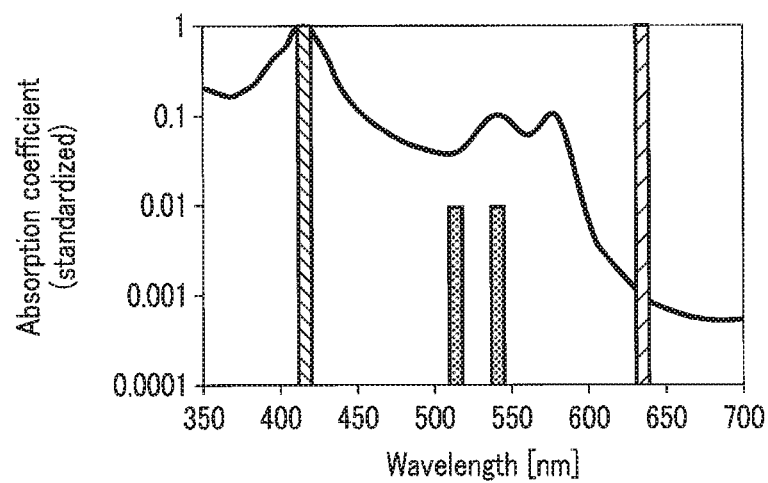
FIG. 19 is a diagram showing how an illumination light spectrum is in observation mode M8 (superficial and intermediate blood vessel intermediate-emphasis mode 1).

Upon receipt of the observation mode information on observation mode M8 (superficial and intermediate blood vessel intermediate-emphasis mode 1), the light source driver 46 turns on laser light source 44-1 (laser 1), laser light source 44-3 (laser 3), laser light source 44-4 (laser 4), and laser light source 44-6 (laser 6), so as to cause the laser light sources 44-1, 44-3, 44-4, and 44-6 to emit first laser light, third laser light, fourth laser light, and sixth laser light, as shown in FIG. 7, FIG. 9, and FIG. 19.

In this case, the light quantity ratio changing section 72 of the light source driver 46 changes the first to third light quantity ratios, as follows:

light quantity ratio (first light quantity ratio) between first laser light and second laser light=1:0 light quantity ratio (second light quantity ratio) between third laser light and fourth laser light=0.5:0.5 light quantity ratio (third light quantity ratio) between fifth laser light and sixth laser light=0:1

Laser light source 44-1 (laser 1) is an emphasis narrow band light source corresponding to the superficial blood vessels 68s (superficial region 70s), and the first laser light emitted from laser light source 44-1 (laser 1) is emphasis narrow band light corresponding to the superficial blood vessels 68s (superficial region 70s). The wavelength of the first laser light is 415 nm and is included in the blue range 58B, as shown in FIG. 9 and FIG. 19.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light is 540 nm and is included in the green range 58G, as shown in FIG. 9 and FIG. 19.

Laser light source 44-4 (laser 4) is a non-emphasis narrow band light source corresponding to the intermediate blood vessels 68m (intermediate region 70m), and the fourth laser light emitted from laser light source 44-4 (laser 4) is non-emphasis narrow band light corresponding to the intermediate blood vessels 68m (intermediate region 70m). The wavelength of the fourth laser light is 515 nm and is included in the green range 58G, as shown in FIG. 9 and FIG. 19.

Laser light source 44-6 (laser 6) is a non-emphasis narrow band light source corresponding to the deep blood vessels 68d (deep region 70d), and the sixth laser light emitted from laser light source 44-6 (laser 6) is non-emphasis narrow band light corresponding to the deep blood vessels 68d (deep region 70d). The wavelength of the sixth laser light is 635 nm and is included in the red range 58R, as shown in FIG. 9 and FIG. 19.

The first laser light, third laser light, fourth laser light, and sixth laser light are combined together, as described above, and the resultant light is emitted from the light converter 54 at the distal end of the insertion section 26 and radiated to the observation object O as illumination light IL. In other words, in this observation mode M8 (superficial and intermediate blood vessel intermediate-emphasis mode 1), the third laser light that emphasizes the intermediate blood vessels 68m and the fourth laser light that does not emphasize the intermediate blood vessels 68m are both radiated to the observation object O.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the superficial blood vessels 68s is more different from the light intensity that the reflected and scattered light RL has near the blood vessels (in the mucous membrane or the like), than the light intensity that the reflected and scattered light RL has in the intermediate blood vessels 68m. Further, the light intensity that the reflected and scattered light RL of the illumination light IL has in the intermediate blood vessels 68m is more different from the light intensity that the reflected and scattered light RL has near the blood vessels (in the mucous membrane or the like), than the light intensity that the reflected and scattered light RL has in the deep blood vessels 68d.

The image processor 24 performs at least one of the contrast emphasis image process, outline (edge) emphasis image process, and blood vessel structure emphasis image process for the imaging signal (the B imaging signal in this case) that is one of the B imaging signal, G imaging signal, and R imaging signal and that corresponds to the color range including only the emphasis narrow band light. The image processor 24 performs at least one of the contrast suppression image process, outline (edge) suppression image process, and blood vessel structure suppression image process for the imaging signal (the R imaging signal in this case) that is one of the B imaging signal, G imaging signal, and R imaging signal and that corresponds to the color range not including the emphasis narrow band light. Of the B imaging signal, G imaging signal, and R imaging signal, the imaging signal corresponding to the remaining color range (the G imaging signal in this case) is not subjected to the emphasis image process or suppression image process.

Figure 20:
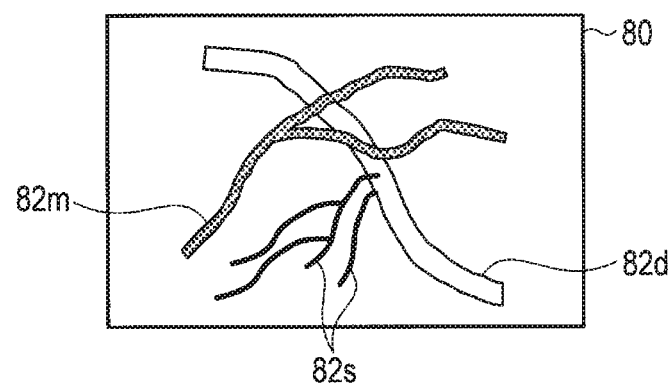
FIG. 20 is a diagram showing an example of an observation object image displayed in observation mode M8 (superficial and intermediate blood vessel intermediate-emphasis mode 1).

The B image signal, G image signal, and R image signal generated by the image processor 24 are transmitted to the image display 16 and are displayed as an observation object image 80, as shown in FIG. 10 and FIG. 20. That is, in this observation object image 80, the superficial blood vessels 68s are highlighted as a superficial blood vessel image 82s, as in observation mode M1 (superficial blood vessel emphasis mode), while the deep blood vessel image 82d showing the deep blood vessels 68d is not highlighted.

On the other hand, in this observation mode M8 (superficial and intermediate blood vessel intermediate-emphasis mode 1), the third laser light that emphasizes the intermediate blood vessels 68m and the fourth laser light that does not emphasize the intermediate blood vessels 68m are both radiated to the observation object O. As a result, the intermediate blood vessels 68m are emphasized at a level that is intermediate between the state where they are emphasized with only the third laser light radiated and the state where they are not emphasized with only the fourth laser light radiated. That is, the intermediate blood vessel image 82m showing the intermediate blood vessels 68m is highlighted at an intermediate level between observation mode M1 (the superficial blood vessel emphasis mode) and observation mode M4 (the superficial and intermediate blood vessel emphasis mode).

In an image of such an intermediate-level emphasis state, the observation object image 80 provides an enhanced sense of depth, in comparison with an image in which only the superficial blood vessels 68s are emphasized and an image in which the superficial blood vessels 68s and the intermediate blood vessels 68m are emphasized.

The light quantity ratio (second light quantity ratio) between the third laser light and the fourth laser light is not limited to 0.5:0.5 described above. The emphasis level of the intermediate blood vessels 68m is set at a desired emphasis level that is intermediate between the state where intermediate blood vessels are emphasized with only the third laser light radiated and the state where they are not emphasized with only the fourth laser light radiated. The emphasis level can be changed by changing the second light quantity ratio continuously in accordance with the purpose.

The light quantity ratio (second light quantity ratio) between the third laser light and the fourth laser light is changed such that the light quantity in the green range 58G is constant. The case where the light quantity is constant includes a case where the light quantity emitted is constant and a case where the light quantity received by the imaging element of the imager 22 is constant. The second light quantity ratio may be changed in consideration of the spectral sensitivity of the imaging element.

If the light quantity (color) in the green range 58G changes by changing the light quantity ratio (second light quantity) between the third laser light and the fourth laser light, the light quantity of laser light included in color ranges other than the third and fourth laser light may be changed such that the ratio among the light quantity in the blue range 58B, the light quantity in the green range 58G, and the light quantity in the red range 58R becomes constant.

In this observation mode M8 (superficial and intermediate blood vessel intermediate-emphasis mode 1), the sixth laser light need not be used, and only the first laser light, third laser light, and fourth laser light may be used.

<Observation Mode M9 (Superficial and Intermediate Blood Vessel Intermediate-Emphasis Mode 2)>

Where the user enters observation mode M9 (superficial and intermediate blood vessel intermediate-emphasis mode 2) from the input device 18 as an observation mode, the input device 18 outputs observation mode information on observation mode M9 (superficial and intermediate blood vessel intermediate-emphasis mode 2) to the light source driver 46 and the image processor 24.

Upon receipt of the observation mode information on observation mode M9 (superficial and intermediate blood vessel intermediate-emphasis mode 2), the light source driver 46 turns on laser light source 44-1 (laser 1), laser light source 44-2 (laser 2), laser light source 44-3 (laser 3), and laser light source 44-6 (laser 6), so as to cause the laser light sources 44-1, 44-2, 44-3, and 44-6 to emit first laser light, second laser light, third laser light, and sixth laser light, as shown in FIG. 7 and FIG. 9.

In this case, the light quantity ratio changing section 72 of the light source driver 46 changes the first to third light quantity ratios, as follows:

light quantity ratio (first light quantity ratio) between first laser light and second laser light=0.5:0.5 light quantity ratio (second light quantity ratio) between third laser light and fourth laser light=1:0 light quantity ratio (third light quantity ratio) between fifth laser light and sixth laser light=0:1

Laser light source 44-1 (laser 1) is an emphasis narrow band light source corresponding to the superficial blood vessels 68s (superficial region 70s), and the first laser light emitted from laser light source 44-1 (laser 1) is emphasis narrow band light corresponding to the superficial blood vessels 68s (superficial region 70s). The wavelength of the first laser light is 415 nm and is included in the blue range 58B, as shown in FIG. 9.

Laser light source 44-2 (laser 2) is a non-emphasis narrow band light source corresponding to the superficial blood vessels 68s (superficial region 70s), and the second laser light emitted from laser light source 44-2 (laser 2) is non-emphasis narrow band light corresponding to the superficial blood vessels 68s (superficial region 70s). The wavelength of the second laser light is 445 nm and is included in the blue range 58B, as shown in FIG. 9.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light is 540 nm and is included in the green range 58G, as shown in FIG. 9.

Laser light source 44-6 (laser 6) is a non-emphasis narrow band light source corresponding to the deep blood vessels 68d (deep region 70d), and the sixth laser light emitted from laser light source 44-6 (laser 6) is non-emphasis narrow band light corresponding to the deep blood vessels 68d (deep region 70d). The wavelength of the sixth laser light is 635 nm and is included in the red range 58R, as shown in FIG. 9.

The first laser light, second laser light, third laser light, and sixth laser light are combined together, as described above, and the resultant light is emitted from the light converter 54 at the distal end of the insertion section 26 and radiated to the observation object O as illumination light IL. In other words, in this observation mode M9 (superficial and intermediate blood vessel intermediate-emphasis mode 2), the first laser light that emphasizes the superficial blood vessels 68s and the second laser light that does not emphasize the superficial blood vessels 68s are both radiated to the observation object O.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the intermediate blood vessels 68m is more different from the light intensity that the reflected and scattered light RL has near the blood vessels (in the mucous membrane or the like), than the light intensity that the reflected and scattered light RL has in the superficial blood vessels 68s. Further, the light intensity that the reflected and scattered light RL of the illumination light IL has in the superficial blood vessels 68s is more different from the light intensity that the reflected and scattered light RL has near the blood vessels (in the mucous membrane or the like), than the light intensity that the reflected and scattered light RL has in the deep blood vessels 68d.

The image processor 24 performs at least one of the contrast emphasis image process, outline (edge) emphasis image process, and blood vessel structure emphasis image process for the imaging signal (the G imaging signal in this case) that is one of the B imaging signal, G imaging signal, and R imaging signal and that corresponds to the color range including only the emphasis narrow band light. The image processor 24 performs at least one of the contrast suppression image process, outline (edge) suppression image process, and blood vessel structure suppression image process for the imaging signal (the R imaging signal in this case) that is one of the B imaging signal, G imaging signal, and R imaging signal and that corresponds to the color range not including the emphasis narrow band light. Of the B imaging signal, G imaging signal, and R imaging signal, the imaging signal corresponding to the remaining color range (the B imaging signal in this case) is not subjected to the emphasis image process or suppression image process.

The B image signal, G image signal, and R image signal generated by the image processor 24 are transmitted to the image display 16 and are displayed as an observation object image 80, as shown in FIG. 10. That is, in this observation object image 80, the intermediate blood vessels 68m are highlighted as a intermediate blood vessel image 82m, as in observation mode M2 (intermediate blood vessel emphasis mode), while the deep blood vessel image 82d showing the deep blood vessels 68d is not highlighted.

On the other hand, in this observation mode M9 (superficial and intermediate blood vessel intermediate-emphasis mode 2), the first laser light that emphasizes the superficial blood vessels 68s and the second laser light that does not emphasize the superficial blood vessels 68s are both radiated to the observation object O. As a result, the superficial blood vessels 68s are emphasized at a level that is intermediate between the state where they are emphasized with only the first laser light radiated and the state where they are not emphasized with only the second laser light radiated. That is, the superficial blood vessel image 82s showing the superficial blood vessels 68s is highlighted at an intermediate level between observation mode M2 (the intermediate blood vessel emphasis mode) and observation mode M4 (the superficial and intermediate blood vessel emphasis mode).

In an image of such an intermediate-level emphasis state, the observation object image 80 provides an enhanced sense of depth, in comparison with an image in which only the intermediate blood vessels 68m are emphasized and an image in which the superficial blood vessels 68s and the intermediate blood vessels 68m are emphasized.

Needless to say, the light quantity ratio (first light quantity ratio) between the first laser light and the second laser light can be changed, like the light quantity ratio (second light quantity ratio) between the third laser light and the fourth laser light in observation mode M8 (superficial and intermediate blood vessel intermediate-emphasis mode 1).

<Observation Mode M10 (Superficial and Deep Blood Vessel Intermediate-Emphasis Mode 1)>

Where the user enters observation mode M10 (superficial and deep blood vessel intermediate-emphasis mode 1) from the input device 18 as an observation mode, the input device 18 outputs observation mode information on observation mode M10 (superficial and deep blood vessel intermediate-emphasis mode 1) to the light source driver 46 and the image processor 24.

Upon receipt of the observation mode information on observation mode M10 (superficial and deep blood vessel intermediate-emphasis mode 1), the light source driver 46 turns on laser light source 44-1 (laser 1), laser light source 44-4 (laser 4), laser light source 44-5 (laser 5), and laser light source 44-6 (laser 6), so as to cause the laser light sources 44-1, 44-4, 44-5, and 44-6 to emit first laser light, fourth laser light, fifth laser light, and sixth laser light, as shown in FIG. 7 and FIG. 9.

In this case, the light quantity ratio changing section 72 of the light source driver 46 changes the first to third light quantity ratios, as follows:

light quantity ratio (first light quantity ratio) between first laser light and second laser light=1:0 light quantity ratio (second light quantity ratio) between third laser light and fourth laser light=0:1 light quantity ratio (third light quantity ratio) between fifth laser light and sixth laser light=0.5:0.5

Laser light source 44-1 (laser 1) is an emphasis narrow band light source corresponding to the superficial blood vessels 68s (superficial region 70s), and the first laser light emitted from laser light source 44-1 (laser 1) is emphasis narrow band light corresponding to the superficial blood vessels 68s (superficial region 70s). The wavelength of the first laser light is 415 nm and is included in the blue range 58B, as shown in FIG. 9.

Laser light source 44-4 (laser 4) is a non-emphasis narrow band light source corresponding to the intermediate blood vessels 68m (intermediate region 70m), and the fourth laser light emitted from laser light source 44-4 (laser 4) is non-emphasis narrow band light corresponding to the intermediate blood vessels 68m (intermediate region 70m). The wavelength of the fourth laser light is 515 nm and is included in the green range 58G, as shown in FIG. 9.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9.

Laser light source 44-6 (laser 6) is a non-emphasis narrow band light source corresponding to the deep blood vessels 68d (deep region 70d), and the sixth laser light emitted from laser light source 44-6 (laser 6) is non-emphasis narrow band light corresponding to the deep blood vessels 68d (deep region 70d). The wavelength of the sixth laser light is 635 nm and is included in the red range 58R, as shown in FIG. 9.

The first laser light, fourth laser light, fifth laser light, and sixth laser light are combined together, as described above, and the resultant light is emitted from the light converter 54 at the distal end of the insertion section 26 and radiated to the observation object O as illumination light IL. In other words, in this observation mode M10 (superficial and deep blood vessel intermediate-emphasis mode 1), the fifth laser light that emphasizes the deep blood vessels 68d and the sixth laser light that does not emphasize the deep blood vessels 68d are both radiated to the observation object O.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the superficial blood vessels 68s is more different from the light intensity that the reflected and scattered light RL has near the blood vessels (in the mucous membrane or the like), than the light intensity that the reflected and scattered light RL has in the deep blood vessels 68d. Further, the light intensity that the reflected and scattered light RL of the illumination light IL has in the deep blood vessels 68d is more different from the light intensity that the reflected and scattered light RL has near the blood vessels (in the mucous membrane or the like), than the light intensity that the reflected and scattered light RL has in the intermediate blood vessels 68m.

The image processor 24 performs at least one of the contrast emphasis image process, outline (edge) emphasis image process, and blood vessel structure emphasis image process for the imaging signal (the B imaging signal in this case) that is one of the B imaging signal, G imaging signal, and R imaging signal and that corresponds to the color range including only the emphasis narrow band light. The image processor 24 performs at least one of the contrast suppression image process, outline (edge) suppression image process, and blood vessel structure suppression image process for the imaging signal (the G imaging signal in this case) that is one of the B imaging signal, G imaging signal, and R imaging signal and that corresponds to the color range not including the emphasis narrow band light. Of the B imaging signal, G imaging signal, and R imaging signal, the imaging signal corresponding to the remaining color range (the R imaging signal in this case) is not subjected to the emphasis image process or suppression image process.

The B image signal, G image signal, and R image signal generated by the image processor 24 are transmitted to the image display 16 and are displayed as an observation object image 80, as shown in FIG. 10. That is, in this observation object image 80, the superficial blood vessels 68s are highlighted as a superficial blood vessel image 82s, as in observation mode M1 (superficial blood vessel emphasis mode), while the intermediate blood vessel image 82m showing the intermediate blood vessels 68m is not highlighted.

On the other hand, in this observation mode M10 (superficial and deep blood vessel intermediate-emphasis mode 1), the fifth laser light that emphasizes the deep blood vessels 68d and the sixth laser light that does not emphasize the deep blood vessels 68d are both radiated to the observation object O. As a result, the deep blood vessels 68d are emphasized at a level that is intermediate between the state where they are emphasized with only the fifth laser light radiated and the state where they are not emphasized with only the sixth laser light radiated. That is, the deep blood vessel image 82d showing the deep blood vessels 68d is highlighted at an intermediate level between observation mode M1 (the superficial blood vessel emphasis mode) and observation mode M5 (the superficial and deep blood vessel emphasis mode).

In an image of such an intermediate-level emphasis state, the observation object image 80 provides an enhanced sense of depth, in comparison with an image in which only the superficial blood vessels 68s are emphasized and an image in which the superficial blood vessels 68s and the deep blood vessels 68d are emphasized.

Needless to say, the light quantity ratio (third light quantity ratio) between the fifth laser light and the sixth laser light can be changed, like the light quantity ratio (second light quantity ratio) between the third laser light and the fourth laser light in observation mode M8 (superficial and intermediate blood vessel intermediate-emphasis mode 1).

<Observation Mode M11 (Superficial and Deep Blood Vessel Intermediate-Emphasis Mode 2)>

Where the user enters observation mode M11 (superficial and deep blood vessel intermediate-emphasis mode 2) from the input device 18 as an observation mode, the input device 18 outputs observation mode information on observation mode M11 (superficial and deep blood vessel intermediate-emphasis mode 2) to the light source driver 46 and the image processor 24.

Upon receipt of the observation mode information on observation mode M11 (superficial and deep blood vessel intermediate-emphasis mode 2), the light source driver 46 turns on laser light source 44-1 (laser 1), laser light source 44-2 (laser 2), laser light source 44-4 (laser 4), and laser light source 44-5 (laser 5), so as to cause the laser light sources 44-1, 44-2, 44-4, and 44-5 to emit first laser light, second laser light, fourth laser light, and fifth laser light, as shown in FIG. 7 and FIG. 9.

In this case, the light quantity ratio changing section 72 of the light source driver 46 changes the first to third light quantity ratios, as follows:

light quantity ratio (first light quantity ratio) between first laser light and second laser light=0.5:0.5 light quantity ratio (second light quantity ratio) between third laser light and fourth laser light=0:1 light quantity ratio (third light quantity ratio) between fifth laser light and sixth laser light=1:0

Laser light source 44-1 (laser 1) is an emphasis narrow band light source corresponding to the superficial blood vessels 68s (superficial region 70s), and the first laser light emitted from laser light source 44-1 (laser 1) is emphasis narrow band light corresponding to the superficial blood vessels 68s (superficial region 70s). The wavelength of the first laser light is 415 nm and is included in the blue range 58B, as shown in FIG. 9.

Laser light source 44-2 (laser 2) is a non-emphasis narrow band light source corresponding to the superficial blood vessels 68s (superficial region 70s), and the second laser light emitted from laser light source 44-2 (laser 2) is non-emphasis narrow band light corresponding to the superficial blood vessels 68s (superficial region 70s). The wavelength of the second laser light is 445 nm and is included in the blue range 58B, as shown in FIG. 9.

Laser light source 44-4 (laser 4) is a non-emphasis narrow band light source corresponding to the intermediate blood vessels 68m (intermediate region 70m), and the fourth laser light emitted from laser light source 44-4 (laser 4) is non-emphasis narrow band light corresponding to the intermediate blood vessels 68m (intermediate region 70m). The wavelength of the fourth laser light is 515 nm and is included in the green range 58G, as shown in FIG. 9.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9.

The first laser light, second laser light, fourth laser light, and fifth laser light are combined together, as described above, and the resultant light is emitted from the light converter 54 at the distal end of the insertion section 26 and radiated to the observation object O as illumination light IL. In other words, in this observation mode M11 (superficial and deep blood vessel intermediate-emphasis mode 2), the first laser light that emphasizes the superficial blood vessels 68s and the second laser light that does not emphasize the superficial blood vessels 68s are both radiated to the observation object O.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the superficial blood vessels 68s is more different from the light intensity that the reflected and scattered light RL has near the blood vessels (in the mucous membrane or the like), than the light intensity that the reflected and scattered light RL has in the intermediate blood vessels 68m. Further, the light intensity that the reflected and scattered light RL of the illumination light IL has in the deep blood vessels 68d is more different from the light intensity that the reflected and scattered light RL has near the blood vessels (in the mucous membrane or the like), than the light intensity that the reflected and scattered light RL has in the superficial blood vessels 68s.

The image processor 24 performs at least one of the contrast emphasis image process, outline (edge) emphasis image process, and blood vessel structure emphasis image process for the imaging signal (the R imaging signal in this case) that is one of the B imaging signal, G imaging signal, and R imaging signal and that corresponds to the color range including only the emphasis narrow band light. The image processor 24 performs at least one of the contrast suppression image process, outline (edge) suppression image process, and blood vessel structure suppression image process for the imaging signal (the G imaging signal in this case) that is one of the B imaging signal, G imaging signal, and R imaging signal and that corresponds to the color range not including the emphasis narrow band light. Of the B imaging signal, G imaging signal, and R imaging signal, the imaging signal corresponding to the remaining color range (the B imaging signal in this case) is not subjected to the emphasis image process or suppression image process.

The B image signal, G image signal, and R image signal generated by the image processor 24 are transmitted to the image display 16 and are displayed as an observation object image 80, as shown in FIG. 10. That is, in this observation object image 80, the deep blood vessels 68d are highlighted as a deep blood vessel image 82d, as in observation mode M3 (deep blood vessel emphasis mode), while the intermediate blood vessel image 82m showing the intermediate blood vessels 68m is not highlighted.

On the other hand, in this observation mode M11 (superficial and deep blood vessel intermediate-emphasis mode 2), the first laser light that emphasizes the superficial blood vessels 68s and the second laser light that does not emphasize the superficial blood vessels 68s are both radiated to the observation object O. As a result, the superficial blood vessels 68s are emphasized at a level that is intermediate between the state where they are emphasized with only the first laser light radiated and the state where they are not emphasized with only the second laser light radiated. That is, the superficial blood vessel image 82s showing the superficial blood vessels 68s is highlighted at an intermediate level between observation mode M3 (the deep blood vessel emphasis mode) and observation mode M5 (the superficial and deep blood vessel emphasis mode).

In an image of such an intermediate-level emphasis state, the observation object image 80 provides an enhanced sense of depth, in comparison with an image in which only the deep blood vessels 68d are emphasized and an image in which the superficial blood vessels 68s and the deep blood vessels 68d are emphasized.

Needless to say, the light quantity ratio (first light quantity ratio) between the first laser light and the second laser light can be changed, like the light quantity ratio (second light quantity ratio) between the third laser light and the fourth laser light in observation mode M8 (superficial and intermediate blood vessel intermediate-emphasis mode 1).

<Observation Mode M12 (Intermediate and Deep Blood Vessel Intermediate-Emphasis Mode 1)>

Where the user enters observation mode M12 (intermediate and deep blood vessel intermediate-emphasis mode 1) from the input device 18 as an observation mode, the input device 18 outputs observation mode information on observation mode M12 (intermediate and deep blood vessel intermediate-emphasis mode 1) to the light source driver 46 and the image processor 24.

Upon receipt of the observation mode information on observation mode M12 (intermediate and deep blood vessel intermediate-emphasis mode 1), the light source driver 46 turns on laser light source 44-2 (laser 2), laser light source 44-3 (laser 3), laser light source 44-5 (laser 5), and laser light source 44-6 (laser 6), so as to cause the laser light sources 44-2, 44-3, 44-5, and 44-6 to emit second laser light, third laser light, fifth laser light, and sixth laser light, as shown in FIG. 7 and FIG. 9.

In this case, the light quantity ratio changing section 72 of the light source driver 46 changes the first to third light quantity ratios, as follows:

light quantity ratio (first light quantity ratio) between first laser light and second laser light=0:1 light quantity ratio (second light quantity ratio) between third laser light and fourth laser light=1:0 light quantity ratio (third light quantity ratio) between fifth laser light and sixth laser light=0.5:0.5

Laser light source 44-2 (laser 2) is a non-emphasis narrow band light source corresponding to the superficial blood vessels 68s (superficial region 70s), and the second laser light emitted from laser light source 44-2 (laser 1) is non-emphasis narrow band light corresponding to the superficial blood vessels 68s (superficial region 70s). The wavelength of the second laser light is 445 nm and is included in the blue range 58B, as shown in FIG. 9.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light is 540 nm and is included in the green range 58G, as shown in FIG. 9.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9.

Laser light source 44-6 (laser 6) is a non-emphasis narrow band light source corresponding to the deep blood vessels 68d (deep region 70d), and the sixth laser light emitted from laser light source 44-6 (laser 6) is non-emphasis narrow band light corresponding to the deep blood vessels 68d (deep region 70d). The wavelength of the sixth laser light is 635 nm and is included in the red range 58R, as shown in FIG. 9.

The second laser light, third laser light, fifth laser light, and sixth laser light are combined together, as described above, and the resultant light is emitted from the light converter 54 at the distal end of the insertion section 26 and radiated to the observation object O as illumination light IL. In other words, in this observation mode M12 (intermediate and deep blood vessel intermediate-emphasis mode 1), the fifth laser light that emphasizes the deep blood vessels 68d and the sixth laser light that does not emphasize the deep blood vessels 68d are both radiated to the observation object O.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the deep blood vessels 68d is more different from the light intensity that the reflected and scattered light RL has near the blood vessels (in the mucous membrane or the like), than the light intensity that the reflected and scattered light RL has in the superficial blood vessels 68s. Further, the light intensity that the reflected and scattered light RL of the illumination light IL has in the intermediate blood vessels 68m is more different from the light intensity that the reflected and scattered light RL has near the blood vessels (in the mucous membrane or the like), than the light intensity that the reflected and scattered light RL has in the deep blood vessels 68d.

The image processor 24 performs at least one of the contrast emphasis image process, outline (edge) emphasis image process, and blood vessel structure emphasis image process for the imaging signal (the G imaging signal in this case) that is one of the B imaging signal, G imaging signal, and R imaging signal and that corresponds to the color range including only the emphasis narrow band light. The image processor 24 performs at least one of the contrast suppression image process, outline (edge) suppression image process, and blood vessel structure suppression image process for the imaging signal (the B imaging signal in this case) that is one of the B imaging signal, and that corresponds to the color range not including the emphasis narrow band light. Of the B imaging signal, G imaging signal, and R imaging signal, the imaging signal corresponding to the remaining color range (the R imaging signal in this case) is not subjected to the emphasis image process or suppression image process.

The B image signal, G image signal, and R image signal generated by the image processor 24 are transmitted to the image display 16 and are displayed as an observation object image 80, as shown in FIG. 10. That is, in this observation object image 80, the intermediate blood vessels 68m are highlighted as a intermediate blood vessel image 82m, as in observation mode M2 (intermediate blood vessel emphasis mode), while the superficial blood vessel image 82s showing the superficial blood vessels 68s is not highlighted.

On the other hand, in this observation mode M12 (intermediate and deep blood vessel intermediate-emphasis mode 1), the fifth laser light that emphasizes the deep blood vessels 68d and the sixth laser light that does not emphasize the deep blood vessels 68d are both radiated to the observation object O. As a result, the deep blood vessels 68d are emphasized at a level that is intermediate between the state where they are emphasized with only the fifth laser light radiated and the state where they are not emphasized with only the sixth laser light radiated. That is, the deep blood vessel image 82d showing the deep blood vessels 68d is highlighted at an intermediate level between observation mode M2 (the intermediate blood vessel emphasis mode) and observation mode M6 (the intermediate and deep blood vessel emphasis mode).

In an image of such an intermediate-level emphasis state, the observation object image 80 provides an enhanced sense of depth, in comparison with an image in which only the intermediate blood vessels 68m are emphasized and an image in which the intermediate blood vessels 68m and the deep blood vessels 68d are emphasized.

Needless to say, the light quantity ratio (third light quantity ratio) between the fifth laser light and the sixth laser light can be changed, like the light quantity ratio (second light quantity ratio) between the third laser light and the fourth laser light in observation mode M8 (superficial and intermediate blood vessel intermediate-emphasis mode 1).

<Observation Mode M13 (Intermediate and Deep Blood Vessel Intermediate-Emphasis Mode 2)>

Where the user enters observation mode M13 (intermediate and deep blood vessel intermediate-emphasis mode 2) from the input device 18 as an observation mode, the input device 18 outputs observation mode information on observation mode M13 (intermediate and deep blood vessel intermediate-emphasis mode 2) to the light source driver 46 and the image processor 24.

Upon receipt of the observation mode information on observation mode M13 (intermediate and deep blood vessel intermediate-emphasis mode 2), the light source driver 46 turns on laser light source 44-2 (laser 2), laser light source 44-3 (laser 3), laser light source 44-4 (laser 4), and laser light source 44-5 (laser 5), so as to cause the laser light sources 44-2, 44-3, 44-4, and 44-5 to emit second laser light, third laser light, fourth laser light, and fifth laser light, as shown in FIG. 7 and FIG. 9.

In this case, the light quantity ratio changing section 72 of the light source driver 46 changes the first to third light quantity ratios, as follows:

light quantity ratio (first light quantity ratio) between first laser light and second laser light=0:1 light quantity ratio (second light quantity ratio) between third laser light and fourth laser light=0.5:0.5 light quantity ratio (third light quantity ratio) between fifth laser light and sixth laser light=1:0

Laser light source 44-2 (laser 2) is a non-emphasis narrow band light source corresponding to the superficial blood vessels 68s (superficial region 70s), and the second laser light emitted from laser light source 44-2 (laser 2) is non-emphasis narrow band light corresponding to the superficial blood vessels 68s (superficial region 70s). The wavelength of the second laser light is 445 nm and is included in the blue range 58B, as shown in FIG. 9.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light is 540 nm and is included in the green range 58G, as shown in FIG. 9 and FIG. 19.

Laser light source 44-4 (laser 4) is a non-emphasis narrow band light source corresponding to the intermediate blood vessels 68m (intermediate region 70m), and the fourth laser light emitted from laser light source 44-4 (laser 4) is non-emphasis narrow band light corresponding to the intermediate blood vessels 68m (intermediate region 70m). The wavelength of the fourth laser light is 515 nm and is included in the green range 58G, as shown in FIG. 9 and FIG. 19.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9.

The second laser light, third laser light, fourth laser light, and fifth laser light are combined together, as described above, and the resultant light is emitted from the light converter 54 at the distal end of the insertion section 26 and radiated to the observation object O as illumination light IL. In other words, in this observation mode M13 (intermediate and deep blood vessel intermediate-emphasis mode 2), the third laser light that emphasizes the intermediate blood vessels 68m and the fourth laser light that does not emphasize the intermediate blood vessels 68m are both radiated to the observation object O.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the intermediate blood vessels 68m is more different from the light intensity that the reflected and scattered light RL has near the blood vessels (in the mucous membrane or the like), than the light intensity that the reflected and scattered light RL has in the superficial blood vessels 68s. Further, the light intensity that the reflected and scattered light RL of the illumination light IL has in the deep blood vessels 68d is more different from the light intensity that the reflected and scattered light RL has near the blood vessels (in the mucous membrane or the like), than the light intensity that the reflected and scattered light RL has in the intermediate blood vessels 68m.

The image processor 24 performs at least one of the contrast emphasis image process, outline (edge) emphasis image process, and blood vessel structure emphasis image process for the imaging signal (the R imaging signal in this case) that is one of the B imaging signal, G imaging signal, and R imaging signal and that corresponds to the color range including only the emphasis narrow band light. The image processor 24 performs at least one of the contrast suppression image process, outline (edge) suppression image process, and blood vessel structure suppression image process for the imaging signal (the B imaging signal in this case) that is one of the B imaging signal, G imaging signal, and R imaging signal and that corresponds to the color range not including the emphasis narrow band light. Of the B imaging signal, G imaging signal, and R imaging signal, the imaging signal corresponding to the remaining color range (the G imaging signal in this case) is not subjected to the emphasis image process or suppression image process.

The B image signal, G image signal, and R image signal generated by the image processor 24 are transmitted to the image display 16 and are displayed as an observation object image 80, as shown in FIG. 10. That is, in this observation object image 80, the deep blood vessels 68d are highlighted as a deep blood vessel image 82d, as in observation mode M3 (deep blood vessel emphasis mode), while the superficial blood vessel image 82s showing the superficial blood vessels 68s is not highlighted.

On the other hand, in this observation mode M13 (intermediate and deep blood vessel intermediate-emphasis mode 2), the third laser light that emphasizes the intermediate blood vessels 68m and the fourth laser light that does not emphasize the intermediate blood vessels 68m are both radiated to the observation object O. As a result, the intermediate blood vessels 68m are emphasized at a level that is intermediate between the state where they are emphasized with only the third laser light radiated and the state where they are not emphasized with only the fourth laser light radiated. That is, the intermediate blood vessel image 82m showing the intermediate blood vessels 68m is highlighted at an intermediate level between observation mode M3 (the deep blood vessel emphasis mode) and observation mode M6 (the intermediate and deep blood vessel emphasis mode).

In an image of such an intermediate-level emphasis state, the observation object image 80 provides an enhanced sense of depth, in comparison with an image in which only the deep blood vessels 68d are emphasized and an image in which the intermediate blood vessels 68m and the deep blood vessels 68d are emphasized.

Needless to say, the light quantity ratio (second light quantity ratio) between the third laser light and the fourth laser light can be changed, like the second light quantity ratio in observation mode M8 (superficial and intermediate blood vessel intermediate-emphasis mode 1).

<Observation Mode M14 (Superficial, Intermediate, and Deep Blood Vessel Intermediate-Emphasis Mode 1)>

Where the user enters observation mode M14 (superficial, intermediate, and deep blood vessel intermediate-emphasis mode 1) from the input device 18 as an observation mode, the input device 18 outputs observation mode information on observation mode M14 (superficial, intermediate, and deep blood vessel intermediate-emphasis mode 1) to the light source driver 46 and the image processor 24.

Figure 21:
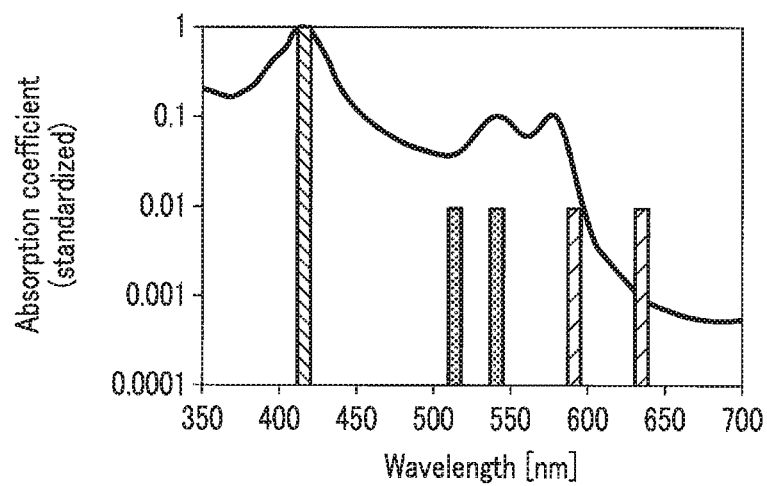
FIG. 21 is a diagram showing how an illumination light spectrum is in observation mode M14 (superficial, intermediate, and deep blood vessel intermediate-emphasis mode 1).

Upon receipt of the observation mode information on observation mode M14 (superficial, intermediate, and deep blood vessel intermediate-emphasis mode 1), the light source driver 46 turns on laser light source 44-1 (laser 1), laser light source 44-3 (laser 3), laser light source 44-4 (laser 4), laser light source 44-5 (laser 5), and laser light source 44-6 (laser 6), so as to cause the laser light sources 44-1, 44-3, 44-4, 44-5, and 44-6 to emit first laser light, third laser light, fourth laser light, fifth laser light, and sixth laser light, as shown in FIG. 7, FIG. 9, and FIG. 21.

In this case, the light quantity ratio changing section 72 of the light source driver 46 changes the first to third light quantity ratios, as follows:

light quantity ratio (first light quantity ratio) between first laser light and second laser light=1:0 light quantity ratio (second light quantity ratio) between third laser light and fourth laser light=0.5:0.5 light quantity ratio (third light quantity ratio) between fifth laser light and sixth laser light=0.5:0.5

Laser light source 44-1 (laser 1) is an emphasis narrow band light source corresponding to the superficial blood vessels 68s (superficial region 70s), and the first laser light emitted from laser light source 44-1 (laser 1) is emphasis narrow band light corresponding to the superficial blood vessels 68s (superficial region 70s). The wavelength of the first laser light is 415 nm and is included in the blue range 58B, as shown in FIG. 9 and FIG. 21.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light is 540 nm and is included in the green range 58G, as shown in FIG. 9 and FIG. 21.

Laser light source 44-4 (laser 4) is a non-emphasis narrow band light source corresponding to the intermediate blood vessels 68m (intermediate region 70m), and the fourth laser light emitted from laser light source 44-4 (laser 4) is non-emphasis narrow band light corresponding to the intermediate blood vessels 68m (intermediate region 70m). The wavelength of the fourth laser light is 515 nm and is included in the green range 58G, as shown in FIG. 9 and FIG. 21.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9 and FIG. 21.

Laser light source 44-6 (laser 6) is a non-emphasis narrow band light source corresponding to the deep blood vessels 68d (deep region 70d), and the sixth laser light emitted from laser light source 44-6 (laser 6) is non-emphasis narrow band light corresponding to the deep blood vessels 68d (deep region 70d). The wavelength of the sixth laser light is 635 nm and is included in the red range 58R, as shown in FIG. 9 and FIG. 21.

The first laser light, third laser light, fourth laser light, fifth laser light, and sixth laser light are combined together, as described above, and the resultant light is emitted from the light converter 54 at the distal end of the insertion section 26 and radiated to the observation object O as illumination light IL. In other words, in this observation mode M14 (superficial, intermediate, and deep blood vessel intermediate-emphasis mode 1), the third laser light that emphasizes the intermediate blood vessels 68m and the fourth laser light that does not emphasize the intermediate blood vessels 68m are both radiated to the observation object O, and the fifth laser light that emphasizes the deep blood vessels 68d and the sixth laser light that does not emphasize the deep blood vessels 68d are both radiated to the observation object O.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the superficial blood vessels 68s is more different from the light intensity that the reflected and scattered light RL has near the blood vessels (in the mucous membrane or the like), than the light intensity that the reflected and scattered light RL has in the intermediate blood vessels 68m and the deep blood vessels 68d.

The image processor 24 performs at least one of the contrast emphasis image process, outline (edge) emphasis image process, and blood vessel structure emphasis image process for the imaging signal (the B imaging signal in this case) that is one of the B imaging signal, G imaging signal, and R imaging signal and that corresponds to the color range including only the emphasis narrow band light. The imaging signals corresponding to the remaining color ranges (the G imaging signal and the R imaging signal in this case) are not subjected to the emphasis image process or suppression image process.

Figure 22:
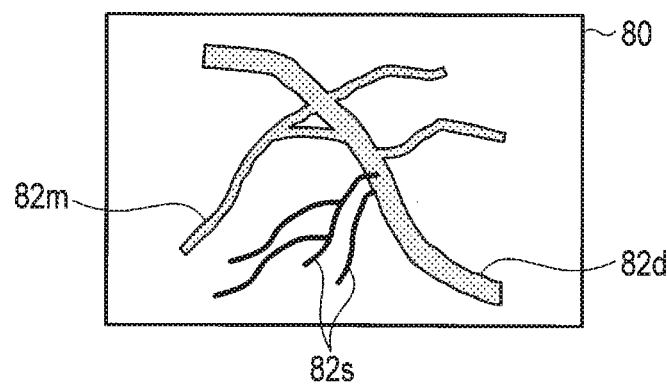
FIG. 22 is a diagram showing an example of an observation object image displayed in observation mode M14 (superficial, intermediate, and deep blood vessel intermediate-emphasis mode 1).

The B image signal, G image signal, and R image signal generated by the image processor 24 are transmitted to the image display 16 and are displayed as an observation object image 80, as shown in FIG. 10 and FIG. 22. That is, in this observation object image 80, the superficial blood vessels 68s are highlighted as a superficial blood vessel image 82s, as in observation mode M1 (superficial blood vessel emphasis mode).

On the other hand, in this observation mode M14 (superficial, intermediate, and deep blood vessel intermediate-emphasis mode 1), the third laser light that emphasizes the intermediate blood vessels 68m and the fourth laser light that does not emphasize the intermediate blood vessels 68m are both radiated to the observation object O. As a result, the intermediate blood vessels 68m are emphasized at a level that is intermediate between the state where they are emphasized with only the third laser light radiated and the state where they are not emphasized with only the fourth laser light radiated. That is, the intermediate blood vessel image 82m showing the intermediate blood vessels 68m is highlighted at an intermediate level between observation mode M1 (the superficial blood vessel emphasis mode) and observation mode M4 (the superficial and intermediate blood vessel emphasis mode).

The fifth laser light that emphasizes the deep blood vessels 68d and the sixth laser light that does not emphasize the deep blood vessels 68d are both radiated to the observation object O. As a result, the deep blood vessels 68d are emphasized at a level that is intermediate between the state where they are emphasized with only the fifth laser light radiated and the state where they are not emphasized with only the sixth laser light radiated. That is, the deep blood vessel image 82d showing the deep blood vessels 68d is highlighted at an intermediate level between observation mode M1 (the superficial blood vessel emphasis mode) and observation mode M5 (the superficial and deep blood vessel emphasis mode).

In an image of such an intermediate-level emphasis state, the observation object image 80 provides an enhanced sense of depth, in comparison with an image in which only the superficial blood vessels 68s are emphasized, an image in which the superficial blood vessels 68s and the intermediate blood vessels 68m are emphasized, and an image in which the superficial blood vessels 68s and the deep blood vessels 68d are emphasized.

Needless to say, the light quantity ratio (second light quantity ratio) between the third laser light and the fourth laser light can be changed, like the second light quantity ratio in observation mode M8 (superficial and intermediate blood vessel intermediate-emphasis mode 1).

Needless to say, the light quantity ratio (third light quantity ratio) between the fifth laser light and the sixth laser light can also be changed, like the light quantity ratio (second light quantity ratio) between the third laser light and the fourth laser light in observation mode M8 (superficial and intermediate blood vessel intermediate-emphasis mode 1).

<Observation Mode M15 (Superficial, Intermediate, and Deep Blood Vessel Intermediate-Emphasis Mode 2)>

Where the user enters observation mode M15 (superficial, intermediate, and deep blood vessel intermediate-emphasis mode 2) from the input device 18 as an observation mode, the input device 18 outputs observation mode information on observation mode M15 (superficial, intermediate, and deep blood vessel intermediate-emphasis mode 2) to the light source driver 46 and the image processor 24.

Upon receipt of the observation mode information on observation mode M15 (superficial, intermediate, and deep blood vessel intermediate-emphasis mode 2), the light source driver 46 turns on laser light source 44-1 (laser 1), laser light source 44-2 (laser 2), laser light source 44-3 (laser 3), laser light source 44-5 (laser 5), and laser light source 44-6 (laser 6), so as to cause the laser light sources 44-1, 44-2, 44-3, 44-5, and 44-6 to emit first laser light, second laser light, third laser light, fifth laser light, and sixth laser light, as shown in FIG. 7 and FIG. 9.

In this case, the light quantity ratio changing section 72 of the light source driver 46 changes the first to third light quantity ratios, as follows:

light quantity ratio (first light quantity ratio) between first laser light and second laser light=0.5:0.5 light quantity ratio (second light quantity ratio) between third laser light and fourth laser light=1:0 light quantity ratio (third light quantity ratio) between fifth laser light and sixth laser light=0.5:0.5

Laser light source 44-1 (laser 1) is an emphasis narrow band light source corresponding to the superficial blood vessels 68s (superficial region 70s), and the first laser light emitted from laser light source 44-1 (laser 1) is emphasis narrow band light corresponding to the superficial blood vessels 68s (superficial region 70s). The wavelength of the first laser light is 415 nm and is included in the blue range 58B, as shown in FIG. 9.

Laser light source 44-2 (laser 2) is a non-emphasis narrow band light source corresponding to the superficial blood vessels 68s (superficial region 70s), and the second laser light emitted from laser light source 44-2 (laser 2) is non-emphasis narrow band light corresponding to the superficial blood vessels 68s (superficial region 70s). The wavelength of the second laser light is 445 nm and is included in the blue range 58B, as shown in FIG. 9.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light is 540 nm and is included in the green range 58G, as shown in FIG. 9.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9.

Laser light source 44-6 (laser 6) is a non-emphasis narrow band light source corresponding to the deep blood vessels 68d (deep region 70d), and the sixth laser light emitted from laser light source 44-6 (laser 6) is non-emphasis narrow band light corresponding to the deep blood vessels 68d (deep region 70d). The wavelength of the sixth laser light is 635 nm and is included in the red range 58R, as shown in FIG. 9.

The first laser light, second laser light, third laser light, fifth laser light, and sixth laser light are combined together, as described above, and the resultant light is emitted from the light converter 54 at the distal end of the insertion section 26 and radiated to the observation object O as illumination light IL. In other words, in this observation mode M15 (superficial, intermediate, and deep blood vessel intermediate-emphasis mode 2), the first laser light that emphasizes the superficial blood vessels 68*s* and the second laser light that does not emphasize the superficial blood vessels 68*s* are both radiated to the observation object O, and the fifth laser light that emphasizes the deep blood vessels 68*d* and the sixth laser light that does not emphasize the deep blood vessels 68*d* are both radiated to the observation object O.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the intermediate blood vessels 68*m* is more different from the light intensity that the reflected and scattered light RL has near the blood vessels (in the mucous membrane or the like), than the light intensity that the reflected and scattered light RL has in the superficial blood vessels 68*s* and the deep blood vessels 68*d*.

The image processor 24 performs at least one of the contrast emphasis image process, outline (edge) emphasis image process, and blood vessel structure emphasis image process for the imaging signal (the G imaging signal in this case) that is one of the B imaging signal, G imaging signal, and R imaging signal and that corresponds to the color range including only the emphasis narrow band light. The imaging signals corresponding to the remaining color ranges (the B imaging signal and the R imaging signal in this case) are not subjected to the emphasis image process or suppression image process.

The B image signal, G image signal, and R image signal generated by the image processor 24 are transmitted to the image display 16 and are displayed as an observation object image 80, as shown in FIG. 10. That is, in this observation object image 80, the intermediate blood vessels 68*m* are highlighted as a intermediate blood vessel image 82*m*, as in observation mode M2 (intermediate blood vessel emphasis mode).

On the other hand, in this observation mode M15 (superficial, intermediate, and deep blood vessel intermediate-emphasis mode 2), the first laser light that emphasizes the superficial blood vessels 68*s* and the second laser light that does not emphasize the superficial blood vessels 68*s* are both radiated to the observation object O. As a result, the superficial blood vessels 68*s* are emphasized at a level that is intermediate between the state where they are emphasized with only the first laser light radiated and the state where they are not emphasized with only the second laser light radiated. That is, the superficial blood vessel image 82*s* showing the superficial blood vessels 68*s* is highlighted at an intermediate level between observation mode M2 (the intermediate blood vessel emphasis mode) and observation mode M4 (the superficial and intermediate blood vessel emphasis mode).

The fifth laser light that emphasizes the deep blood vessels 68*d* and the sixth laser light that does not emphasize the deep blood vessels 68*d* are both radiated to the observation object O. As a result, the deep blood vessels 68*d* are emphasized at a level that is intermediate between the state where they are emphasized with only the fifth laser light radiated and the state where they are not emphasized with only the sixth laser light radiated. That is, the deep blood vessel image 82*d* showing the deep blood vessels 68*d* is highlighted at an intermediate level between observation mode M2 (the intermediate blood vessel emphasis mode) and observation mode M6 (the intermediate and deep blood vessel emphasis mode).

In an image of such an intermediate-level emphasis state, the observation object image 80 provides an enhanced sense of depth, in comparison with an image in which only the intermediate blood vessels 68*m* are emphasized, an image in which the superficial blood vessels 68*s* and the intermediate blood vessels 68*m* are emphasized, and an image in which the intermediate blood vessels 68*m* and the deep blood vessels 68*d* are emphasized.

Needless to say, the light quantity ratio (first light quantity ratio) between the first laser light and the second laser light and the light quantity ratio (third light quantity ratio) between the fifth laser light and the sixth laser light can be changed, like the light quantity ratio (second light quantity ratio) between the third laser light and the fourth laser light in observation mode M8 (superficial and intermediate blood vessel intermediate-emphasis mode 1).

<Observation Mode M16 (Superficial, Intermediate, and Deep Blood Vessel Intermediate-Emphasis Mode 3)>

Where the user enters observation mode M16 (superficial, intermediate, and deep blood vessel intermediate-emphasis mode 3) from the input device 18 as an observation mode, the input device 18 outputs observation mode information on observation mode M16 (superficial, intermediate, and deep blood vessel intermediate-emphasis mode 3) to the light source driver 46 and the image processor 24.

Upon receipt of the observation mode information on observation mode M16 (superficial, intermediate, and deep blood vessel intermediate-emphasis mode 3), the light source driver 46 turns on laser light source 44-1 (laser 1), laser light source 44-2 (laser 2), laser light source 44-3 (laser 3), laser light source 44-4 (laser 4), and laser light source 44-5 (laser 5), so as to cause the laser light sources 44-1, 44-2, 44-3, 44-4, and 44-5 to emit first laser light, second laser light, third laser light, fourth laser light, and fifth laser light, as shown in FIG. 7 and FIG. 9.

In this case, the light quantity ratio changing section 72 of the light source driver 46 changes the first to third light quantity ratios, as follows:

light quantity ratio (first light quantity ratio) between first laser light and second laser light=0.5:0.5 light quantity ratio (second light quantity ratio) between third laser light and fourth laser light=0.5:0.5 light quantity ratio (third light quantity ratio) between fifth laser light and sixth laser light=1:0

Laser light source 44-1 (laser 1) is an emphasis narrow band light source corresponding to the superficial blood vessels 68*s* (superficial region 70*s*), and the first laser light emitted from laser light source 44-1 (laser 1) is emphasis narrow band light corresponding to the superficial blood vessels 68*s* (superficial region 70*s*). The wavelength of the first laser light is 415 nm and is included in the blue range 58B, as shown in FIG. 9.

Laser light source 44-2 (laser 2) is a non-emphasis narrow band light source corresponding to the superficial blood vessels 68*s* (superficial region 70*s*), and the second laser light emitted from laser light source 44-2 (laser 2) is non-emphasis narrow band light corresponding to the superficial blood vessels 68s (superficial region 70s). The wavelength of the second laser light is 445 nm and is included in the blue range 58B, as shown in FIG. 9.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light is 540 nm and is included in the green range 58G, as shown in FIG. 9.

Laser light source 44-4 (laser 4) is a non-emphasis narrow band light source corresponding to the intermediate blood vessels 68m (intermediate region 70m), and the fourth laser light emitted from laser light source 44-4 (laser 4) is non-emphasis narrow band light corresponding to the intermediate blood vessels 68m (intermediate region 70m). The wavelength of the fourth laser light is 515 nm and is included in the green range 58G, as shown in FIG. 9.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9.

The first laser light, second laser light, third laser light, fourth laser light, and fifth laser light are combined together, as described above, and the resultant light is emitted from the light converter 54 at the distal end of the insertion section 26 and radiated to the observation object O as illumination light IL. In other words, in this observation mode M16 (superficial, intermediate, and deep blood vessel intermediate-emphasis mode 3), the first laser light that emphasizes the superficial blood vessels 68s and the second laser light that does not emphasize the superficial blood vessels 68s are both radiated to the observation object O, and the third laser light that emphasizes the intermediate blood vessels 68m and the fourth laser light that does not emphasize the intermediate blood vessels 68m are both radiated to the observation object O.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

That is, the light intensity that the reflected and scattered light RL of the illumination light IL has in the deep blood vessels 68d is more different from the light intensity that the reflected and scattered light RL has near the blood vessels (in the mucous membrane or the like), than the light intensity that the reflected and scattered light RL has in the superficial blood vessels 68s and the intermediate blood vessels 68m.

The image processor 24 performs at least one of the contrast emphasis image process, outline (edge) emphasis image process, and blood vessel structure emphasis image process for the imaging signal (the R imaging signal in this case) that is one of the B imaging signal, G imaging signal, and R imaging signal and that corresponds to the color range including only the emphasis narrow band light. The imaging signals corresponding to the remaining color ranges (the B imaging signal and the G imaging signal in this case) are not subjected to the emphasis image process or suppression image process.

The B image signal, G image signal, and R image signal generated by the image processor 24 are transmitted to the image display 16 and are displayed as an observation object image 80, as shown in FIG. 10. That is, in this observation object image 80, the deep blood vessels 68d are highlighted as a deep blood vessel image 82d, as in observation mode M3 (deep blood vessel emphasis mode).

On the other hand, in this observation mode M16 (superficial, intermediate, and deep blood vessel intermediate-emphasis mode 3), the first laser light that emphasizes the superficial blood vessels 68s and the second laser light that does not emphasize the superficial blood vessels 68s are both radiated to the observation object O. As a result, the superficial blood vessels 68s are emphasized at a level that is intermediate between the state where they are emphasized with only the first laser light radiated and the state where they are not emphasized with only the second laser light radiated. That is, the superficial blood vessel image 82s showing the superficial blood vessels 68s is highlighted at an intermediate level between observation mode M3 (the deep blood vessel emphasis mode) and observation mode M5 (the superficial and deep blood vessel emphasis mode).

The third laser light that emphasizes the intermediate blood vessels 68m and the fourth laser light that does not emphasize the intermediate blood vessels 68m are both radiated to the observation object O. As a result, the intermediate blood vessels 68m are emphasized at a level that is intermediate between the state where they are emphasized with only the third laser light radiated and the state where they are not emphasized with only the fourth laser light radiated. That is, the intermediate blood vessel image 82m showing the intermediate blood vessels 68m is highlighted at an intermediate level between observation mode M3 (the deep blood vessel emphasis mode) and observation mode M6 (the intermediate and deep blood vessel emphasis mode).

In an image of such an intermediate-level emphasis state, the observation object image 80 provides an enhanced sense of depth, in comparison with an image in which only the deep blood vessels 68d are emphasized, an image in which the superficial blood vessels 68s and the deep blood vessels 68d are emphasized, and an image in which the intermediate blood vessels 68m and the deep blood vessels 68d are emphasized.

Needless to say, the light quantity ratio (first light quantity ratio) between the first laser light and the second laser light and the light quantity ratio (second light quantity ratio) between the third laser light and the fourth laser light can be changed, like the light quantity ratio (second light quantity ratio) between the third laser light and the fourth laser light in observation mode M8 (superficial and intermediate blood vessel intermediate-emphasis mode 1).

<Observation Mode M17 (Normal Observation Mode)>

Where the user enters observation mode M17 (the normal observation mode) from the input device 18 as an observation mode, the input device 18 outputs observation mode information on observation mode M17 (the normal observation mode) to the light source driver 46 and the image processor 24.

Figure 23:
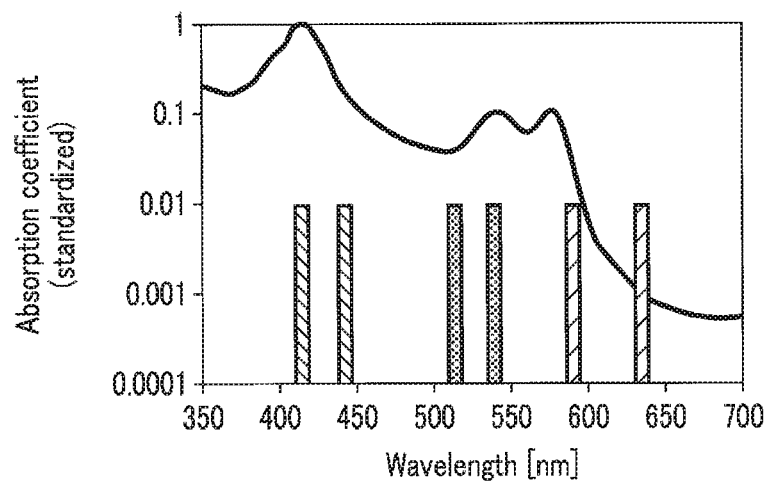
FIG. 23 is a diagram showing how an illumination light spectrum is in observation mode M17 (normal observation mode).

Upon receipt of the observation mode information on observation mode M3 (deep blood vessel emphasis mode), the light source driver 46 turns on laser light source 44-1 (laser 1), laser light source 44-2 (laser 2), laser light source 44-3 (laser 3), laser light source 44-4 (laser 4), laser light source 44-5 (laser 5), and laser light source 44-6 (laser 6), so as to cause the laser light sources 44-1, 44-2, 44-3, 44-4, 44-5, and 44-6 to emit first laser light, second laser light, third laser light, fourth laser light, fifth laser light, and sixth laser light, as shown in FIG. 7, FIG. 9, and FIG. 23.

In this case, the light quantity ratio changing section 72 of the light source driver 46 changes the first to third light quantity ratios, as follows:

light quantity ratio (first light quantity ratio) between first laser light and second laser light=0.5:0.5 light quantity ratio (second light quantity ratio) between third laser light and fourth laser light=0.5:0.5 light quantity ratio (third light quantity ratio) between fifth laser light and sixth laser light=0.5:0.5

Laser light source 44-1 (laser 1) is an emphasis narrow band light source corresponding to the superficial blood vessels 68s (superficial region 70s), and the first laser light emitted from laser light source 44-1 (laser 1) is emphasis narrow band light corresponding to the superficial blood vessels 68s (superficial region 70s). The wavelength of the first laser light is 415 nm and is included in the blue range 58B, as shown in FIG. 9 and FIG. 23.

Laser light source 44-2 (laser 2) is a non-emphasis narrow band light source corresponding to the superficial blood vessels 68s (superficial region 70s), and the second laser light emitted from laser light source 44-2 (laser 2) is non-emphasis narrow band light corresponding to the superficial blood vessels 68s (superficial region 70s). The wavelength of the second laser light is 445 nm and is included in the blue range 58B, as shown in FIG. 9 and FIG. 23.

Laser light source 44-3 (laser 3) is an emphasis narrow band light source corresponding to the intermediate blood vessels 68m (intermediate region 70m), and the third laser light emitted from laser light source 44-3 (laser 3) is emphasis narrow band light corresponding to the intermediate blood vessels 68m (intermediate region 70m). The wavelength of the third laser light is 540 nm and is included in the green range 58G, as shown in FIG. 9 and FIG. 23.

Laser light source 44-4 (laser 4) is a non-emphasis narrow band light source corresponding to the intermediate blood vessels 68m (intermediate region 70m), and the fourth laser light emitted from laser light source 44-4 (laser 4) is non-emphasis narrow band light corresponding to the intermediate blood vessels 68m (intermediate region 70m). The wavelength of the fourth laser light is 515 nm and is included in the green range 58G, as shown in FIG. 9 and FIG. 23.

Laser light source 44-5 (laser 5) is an emphasis narrow band light source corresponding to the deep blood vessels 68d (deep region 70d), and the fifth laser light emitted from laser light source 44-5 (laser 5) is emphasis narrow band light corresponding to the deep blood vessels 68d (deep region 70d). The wavelength of the fifth laser light is 595 nm and is included in the red range 58R, as shown in FIG. 9 and FIG. 23.

Laser light source 44-6 (laser 6) is a non-emphasis narrow band light source corresponding to the deep blood vessels 68d (deep region 70d), and the sixth laser light emitted from laser light source 44-6 (laser 6) is non-emphasis narrow band light corresponding to the deep blood vessels 68d (deep region 70d). The wavelength of the sixth laser light is 635 nm and is included in the red range 58R, as shown in FIG. 9 and FIG. 23.

The first laser light, second laser light, third laser light, fourth laser light, fifth laser light, and sixth laser light are combined together, as described above, and the resultant light is emitted from the light converter 54 at the distal end of the insertion section 26 and radiated to the observation object O as illumination light IL. In other words, in this observation mode M17 (normal observation mode), the first laser light that emphasizes the superficial blood vessels 68s and the second laser light that does not emphasize the superficial blood vessels 68s are both radiated to the observation object O, the third laser light that emphasizes the intermediate blood vessels 68m and the fourth laser light that does not emphasize the intermediate blood vessels 68m are both radiated to the observation object O, and the fifth laser light that emphasizes the deep blood vessels 68d and the sixth laser light that does not emphasize the deep blood vessels 68d are both radiated to the observation object O.

The reflected and scattered light RL of the illumination light IL in the observation object O is detected by the imager 22, as described above, and a B imaging signal, a G imaging signal, and an R imaging signal are output from the imager 22 to the image processor 24. The image processor 24 performs image processing for the B imaging signal, G imaging signal, and R imaging signal output from the imager 22 in accordance with observation mode information, and generates a B image signal, a G image signal, and an R image signal.

Figure 24:
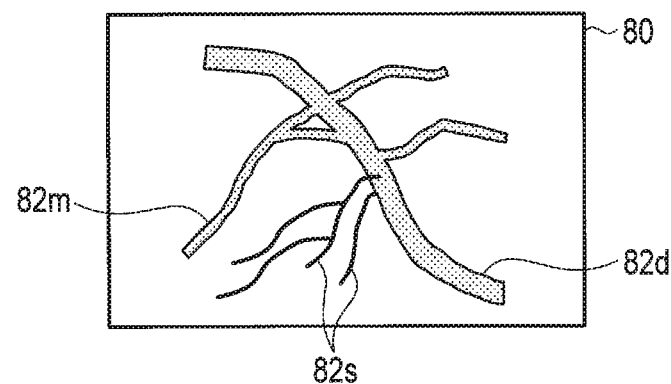
FIG. 24 is a diagram showing an example of an observation object image displayed in observation mode M17 (normal observation mode).

The B image signal, G image signal, and R image signal generated by the image processor 24 are transmitted to the image display 16 and are displayed as an observation object image 80, as shown in FIG. 10 and FIG. 24.

That is, in this observation mode M17 (normal observation mode), the first laser light that emphasizes the superficial blood vessels 68s and the second laser light that does not emphasize the superficial blood vessels 68s are both radiated to the observation object O. As a result, the superficial blood vessels 68s are emphasized at a level that is intermediate between the state where they are emphasized with only the first laser light radiated and the state where they are not emphasized with only the second laser light radiated. That is, the superficial blood vessel image 82s showing the superficial blood vessels 68s is highlighted at an intermediate level between observation mode M1 (the superficial blood vessel emphasis mode) and observation mode M6 (the intermediate and deep blood vessel emphasis mode).

The third laser light that emphasizes the intermediate blood vessels 68m and the fourth laser light that does not emphasize the intermediate blood vessels 68m are both radiated to the observation object O. As a result, the intermediate blood vessels 68m are emphasized at a level that is intermediate between the state where they are emphasized with only the third laser light radiated and the state where they are not emphasized with only the fourth laser light radiated. That is, the intermediate blood vessel image 82m showing the intermediate blood vessels 68m is highlighted at an intermediate level between observation mode M2 (the intermediate blood vessel emphasis mode) and observation mode M5 (the superficial and deep blood vessel emphasis mode).

The fifth laser light that emphasizes the deep blood vessels 68d and the sixth laser light that does not emphasize the deep blood vessels 68d are both radiated to the observation object O. As a result, the deep blood vessels 68d are emphasized at a level that is intermediate between the state where they are emphasized with only the fifth laser light radiated and the state where they are not emphasized with only the sixth laser light radiated. That is, the deep blood vessel image 82d showing the deep blood vessels 68d is highlighted at an intermediate level between observation mode M3 (the deep blood vessel emphasis mode) and observation mode M4 (the superficial and intermediate blood vessel emphasis mode).

In this observation mode M17 (the normal observation mode), the light quantity ratios of the laser light sources 44-1 to 44-6 are determined such that the illumination light IL can have high color rendering property or high color reproduction property. Therefore, the light quantity ratio (first light quantity ratio) between the first laser light and the second laser light, the light quantity ratio (second light quantity ratio) between the third laser light and the fourth laser light, and the light quantity ratio (third light quantity ratio) between the fifth laser light and the sixth laser light are not limited to 0.5:0.5 described above. For example, the color of broadband illumination light IL, such as xenon lamp or halogen lamp, is reproduced. Alternatively, the color of observation object O irradiated with broadband illumination light IL, such as xenon lamp or halogen lamp, is reproduced.

In observation mode M17 (the normal observation mode), more laser light sources are turned on than in the blood vessel emphasis modes, in order to enhance the color rendering property or color reproduction property.

As described above, an endoscope apparatus according to the embodiment of the present invention is an endoscope apparatus 10 comprising: an illuminator 20 that includes rays of narrow band light sources and that emits illumination light IL including rays of narrow band light having different peak wavelengths and different central wavelengths, the narrow band light sources including at least: a first emphasis narrow band light source that emits first emphasis narrow band light whose peak wavelength or central wavelength is included in an emphasis wavelength range, the emphasis wavelength range including at least one of a maximum wavelength that takes at least one maximum value, for an optical absorption spectrum of a diagnosis target substance present in an observation object O, and a color-range largest wavelength that takes a color-range largest value that is a largest value of the optical absorption spectrum, in one of three color ranges that are a blue range 58B, a green range 58G, and a red range 55R; and a first non-emphasis narrow band light source that emits first non-emphasis narrow band light whose peak wavelength or central wavelength is included in a non-emphasis wavelength range, the non-emphasis wavelength range being a wavelength range that does not include the emphasis wavelength range of the blue range 58B, green range 58G, and red range 58R, the illuminator 20 further including a light quantity ratio changing section 72 that changes a first light quantity ratio that is the light quantity ratio between the first emphasis narrow band light and first non-emphasis narrow band light included in the rays of narrow band light.

The emphasis degree of the diagnosis target substance to be emphasized with the first emphasis narrow band light is changed by changing the first light quantity ratio, which is the light quantity ratio between the first emphasis narrow band light and the first non-emphasis narrow band light. Therefore, the relative emphasis degree of the diagnosis target substance in a specific depth region can be changed.

Each of the first emphasis narrow band light and the first non-emphasis narrow band light has a reach length up to a first depth region, and the first depth region is one of three depth regions that are a superficial region 70s, a intermediate region 70m, and a deep region 70d of the observation object O.

Therefore, the relative emphasis degree of the diagnosis target substance in the superficial region 70s, intermediate region 70m, or deep region 70d of the observation object O can be changed.

In this case, narrow band light having a reach length up to the superficial region 70s is included in the blue range 58B, narrow band light having a reach length up to the intermediate region is included in the green range 58G, and narrow band light having a reach length up to the deep region 70d is included in the red range 58R. Each of the first emphasis narrow band light and the first non-emphasis narrow band light is included in a first color range that is one of the three color ranges.

As can be seen from this, the depth regions are correlated with the color ranges.

The light quantity ratio changing section 72 changes the first light quantity ratio such that the light quantity in the first color range is made constant in the illumination light IL.

Therefore, the color of the illumination light IL is not changed by changing the light quantity ratio.

The narrow band light sources further includes at least one of: a second emphasis narrow band light source that emits second emphasis narrow band light; and a second non-emphasis narrow band light source that emits second emphasis narrow band light. The rays of narrow band light of the illumination light IL include at least one of second emphasis narrow band light and second non-emphasis narrow band light. The second emphasis narrow band light and the second non-emphasis narrow band light have a reach length up to a second depth region that is one of the three depth regions and that is different from the first depth region, and are included in a second color range that is one of the three color ranges and that is different from the first color range.

Since the narrow band light includes the second emphasis narrow band light included in the second color range and reaching the second depth region, an image whose emphasis state is between those of two depth regions can be generated. Since the narrow band light includes the second emphasis narrow band light included in the second color range and reaching the second depth region, the color reproduction property can be enhanced.

In this case, the narrow band light sources include both the second emphasis narrow band light source and the second non-emphasis narrow band light source, the light quantity ratio changing section 72 changes, in addition to the first light quantity ratio, the second light quantity ratio that is the light quantity ratio between the second emphasis narrow band light and the second non-emphasis narrow band light.

By changing the light quantity ratio (second light quantity ratio) between the second emphasis narrow band light and the second non-emphasis narrow band light, in addition to the first light quantity ration, the blood emphasis degree for the second depth region can be changed based on the second light quantity ratio. Therefore, various images of, for example, blood vessels, can be generated. Other than an image in which the superficial blood vessels 68s and deep blood vessels 68d are emphasized, an image in which only the superficial blood vessels 68s are emphasized, an image in which only the deep blood vessels 68d are emphasized, and an image having an emphasis state intermediate between them can be generated. Where the image has an intermediate emphasis state, an observation object image 80 provides an enhanced sense of depth, in comparison with the image in which the superficial blood vessels 68s and the deep blood vessels 68d are emphasized, the image in which only the superficial blood vessels 68s are emphasized, and the image in which only the deep blood vessels 68d are emphasized.

In this case, the light quantity ratio changing section 72 preferably changes the second light quantity ratio such that the light quantity in the second color range is made constant in the illumination light IL.

By changing the second light quantity ratio such that the light quantity in the second color range is made constant, the color of the illumination light IL is not changed by the change of the light quantity ratio.

The narrow band light sources further include at least one of a third emphasis narrow band light source that emits third emphasis narrow band light, and a third non-emphasis narrow band light source that emits third non-emphasis narrow band light. The rays of narrow band light of the illumination light IL include at least one ray of third emphasis narrow band light and third non-emphasis narrow band light. The third emphasis narrow band light and the third non-emphasis narrow band light have a reach length up to a third depth region that is one of the three depth regions and that is different from the first depth region and the second depth region, and are included in a third color range that is one of the three color ranges and that is different from the first color range and the second color range.

Since the narrow band light includes the third emphasis narrow band light included in the third color range and reaching the third depth region is used, an image whose emphasis state is intermediate between those of three depth regions can be generated. Since the narrow band light includes the third emphasis narrow band light included in the third color range and reaching the third depth region is used, the color reproduction property can be enhanced.

In this case, the narrow band light sources include both the third emphasis narrow band light source and the third non-emphasis narrow band light source, the light quantity ratio changing section 72 changes, in addition to the first light quantity ratio and the second light quantity ratio, a third light quantity ratio that is a light quantity ratio between the third emphasis narrow band light and the third non-emphasis narrow band light.

By changing the light quantity ratio (third light quantity ratio) between the third emphasis narrow band light and the third non-emphasis narrow band light, in addition to the first and second light quantity ratios, the blood vessel emphasis degree for the third depth region can be changed based on the third light quantity ratio.

In this case, the light quantity ratio changing section 72 preferably changes the third light quantity ratio such that the light quantity in the third color range is made constant in the illumination light IL.

By changing the third light quantity ratio such that the light quantity in the third color range is made constant, the color of the illumination light IL is not changed by the change of the light quantity ratio.

Where the ratio among the light quantity in the blue range 58B of the illumination light IL, the light quantity in the green range 58G thereof, and the light quantity in the red range 58R thereof is an inter-color-regional light quantity ratio, the light quantity ratio changing section 72 controls the narrow band light sources such that the inter-color-regional light quantity ratio is made constant. By controlling the narrow band light sources such that the inter-color-regional light quantity ratio is made constant, the color of the illumination light IL is not changed by the change of the light quantity ratio. Where narrow band light that is neither emphasis narrow band light nor non-emphasis narrow band light exists, the inter-color-regional light quantity ratio is made constant, with such narrow band light included.

In this case, the inter-color-regional light quantity ratio is a light quantity ratio that makes illumination light IL white.

In this way, observation is enabled with enhanced color reproducibility by setting the inter-color-regional light quantity ratio at a light quantity ratio that makes the illumination light IL white.

The light quantity ratio changing section 72 switches first lighting combinations that are combinations of the on/off states of the first emphasis narrow band light source and first non-emphasis narrow band light source (i.e., the state where only the first emphasis narrow band light source is turned on, the state where only the first non-emphasis narrow band light source is turned on, and the state where both light sources are turned on).

In this way, the first light quantity ratio can be changed by changing combinations (first lighting combinations) of the on/off states of the first emphasis narrow band light source and first non-emphasis narrow band light source.

The light quantity ratio changing section 72 switches first lighting combinations that are combinations of the on/off states of the first emphasis narrow band light source and first non-emphasis narrow band light source (i.e., the state where only the first emphasis narrow band light source is turned on, the state where the first non-emphasis narrow band light source is turned on, and the state where both light sources are turned on), and also switches second lighting combinations that are combinations of the on/off states of the second emphasis narrow band light source and second non-emphasis narrow band light source (i.e., the state where only the second emphasis narrow band light source is turned on, the state where only the second non-emphasis narrow band light source is turned on, and the state where both light sources are turned on).

In this way, the first and second light quantity ratios can be changed by changing combinations (first lighting combinations) of the on/off states of the first emphasis narrow band light source and first non-emphasis narrow band light source and combinations (second lighting combinations) of the on/off states of the second emphasis narrow band light source and second non-emphasis narrow band light source.

The light quantity ratio changing section 72 switches first lighting combinations that are combinations of the on/off states of the first emphasis narrow band light source and first non-emphasis narrow band light source (i.e., the state where only the first emphasis narrow band light source is turned on, the state where only the first non-emphasis narrow band light source is turned on, and the state where both light sources are turned on), also switches second lighting combinations that are combinations of the on/off states of the second emphasis narrow band light source and second non-emphasis narrow band light source (i.e., the state where only the second emphasis narrow band light source is turned on, the state where only the second non-emphasis narrow band light source is turned on, and the state where both light sources are turned on), and further switches third lighting combinations that are combinations of the on/off states of the third emphasis narrow band light source and third non-emphasis narrow band light source (i.e., the state where only the third emphasis narrow band light source is turned on, the state where only the third non-emphasis narrow band light source is turned on, and the state where both light sources are turned on).

In this way, the first, second, and third light quantity ratios can be changed by changing combinations (first lighting combinations) of the on/off states of the first emphasis narrow band light source and first non-emphasis narrow band light source, combinations (second lighting combinations) of the on/off states of the second emphasis narrow band light source and second non-emphasis narrow band light source, and combinations (third lighting combinations) of the on/off states of the third emphasis narrow band light source and third non-emphasis narrow band light source.

The emphasis wavelength range is a wavelength range that is within ±20 nm of at least one of the maximum wavelength and color-range largest wavelength.

The emphasis wavelength range should preferably be such a wavelength range because the light absorption is large.

Alternatively, the emphasis wavelength range may be a wavelength range that is a color range in which a maximum value or a color-range largest value exists and that has values equal to or more than ½ of the maximum value or color-range largest value.

The emphasis wavelength range should preferably be such a wavelength range because the absorption is large.

The non-emphasis wavelength range includes, in the optical absorption spectrum of the diagnosis target substance, at least one of a minimum wavelength that takes at least one minimum value and a color-range smallest wavelength that takes a smallest value in one of the three color ranges.

The non-emphasis wavelength range should preferably be such a wavelength range because the absorption is small.

In this case, the non-emphasis wavelength range is a wavelength range that is within ±20 nm of at least one of the minimum wavelength and color-range smallest wavelength.

The non-emphasis wavelength range should preferably be such a wavelength range because the light absorption is small.

Alternatively, the non-emphasis wavelength range may be a wavelength range that is a color range in which a minimum value or a color-range smallest value exists and that has values equal to or less than 1.5 times of at least one of the minimum value and color-range smallest value.

The non-emphasis wavelength range should preferably be such a wavelength range because the absorption is small. Alternatively, the non-emphasis wavelength range may be a wavelength range that is a color range in which a maximum value or a color-range largest value exists and that has values equal to or more than ½ of at least one of the maximum value and color-range largest value.

The non-emphasis wavelength range should preferably be such a wavelength range because the absorption is small.

The observation object O is a living tissue, and the diagnosis target substance is hemoglobin contained in the observation object O.

Owing to this, the blood vessels in the living tissues can be emphasized.

In this case, the peak wavelength of at least one ray of emphasis narrow band light is in the wavelength range from 395 to 435 nm.

Owing to this, the superficial blood vessels 68s can be emphasized.

Alternatively, the peak wavelength of at least one ray of emphasis narrow band light may be in either the wavelength range from 520 to 560 nm or the wavelength range from 560 to 595 nm.

Owing to this, the intermediate blood vessels 68m or the deep blood vessels 68d can be emphasized.

The rays of narrow band light are narrow band light having a wavelength width of 50 nm or less.

Owing to this, LEDs can be employed as the narrow band light sources.

Alternatively, the rays of narrow band light may be rays of ultra-narrow band light having a wavelength width of 5 nm or less.

Owing to this, laser light sources can be employed as the narrow band light sources.

The blue range 58B is a wavelength range from 380 to 510 nm, the green range 58G is a wavelength range from 490 to 610 nm, and the red range is a wavelength range from 590 to 780 nm.

By this wavelength setting, illumination light IL having good color reproduction property can be generated.

The endoscope apparatus 10 further comprises an input device 18 through which an observation mode suitable for a purpose is entered, and the light quantity ratio changing section 72 changes the first light quantity ratio in accordance with the observation mode entered from the input device 18.

Therefore, the light quantity ratio can be changed based on the entered observation mode.

The endoscope apparatus 10 further comprises an imager 22 that detects reflected and scattered light RL of the illumination light radiated to the observation object O and that outputs an imaging signal, and an image processor 24 that generates an image signal from the imaging signal.

Therefore, the emphasis degree of the diagnosis target substance to be emphasized with the first emphasis narrow band light is changed by changing the first light quantity ratio, which is a light quantity ratio between the first emphasis narrow band light and the first non-emphasis narrow band light, so that the relative emphasis degree of the diagnosis target substance in a specific depth region can be changed.

[Modification 1]

Figure 25:
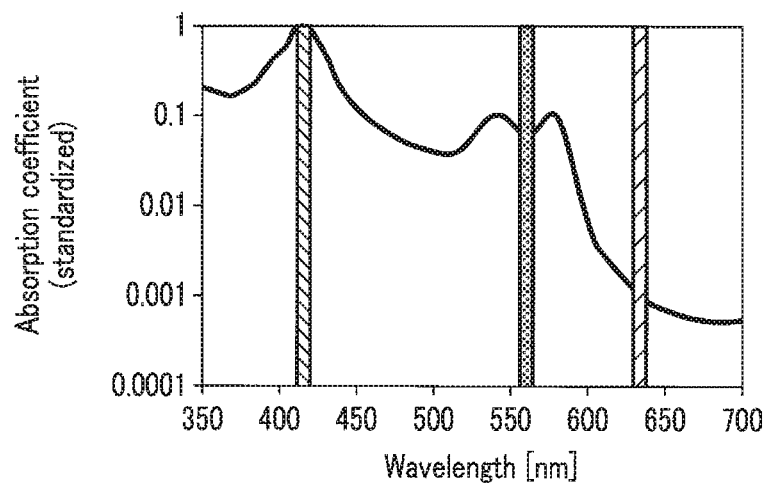
FIG. 25 is a diagram showing an example of how an illumination light spectrum is in observation mode M1 (superficial blood vessel emphasis mode) according to modification 1.
Figure 26:
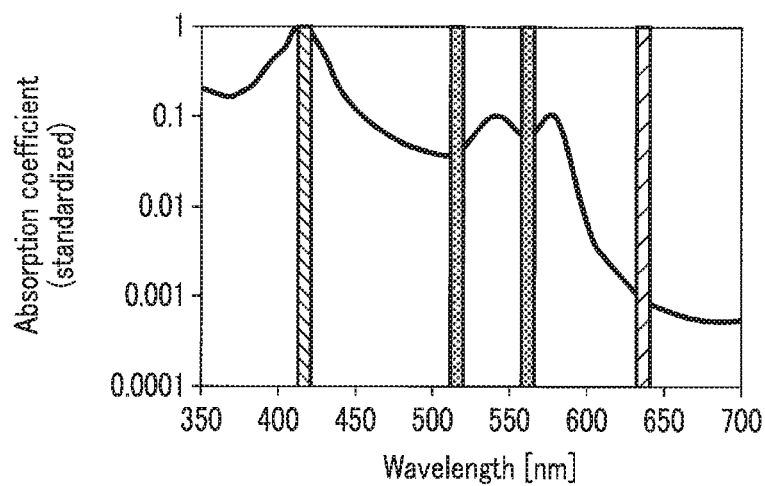
FIG. 26 is a diagram showing another example of how the illumination light spectrum is in observation mode M1 (superficial blood vessel emphasis mode) according to modification 1.

Examples of how the illumination light spectrum is modified in observation mode M1 (the superficial blood vessel emphasis mode) are shown in FIGS. 25 to 27.

The wavelength of the fourth laser light, the non-emphasis narrow band light corresponding to the intermediate blood vessels 68m, need not be 515 nm but may be 560 nm (a minimum value in the green range 58G), as shown in FIG. 25.

The total number of rays of emphasis narrow band light and non-emphasis narrow band light included in the illumination light IL may be four or more. Where the number of rays of narrow band light is four or more, the illumination light IL has higher color rendering property and higher color reproduction property. In this case, as shown in FIG. 26, two or more rays of non-emphasis narrow band light may be included in the same color range. As shown in FIG. 27, two or more rays of emphasis narrow band light may be included in the same color range (the blue range 58B in observation mode M1 (the superficial blood vessel emphasis mode)).

This holds true for the emphasis modes other than observation mode M1 (the superficial blood vessel emphasis mode).

[Modification 2]

By sequentially switching combinations of laser light sources corresponding to observation modes, observation object images 80 corresponding to the respective observation modes may be simultaneously displayed on the image display 16.

For example, observation object images 80 corresponding to four observation modes are simultaneously displayed as follows. That is, one frame period, which is a general acquisition period for an imaging signal, is divided into four sub frame periods, as shown in FIG. 28, each sub frame is made to correspond to one of observation modes, and combinations of laser sources corresponding to the observation modes are sequentially switched from one to another. FIG. 28 shows an example of the case where observation object images 80 corresponding to four observation modes, which are observation mode M1 (superficial blood vessel emphasis mode), observation mode M2 (intermediate blood vessel emphasis mode), observation mode M3 (deep blood vessel emphasis mode), and observation mode M17 (normal observation mode), are simultaneously displayed. The same display operation can be performed for four of other observation modes.

The storage 74 of the light source driver 46 has stored a table of laser light source lighting timings/imaging signal acquisitions, such as the table shown in FIG. 28, and the light source driver 46 sequentially switches combinations of laser light sources for each sub frame, based on the table stored in the storage 74.

Alternatively, as shown in, for example, FIG. 29, one frame period may be divided into two sub frame periods, and three laser light sources may be turned on in each sub frame. In the first sub frame of the two sub frames, laser light source 44-1 (laser 1), laser light source 44-3 (laser 3), and laser light source 44-5 (laser 5) are turned on, and in the second sub frame, laser light source 44-2 (laser 2), laser light source 44-4 (laser 4), and laser light source 44-6 (laser 6) are turned on. In this manner, all imaging signals of laser light sources 44-1 to 44-6 are acquired in the two sub frames, and images corresponding to the respective observation modes are generated using the imaging signals. That is, the storage 74 of the light source driver 46 has stored a table of laser light source lighting timings/imaging signal acquisitions, such as the table shown in FIG. 29, and the light source driver 46 sequentially switches combinations of laser light sources for each sub frame, based on the table stored in the storage 74.

The lighting timings shown in FIG. 28 and FIG. 29 are just examples, and blue, green, and red imaging signals required for image generation of observation modes may be acquired in other methods.

The number of observation modes that are sequentially switched or simultaneously displayed is not limited to four; a two or more arbitrary number of observation modes can be put into practice.

[Modification 3]

In the embodiment, the light quantity ratio changing section 72 changes the first light quantity ratio, the second light quantity ratio, and the third light quantity ratio, in accordance with the observation mode entered by the user through the input device 18. However, the first to third light quantity ratios can be automatically changed to switch observation modes, without the use of the input device 18.

For example, observation modes may be switched from one to another in accordance with the distance between the distal end of the insertion section 26 of the endoscope 12 and the observation object O. In a situation in which screening is performed in endoscopic examination, the distance between the distal end of the insertion section 26 and the observation object O is comparatively long. In the screening, the discovery of a lesion is intended, so that the observation of superficial blood vessels 68s is important. Therefore, where the distance between the distal end of the insertion section 26 and the observation object O is comparatively long, the light quantity ratio changing section 72 changes the first light ratio, second light ratio, and third light ratio such that the observation mode is one of those modes in which the superficial blood vessels 68s are emphasized, which are observation mode M1 (superficial blood vessel emphasis mode), observation mode M4 (superficial and intermediate blood vessel emphasis mode), observation mode M8 (superficial and intermediate blood vessel intermediate-emphasis mode 1), and observation mode M14 (superficial, intermediate, and deep blood vessel intermediate-emphasis mode 1).

When EMR (endoscopic mucosal resection) and ESD (endoscopic submucosal dissection) are to be performed in endoscopic treatment, care should be taken not to cut a relatively thick blood vessel, such as an intermediate blood vessel 68m or a deep blood vessel 68d. Therefore, the light quantity ratio changing section 72 changes the first light ratio, second light ratio, and third light ratio such that the observation mode is one of those modes in which the intermediate blood vessels 68m and the deep blood vessels 68d are emphasized, which are observation mode M2 (intermediate blood vessel emphasis mode), observation mode M3 (deep blood vessel emphasis mode), observation mode M6 (intermediate and deep blood vessel emphasis mode), observation mode M12 (intermediate and deep blood vessel intermediate-emphasis mode 1), observation mode M13 (intermediate and deep blood vessel intermediate-emphasis mode 2), observation mode M15 (superficial, intermediate, and deep blood vessel intermediate-emphasis mode 2), and observation mode M16 (superficial, intermediate, and deep blood vessel intermediate-emphasis mode 3). The observation object image 80 provides an enhanced sense of depth by using an intermediate-emphasis observation mode, such as observation mode M12 (intermediate and deep blood vessel intermediate-emphasis mode 1), observation mode M13 (intermediate and deep blood vessel intermediate-emphasis mode 2), observation mode M15 (superficial, intermediate, and deep blood vessel intermediate-emphasis mode 2), or observation mode M16 (superficial, intermediate, and deep blood vessel intermediate-emphasis mode 3). Therefore, in comparison with observation modes in which one or two kinds of blood vessels are emphasized, as in observation mode M2 (intermediate blood vessel emphasis mode), observation mode M3 (deep blood vessel emphasis mode), and observation mode M6 (intermediate and deep blood vessel emphasis mode), the use of an intermediate-emphasis observation modes is desirable because it is easy to understand how deep the intermediate blood vessels 68m and the deep blood vessels 68d are located.

[Modification 4]

According to the embodiment described above, the endoscope apparatus 10 has the following 17 observation modes: observation mode M1 (superficial blood vessel emphasis mode); observation mode M2 (intermediate blood vessel emphasis mode); observation mode M3 (deep blood vessel emphasis mode); observation mode M4 (superficial and intermediate blood vessel emphasis mode); observation mode M5 (superficial and deep blood vessel emphasis mode); observation mode M6 (intermediate and deep blood vessel emphasis mode); observation mode M7 (superficial, intermediate, and deep blood vessel emphasis mode); observation mode M8 (superficial and intermediate blood vessel intermediate-emphasis mode 1); observation mode M9 (superficial and intermediate blood vessel intermediate-emphasis mode 2); observation mode M10 (superficial and deep blood vessel intermediate-emphasis mode 1); observation mode M11 (superficial and deep blood vessel intermediate-emphasis mode 2); observation mode M12 (intermediate and deep blood vessel intermediate-emphasis mode 1); observation mode M13 (intermediate and deep blood vessel intermediate-emphasis mode 2); observation mode M14 (superficial, intermediate, and deep blood vessel intermediate-emphasis mode 1); observation mode M15 (superficial, intermediate, and deep blood vessel intermediate-emphasis mode 2); observation mode M16 (superficial, intermediate, and deep blood vessel emphasis-intermediate mode 3); and observation mode M17 (normal observation mode). However, the endoscope apparatus 10 need not have all of these observation modes.

Of the observation modes described above, the endoscope apparatus 10 may have at least one of observation mode M1 (superficial blood vessel emphasis mode), observation mode M2 (intermediate blood vessel emphasis mode), and observation mode M3 (deep blood vessel emphasis mode); alternatively, it may have at least one of observation mode M8 (superficial and intermediate blood vessel intermediate-emphasis mode 1), observation mode M9 (superficial and intermediate blood vessel intermediate-emphasis mode 2), observation mode M10 (superficial and deep blood vessel intermediate-emphasis mode 1), observation mode M11 (superficial and deep blood vessel intermediate-emphasis mode 2), observation mode M12 (intermediate and deep blood vessel intermediate-emphasis mode 1), observation mode M13 (intermediate and deep blood vessel intermediate-emphasis mode 2), observation mode M14 (superficial, intermediate, and deep blood vessel intermediate-emphasis mode 1), observation mode M15 (superficial, intermediate, and deep blood vessel intermediate-emphasis mode 2), and observation mode M16 (superficial, intermediate, and deep blood vessel emphasis-intermediate mode 3).

The endoscope apparatus 10 may also have another observation mode. The endoscope apparatus 10 may have a mode in which normal light having different color tones are radiated, a specific light observation mode in which a specific target substance in an observation object O is highlighted, a fluorescent light observation mode in which fluorescent light generated when an observation object O or a pharmacological agent is radiated with excitation light is observed.

[Modification 5]

In the embodiment, the diagnosis target substance is oxyhemoglobin, but may be another substance.

For example, the diagnosis target substance may be reduced hemoglobin, which has such an absorption spectrum as shown in FIG. 30.

The diagnosis target substance may be blood in which oxyhemoglobin and reduced hemoglobin are mixed with each other. In this case, the absorption spectrum is a spectrum obtained by multiplying the mixture ratio of the oxyhemoglobin and reduced hemoglobin.

Other than hemoglobin, the diagnosis target substance may be, for example, a known autofluorescent substance, a fluorescent pharmacological agent, or a substance contained in a living body, such as the fat, bilirubin or sugar.

The present invention has been described based on the embodiments but is in no way limited to the embodiments described above. Needless to say, the present invention can be modified in various manners, without departing from the spirit and scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An endoscope apparatus comprising:
an illuminator that includes narrow band light sources and that emits illumination light including rays of narrow band light having different peak wavelengths and different central wavelengths,
the narrow band light sources including:
a first emphasis narrow band light source that emits first emphasis narrow band light whose peak wavelength or central wavelength is included in a first emphasis wavelength range, the first emphasis wavelength range including, for an optical absorption spectrum of a diagnosis target substance present in an observation object, a color-range largest wavelength that takes a color-range largest value that is a largest value of the optical absorption spectrum in a first color range that is one of three color ranges that are a blue range, a green range, and a red range;
a first non-emphasis narrow band light source that emits first non-emphasis narrow band light whose peak wavelength or central wavelength is included in a first non-emphasis wavelength range, the first non-emphasis wavelength range being a wavelength range that does not include the first emphasis wavelength range;
a second emphasis narrow band light source that emits second emphasis narrow band light whose peak wavelength or central wavelength is included in a second emphasis wavelength range, the second emphasis wavelength range including, for the optical absorption spectrum, a color-range largest wavelength that takes a color-range largest value that is a largest value of the optical absorption spectrum in a second color range that is one of three color ranges and that is different from the first color range; and
a second non-emphasis narrow band light source that emits second emphasis narrow band light whose peak wavelength or central wavelength is included in a second non-emphasis wavelength range, the second non-emphasis wavelength range being a wavelength range that does not include the first emphasis wavelength range, first non-emphasis wavelength range, and second emphasis wavelength range,
each of the first emphasis narrow band light and the first non-emphasis narrow band light having a reach length up to a first depth region,
the first depth region being one of three depth regions that are a superficial region, an intermediate region, and a deep region of the observation object,
the second emphasis narrow band light and the second non-emphasis narrow band light having a reach length up to a second depth region that is one of the three depth regions and that is different from the first depth region,
the illuminator further including a light source driver that changes a first light quantity ratio that is a light quantity ratio between the first emphasis narrow band light and first non-emphasis narrow band light included in the rays of narrow band light to a predetermined first value and that changes a second light quantity ratio that is a light quantity ratio between the second emphasis narrow band light and the second non-emphasis narrow band light included in the rays of narrow band light to a predetermined second value, in order to generate an image having an emphasis state intermediate between the first depth region and the second depth region.

2. The endoscope apparatus according to claim 1, wherein of the rays of narrow band light,
 a ray of narrow band light having a reach length up to the superficial region is included in the blue range,
 a ray of narrow band light having a reach length up to the intermediate region is included in the green range, and
 a ray of narrow band light having a reach length up to the deep region is included in the red range, and
each of the first emphasis narrow band light and the first non-emphasis narrow band light is included in the first color range.

3. The endoscope apparatus according to claim 2, wherein the light source driver changes the first light quantity ratio such that a light quantity in the first color range is made constant in the illumination light.

4. The endoscope apparatus according to claim 2, wherein the second emphasis narrow band light and the second non-emphasis narrow band light are included in the second color range.

5. The endoscope apparatus according to claim 4, wherein the light source driver changes the second light quantity ratio such that a light quantity in the second color range is made constant in the illumination light.

6. The endoscope apparatus according to claim 4, wherein the narrow band light sources further include at least one of:
 a third emphasis narrow band light source that emits third emphasis narrow band light whose peak wavelength or central wavelength is included in a third emphasis wavelength range, the third emphasis wavelength range including, for the optical absorption spectrum, a color-range largest wavelength that takes a color-range largest value that is a largest value of the optical absorption spectrum in a third color range that is one of three color ranges and that is different from the first color range and the second color range; and
 a third non-emphasis narrow band light source that emits third non-emphasis narrow band light whose peak wavelength or central wavelength is included in a third non-emphasis wavelength range, the third non-emphasis wavelength range being a wavelength range that does not include the first emphasis wavelength range, first non-emphasis wavelength range, second emphasis wavelength range, second non-emphasis wavelength range, and third emphasis wavelength range,
the rays of narrow band light of the illumination light include at least one ray of the third emphasis narrow band light and the third non-emphasis narrow band light,
the third emphasis narrow band light and the third non-emphasis narrow band light
 have a reach length up to a third depth region that is one of the three depth regions and that is different from the first depth region and the second depth region, and
 are included in third color range.

7. The endoscope apparatus according to claim 6, wherein the narrow band light sources include both the third emphasis narrow band light source and the third non-emphasis narrow band light source, and
the light source driver changes, in addition to the first light quantity ratio and the second light quantity ratio, a third light quantity ratio that is a light quantity ratio between the third emphasis narrow band light and the third non-emphasis narrow band light to a predetermined third value.

8. The endoscope apparatus according to claim 7, wherein the light source driver changes the third light quantity ratio such that a light quantity in the third color range is made constant in the illumination light.

9. The endoscope apparatus according to claim 7, wherein the light source driver switches
 first lighting combinations that are combinations of on/off states of the first emphasis narrow band light source and the first non-emphasis narrow band light source,
 second lighting combinations that are combinations of on/off states of the second emphasis narrow band light source and the second non-emphasis narrow band light source, and
 third lighting combinations that are combinations of on/off states of the third emphasis narrow band light source and the third non-emphasis narrow band light source.

10. The endoscope apparatus according to claim 6, wherein
 where a ratio among a light quantity in the blue range of the illumination light, a light quantity in the green range thereof, a light quantity in the red range thereof is an inter-color-regional light quantity ratio,
 the light source driver controls the narrow band light sources such that the inter-color-regional light quantity ratio is made constant.

11. The endoscope apparatus according to claim 10, wherein the inter-color-regional light quantity ratio is a light quantity ratio that makes the illumination light white.

12. The endoscope apparatus according to claim 1, wherein the light source driver switches first lighting combinations that are combinations of on/off states of the first emphasis narrow band light source and the first non-emphasis narrow band light source.

13. The endoscope apparatus according to claim 1, wherein
 the light source driver switches
 first lighting combinations that are combinations of on/off states of the first emphasis narrow band light source and the first non-emphasis narrow band light source, and
 second lighting combinations that are combinations of on/off states of the second emphasis narrow band light source and the second non-emphasis narrow band light source.

14. The endoscope apparatus according to claim 1, wherein the emphasis wavelength range is a wavelength range that is within ±20 nm of at least one of the maximum wavelength and the color-range largest wavelength.

15. The endoscope apparatus according to claim 1, wherein the emphasis wavelength range is a wavelength range that is the color range in which the maximum value or the color-range largest value exists and in which the optical absorption spectrum has values equal to or more than ½ of the maximum value or color-range largest value.

16. The endoscope apparatus according to claim 1, wherein the non-emphasis wavelength range includes, in an optical absorption spectrum of the diagnosis target substance, at least one of a minimum wavelength that takes a minimum value for the optical absorption spectrum and a color-range smallest wavelength that takes a smallest value in one of the three color ranges.

17. The endoscope apparatus according to claim 16, wherein the non-emphasis wavelength range is a wavelength range that is within ±20 nm of at least one of the minimum wavelength and the color-range smallest wavelength.

18. The endoscope apparatus according to claim 16, wherein the non-emphasis wavelength range is a wavelength range that is the color range in which the minimum value or the color-range smallest value exists and in which the optical absorption spectrum has values equal to or less than 1.5 times of at least one the minimum value and the color-range smallest value.

19. The endoscope apparatus according to claim 1, wherein the non-emphasis wavelength range is a wavelength range that is the color range in which the maximum value or the color-range largest value exists and in which the optical absorption spectrum has values equal to or less than ½ of at least one of the maximum value and the color-range largest value.

20. The endoscope apparatus according to claim 1, wherein
the observation object is a living tissue, and
the diagnosis target substance is hemoglobin contained in the observation target.

21. The endoscope apparatus according to claim 1, wherein a peak wavelength of at least one ray of first emphasis narrow band light is included in a wavelength range from 395 to 435 nm.

22. The endoscope apparatus according to claim 1, wherein the peak wavelength of at least one ray of emphasis narrow band light is in a wavelength range from 520 to 560 nm or a wavelength range from 560 to 595 nm.

23. The endoscope apparatus according to claim 1, wherein the rays of narrow band light are rays of narrow band light having a wavelength width of 50 nm or less.

24. The endoscope apparatus according to claim 23, wherein the rays of narrow band light are rays of ultra-narrow band light having a wavelength width of 5 nm or less.

25. The endoscope apparatus according to claim 1, wherein
the blue range is a wavelength range from 380 to 510 nm,
the green range is a wavelength range from 490 to 610 nm, and
the red range is a wavelength range from 590 to 780 nm.

26. The endoscope apparatus according to claim 1, further comprising:
an input device through which one of observation modes is entered,
the light source driver changes the first light quantity ratio, based on the observation mode entered from the input device.

27. The endoscope apparatus according to claim 1, by further comprising:
an imager that detects reflected and scattered light of the illumination light radiated to the observation object and that outputs an imaging signal; and
an image processor that generates an image signal from the imaging signal.

* * * * *